(12) United States Patent
Iqbal et al.

(10) Patent No.: US 8,796,215 B2
(45) Date of Patent: *Aug. 5, 2014

(54) NEUROTROPHIC PEPTIDES

(71) Applicant: The Research Foundation for Mental Hygiene, Inc., Menands, NY (US)

(72) Inventors: Khalid Iqbal, Staten Island, NY (US); Inge Grundke-Iqbal, Staten Island, NY (US)

(73) Assignee: Research Foundation For Mental Hygiene, Inc., Menands, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/676,649

(22) Filed: Nov. 14, 2012

(65) Prior Publication Data

US 2013/0157946 A1      Jun. 20, 2013

Related U.S. Application Data

(63) Continuation-in-part of application No. 13/044,323, filed on Mar. 9, 2011, which is a continuation-in-part of application No. 12/531,616, filed as application No. PCT/EP2008/002106 on Mar. 17, 2008, now Pat. No. 8,338,378.

(30) Foreign Application Priority Data

Mar. 16, 2007   (EP) .................................... 07450050

(51) Int. Cl.
*A01N 37/18*   (2006.01)
*A61K 38/00*   (2006.01)

(52) U.S. Cl.
USPC ....... 514/17.8; 514/17.7; 514/21.6; 514/21.9; 514/8.4

(58) Field of Classification Search
None
See application file for complete search history.

(56) References Cited

U.S. PATENT DOCUMENTS 6,472,178 B1 * 10/2002 Fandl et al. .................. 435/69.4
8,338,378 B2 * 12/2012 Mossler et al. .............. 514/17.7

* cited by examiner

*Primary Examiner* — Olga N Chernyshev
(74) *Attorney, Agent, or Firm* — David L. Nocilly; Bond Schoeneck & King, PLLC

(57) ABSTRACT

The present invention relates to a neurotrophic peptide having an amino acid sequence of VGDGGLFEKKL (SEQ ID NO: 1) and alternatively comprising an adamantyl group at the C-and/or N-terminal end. The neurotrophic peptide can rescue cognition, correct impairments in neural cell proliferation and synaptic plasticity, and thus address the cognitive defects associated with Alzheimer's disease.

11 Claims, 31 Drawing Sheets a)

b)

(a)

(b)

SEQUENCE LISTING

```
<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: neurotrophic and/or neurogenic peptide

<400> SEQUENCE: 1

Val Gly Asp Gly Gly Leu Phe Glu Lys Lys Leu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: neurotrophic and/or neurogenic peptide

<400> SEQUENCE: 2

Glu Asp Gln Gln Val His Phe Thr Pro Thr Glu Gly
1               5                   10

<210> SEQ ID NO 3
<211> LENGTH: 13
<212> TYPE: PRT
<213> ORGANISM: Artificial Sequence
<220> FEATURE:
<223> OTHER INFORMATION: neurotrophic and/or neurogenic peptide

<400> SEQUENCE: 3

Ile Pro Glu Asn Glu Ala Asp Gly Met Pro Ala Thr Val
1               5                   10

<210> SEQ ID NO 4
<211> LENGTH: 13
<212> TYPE: PRT
<213> ORGANISM: Artificial Sequence
<220> FEATURE:
<223> OTHER INFORMATION: neurotrophic and/or neurogenic peptide
```

```
<400> SEQUENCE: 4

Ile Pro Arg Asn Glu Ala Asp Gly Met Pro Ile Asn Val
1               5                   10

<210> SEQ ID NO 5
<211> LENGTH: 8
<212> TYPE: PRT
<213> ORGANISM: Artificial Sequence
<220> FEATURE:
<223> OTHER INFORMATION: neurotrophic and/or neurogenic peptide

<400> SEQUENCE: 5

Gly Asp Gly Gly Leu Phe Glu Lys
1               5

<210> SEQ ID NO 6
<211> LENGTH: 8
<212> TYPE: PRT
<213> ORGANISM: Artificial Sequence
<220> FEATURE:
<223> OTHER INFORMATION: neurotrophic and/or neurogenic peptide

<400> SEQUENCE: 6

Gly Leu Phe Glu Lys Lys Leu Trp
1               5

<210> SEQ ID NO 7
<211> LENGTH: 4
<212> TYPE: PRT
<213> ORGANISM: Artificial Sequence
<220> FEATURE:
<223> OTHER INFORMATION: neurotrophic and/or neurogenic peptide

<400> SEQUENCE: 7

Val Gly Asp Gly
1

<210> SEQ ID NO 8
<211> LENGTH: 4
<212> TYPE: PRT
<213> ORGANISM: Artificial Sequence
<220> FEATURE:
<223> OTHER INFORMATION: neurotrophic and/or neurogenic peptide

<400> SEQUENCE: 8

Gly Asp Gly Gly
1

<210> SEQ ID NO 9
<211> LENGTH: 4
<212> TYPE: PRT
<213> ORGANISM: Artificial Sequence
<220> FEATURE:
<223> OTHER INFORMATION: neurotrophic and/or neurogenic peptide

<400> SEQUENCE: 9

Asp Gly Gly Leu
1

<210> SEQ ID NO 10
<211> LENGTH: 4
<212> TYPE: PRT
<213> ORGANISM: Artificial Sequence
<220> FEATURE:
<223> OTHER INFORMATION: neurotrophic and/or neurogenic peptide
```

```
<400> SEQUENCE: 10

Gly Gly Leu Phe
1

<210> SEQ ID NO 11
<211> LENGTH: 11
<212> TYPE: PRT
<213> ORGANISM: Artificial Sequence
<220> FEATURE:
<223> OTHER INFORMATION: neurotrophic and/or neurogenic peptide

<400> SEQUENCE: 11

Cys His Gln Gly Cys Gly Gly Leu Phe Glu Cys
1               5                   10

<210> SEQ ID NO 12
<211> LENGTH: 4
<212> TYPE: PRT
<213> ORGANISM: Artificial Sequence
<220> FEATURE:
<223> OTHER INFORMATION: exemplified with adamantyl-L-glycine

<400> SEQUENCE: 12

Asp Gly Gly Leu
1

<210> SEQ ID NO 13
<211> LENGTH: 4
<212> TYPE: PRT
<213> ORGANISM: Artificial Sequence
<220> FEATURE:
<223> OTHER INFORMATION: exemplified with adamantyl-L-glycine

<400> SEQUENCE: 13

Asp Gly Gly Leu
1

<210> SEQ ID NO 14
<211> LENGTH: 4
<212> TYPE: PRT
<213> ORGANISM: Artificial Sequence
<220> FEATURE:
<223> OTHER INFORMATION: Xaa at position 1 represents Glu or Asp, Xaa at
      position 2 represents any amino acid, Xaa at position 3 represents
      any amino acid and Xaa at position 4 represents Glu or Asp
<220> FEATURE:
<221> NAME/KEY: misc_feature
<222> LOCATION: (1)..(4)
<223> OTHER INFORMATION: Xaa can be any naturally occurring amino acid

<400> SEQUENCE: 14

Xaa Xaa Xaa Xaa
1

<210> SEQ ID NO 15
<211> LENGTH: 8
<212> TYPE: PRT
<213> ORGANISM: Artificial Sequence
<220> FEATURE:
<223> OTHER INFORMATION: neurotrophic and/or neurogenic peptide

<400> SEQUENCE: 15

Gly Gly Leu Phe Glu Lys Lys Leu
1               5
```

NEUROTROPHIC PEPTIDES

CROSS-REFERENCE TO RELATED APPLICATIONS

The present application is a continuation-in-part of Ser. No. 13/044,323, filed on Mar. 9, 2011, which is a continuation-in-part of U.S. patent application Ser. No. 12/531,616 filed Sep. 16, 2009, which is a national stage application of PCT/EP2008/002106, filed on Mar. 17, 2008, which claims priority to European Application No. 07450050.5 filed Mar. 16, 2007, all of which are hereby incorporated by reference in their entireties.

STATEMENT AS TO FEDERALLY SPONSORED RESEARCH

The invention was supported in part by National Institutes of Health grant AG 019158. The government has certain rights to the invention.

BACKGROUND OF THE INVENTION

1. Field of the Invention

The present invention relates to neurotrophic and/or neurogenic peptides and their use for manufacturing a medicament for the treatment of neurodegenerative diseases.

2. Description of the Related Art

The population in the industrialised countries is rapidly ageing due to a greater life expectancy, and an ever-increasing number of people are afflicted with neurodegenerative diseases making a global issue out of these diseases.

Neurodegenerative diseases result from the gradual and progressive loss of neural cells, leading to nervous system dysfunction, and may have next to ageing various causes (e.g. environmental influences, genetic defects). Until now, more than 600 neurologic disorders are known.

The major known risk factors for neurodegenerative disease include certain genetic polymorphisms and increasing age. Other possible causes may include gender, poor education, endocrine conditions, oxidative stress, inflammation, stroke, hypertension, diabetes, smoking, head trauma, depression, infection, tumors, vitamin deficiencies, immune and metabolic conditions, and chemical exposure. Because the pathogenesis of many of these diseases remains unknown, also the role of environmental factors in these diseases may be considered. An overview of neurodegenerative diseases can be found, for instance, in "Neurodegenerative Diseases: Neurobiology, Pathogenesis and Therapeutics" (M. Flint Beal, Anthony E. Lang, and Albert C. Ludolph; Cambridge University Press; 2005).

In order to treat neurodegenerative diseases several medicaments comprising one or more active compounds like Piracetam, Nimotop, Vinpocetin, Gliatilin, Cerebrolysin, Cytoflavin etc. are regularly employed. The compounds known in the art have varying modes of action. Cerebrolysin, for instance, a peptide based drug produced from purified animal brain proteins by standardized enzymatic breakdown, is exerting nerve growth factor like activity on neurons from dorsal root ganglia, neurotrophic and neuroprotective effects.

US 2004/102370 relates to peptides comprising the essential tetrameric peptide structural unit Xaa-Xaa-Xaa-Xaa (SEQ. ID. NO. 14) in which Xaa at position 1 represents Glu or Asp, Xaa at position 2 represents any amino acid, Xaa at position 3 represents any amino acid and Xaa at position 4 represents Glu or Asp. Said peptides are used to treat neurodegenerative diseases and nerve damages, and are described to be stimulators of axonal regeneration and survival.

Ciliary neurotrophic factor (CNTF) is a survival factor for various neuronal cell types. The human CNTF protein comprises 200 amino acid residues and shares significant sequence homology with CNTF proteins from other mammalian sources. The gene for human CNTF has been cloned and recombinant forms of the protein are available for clinical trials in humans (WO 91/04316). Over the past decade, a number of biological effects have been ascribed to CNTF in addition to its ability to support the survival of ciliary ganglion neurons. CNTF is believed to induce the differentiation of bipotential glial progenitor cells in the perinatal rat optic nerve and brain (Hughes et al., 1988, Nature 335:70-73). Furthermore, it has been observed to promote the survival of embryonic chick dorsal root ganglion sensory neurons (Skaper and Varon, 1986, Brain Res. 389:39-46). In addition, CNTF supports the survival and differentiation of motor neurons, hippocampal neurons and presympathetic spinal cord neurons (Sendtner, et al., 1990, Nature 345: 440-441).

In addition to human CNTF, the corresponding rat and rabbit genes have been cloned and found to encode a protein of 200 amino acids, which share about 80% sequence identity with the human gene.

Despite their structural and functional similarity, recombinant human and rat CNTF differ in several respects. The biological activity of recombinant rat CNTF in supporting survival and neurite outgrowth from embryonic chick ciliary neurons in culture is four times better than that of recombinant human CNTF (Masiakowski et al., 1991, J. Neurochem. 57:1003-1012). Further, rat CNTF has a higher affinity for the human CNTF receptor than does human CNTF.

As described in WO 99/43813 one of the uses of CNTF is the use of CNTF for the treatment of Huntington's disease. Huntington's disease (HD) is an hereditary degenerative disorder of the central nervous system.

However, the administration of CNTF to the human body has several drawbacks. While its therapeutic potential for CNS diseases is well recognized, the blood brain barrier (BBB) hinders the systemic delivery of CNTF and direct bolus injections are not suitable due to the short half-life of CNTF. One method of overcoming the blood brain barrier while providing continuous delivery of CNTF is, e.g., with immunoisolated cellular implants that produce and deliver CNTF directly to the region of interest. Cells can be protected from host rejection by encapsulating, or surrounding, them within an immunoisolatory, semipermeable membrane that admits oxygen and required nutrients and releases bioactive cell secretions, but restricts passage of larger cytotoxic agents from the host immune defense system. The selective membrane eliminates the need for chronic immunosuppression of the host and allows the implanted cells to be obtained from nonhuman sources. However, also this method is not advantageous.

BRIEF SUMMARY OF THE INVENTION

It is therefore a principal object and advantage of the present invention to provide new medicaments comprising substances which have substantially the same or even better neurotrophic and/or neurogenic effects than CNTF. Advantageously these substances should also be able to pass the blood brain barrier in order to reach the wanted site of action in the brain.

In accordance with the foregoing objects and advantages, the present invention provides a neurotrophic and/or neurogenic peptide having an amino acid sequence selected from the group consisting of VGDGGLFEKKL (SEQ ID NO: 1), EDQQVHFTPTEG (SEQ ID NO: 2) or IPENEADGMPATV (SEQ ID NO: 3).

It has surprisingly been found that the peptides of the present invention, which are derivable from rat or human CNTF, show neurotrophic and/or neurogenic (causing growth of nerve tissue) effects which are comparable to the wild-type CNTF. Furthermore due to their small size these peptides are also able to pass the blood brain barrier.

Fragments of SEQ ID NO: 1 to 3 preferably comprise 4 to 10, more preferably 4 to 8, even more preferably 4 to 6, amino acids and include:

| Source | Sequence | SEQ ID NO: |
|---|---|---|
| SEQ ID NO: 1 | GDGGLFEK | 5 |
| | GLFEKKLW | 6 |
| | VGDG | 7 |
| | GDGG | 8 |
| | DGGL | 9 |
| | GGLF | 10 |

The peptides of the present invention and their fragments may be fused to other proteins, polypeptides or peptides (N- or C-terminally), or conjugated to other substances. The resulting fusions may also comprise more than one peptide of the present invention (e.g. SEQ ID NO: 1 may be fused to SEQ ID NO: 2). The peptides of these polypeptides may be fused directly or via a linker to each other. Therefore, the present invention also relates to a polypeptide comprising at least two, preferably at least three, peptides of the present invention (SEQ ID NO: 1 to 10).

The peptides of the present invention may also be bound or conjugated to substances which enhance their ability to pass through the blood brain barrier.

"Fragments", as used herein, refer to parts of the peptides of the present invention, which are directly derivable from said peptides and show the same as or enhanced neurotrophic and neurogenic activities than the wild-type CNTF.

According to the present invention also peptides are encompassed which exhibit at least 80%, preferably 90%, more preferably 95%, identity with the peptides of the present invention selected from the group consisting of SEQ ID NO: 1 to 3.

According to the present invention "identity" ("identical") is determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. In general, sequences are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carillo et al. (1988) SIAM J Applied Math 48:1073).

Whether any two amino acid molecules have amino sequences that are at least, for example, 80%, 85%, 90%, 95%, 96%, 97%, 98% or 99% "identical", can be determined using known computer algorithms such as the "FAST A" program, using for example, the default parameters as in Pearson et al. (1988) PNAS USA 85: 2444 (other programs include the GCG program package (Devereux, J., et al., Nucleic Acids Research (1984) Nucleic Acids Res., 12, 387-395), BLASTP, BLASTN, FASTA (Atschul, S. F., et al., J Molec Biol 215: 403 (1990); Guide to Huge Computers, Martin J. Bishop, ed., Academic Press, San Diego, 1994, and Carillo et al, (1988) SIAM J Applied Math 48: 1073). For instance, the BLAST tool of the NCBI database can be used to determine identity. Other commercially or publicly available programs include DNAStar "MegAlign" program (Madison, Wis.) and the University of Wisconsin Genetics Computer Group (UWG) "Gap" program (Madison, Wis.)). Percent identity of proteins and/or peptides can be determined, for example, by comparing sequence information using a GAP computer program (e.g. Needleman et al., (1970) J. Mol. Biol. 48:443, as revised by Smith and Waterman (1981) Adv. Appl. Math. 2:482). Briefly, the GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and for non-identities) and the weighted comparison matrix of Gribskov et al. 14:6745, as described by Schwartz and Dayhoff, eds., ATLAS OF PROTEIN SEQUENCE AND STRUCTURE, National Biomedical Research Foundation, pp. 353-358 (1979); (2) a penalty of 3.0 for each gap and an additional 0.10 penalty for each symbol in each gap; and (3) no penalty for end gaps.

As used herein, the term "at least 80% identical to" refers to percent identities from 80 to 99.99 relative to the reference peptides. Consequently, the peptides of the present invention may also comprise one or more amino acid modifications (i.e. substitutions, deletions, insertions), provided that the peptides still exhibit neurotrophic and/or neurogenic activity.

Identity at a level of 80% or more is indicative of the fact that, assuming for exemplification purposes a test and reference polypeptide length of 100 amino acids is compared, no more than 20% (i.e. 20 out of 100) of amino acid residues in the test polypeptide differs from that of the reference polypeptide. Such differences can be represented as point mutations randomly distributed over the entire length of an amino acid sequence or they can be clustered in one or more locations of varying length up to the maximum allowable, e.g. 20/100 amino acid difference (approx. 80% identity). Differences are defined as amino acid substitutions, insertions or deletions. At the level of homologies or identities above about 85-90%, the result should be independent of the program and gap parameters set; such high levels of identity can be assessed readily, often without relying on software.

According to a preferred embodiment of the present invention the neurotrophic peptide of the present invention is identical to SEQ ID NO: 1, 2 or 3, which means that the neurotrophic peptide consists of said amino acids sequences or fragments thereof. Of course, the peptide of the present invention may comprise modifications such as substitution of L-amino acids with D-amino acids, introduction of hydrophobic side chains, modifications allowing the formation of dimers (or even multimers) or cyclic peptide variants. The respective methods are well known in the art.

The peptide according to the present invention is preferably non immunogenic. The term "non immunogenic peptide" as used herein refers to a molecule, in particular to a peptide, which does substantially not provoke an immune response in vivo when administered to a human or an animal being. This molecule property can be determined by methods known in the art. For instance, if the administration of a molecule according to the present invention to an animal (e.g. rabbit, mouse) provokes in an animal a substantial increase of antibodies directed against said molecule, said molecule is considered as an "immunogenic peptide", if, however, substantially no molecule-specific antibodies can be induced in an animal or human upon administration of said molecule, it is considered as a "non immunogenic peptide". It is important that the peptides according to the present invention are non immunogenic because immunogenic peptides are normally eliminated from the body by the immune system.

The basic structure of the peptide according to the present invention, which is formed by amino acids, is preferably synthesised chemically according to methods known in the art, e.g. by the method developed by Merrifield et al. (Merrifield, R. B. (1963) J. Am. Chem. Soc. 85, 2149-2154; solid phase peptide synthesis).

The solid phase peptide synthesis method introduced by Merrifield in 1963, for instance, involves the attachment of a growing peptide chain to a solid support. An amino acid corresponding to the C-terminal of the target peptide is covalently attached to an insoluble polymeric support (the "resin"). The next amino acid, with a protected alpha-amino acid, is activated and reacted with the resin-bound amino acid to yield an amino-protected dipeptide on the resin. The amino-protecting group is removed and chain extension is continued with the third and subsequent protected amino acids. After the target protected peptide chain has been built up the resin is cleaved by suitable chemical means thereby releasing the crude peptide product into solution (for solid phase peptide synthesis methods and other peptide synthesis methods see also Fields, G. B. (ed.), Solid Phase Peptide Synthesis in Methods in ENZYMOLOGY, Vol. 289, Academic Press, San Diego (1997); Bodansky, M., Bodansky, A., The practice of peptide synthesis (2nd edn.), Springer Verlag, Berlin (1995); Pennington, M. W., Dunn, B. M. (eds), Peptide Synthesis Protocols, in Methods in Molecular Biology, Vol. 35, Humana Press Inc., Totowa (1994); Grant, G. A. (ed.), Synthetic peptides: a user's guide, W.H. Freemann & Co., New York (1992)).

The inorganic cation at the C-terminal end of the peptide according to the present invention may be an alkali metal or alkali earth metal cation, preferably a lithium, sodium, potassium, magnesium or calcium cation.

These inorganic cations are regularly used to prepare salts of pharmaceutically active substances.

The organic cation may be a quaternary ammonium ion.

If the N-terminal end of the peptide according to the present invention comprises a positive charge, said charge may be preferably compensated by an equivalent of an inorganic or organic anion. The organic anion can be, for instance, acetate anion.

Of course it is also possible to use molecules, preferably small molecules, mimicking the peptides of the present invention.

Another aspect of the present invention relates to a pharmaceutical composition comprising at least one peptide according to the present invention and/or at least one peptide having an amino acid sequence selected from the group consisting of GDGGLFEK (SEQ ID NO: 5), GLFEKKLW (SEQ ID NO: 6), VGDG (SEQ ID NO: 7), GDGG (SEQ ID NO: 8), DGGL (SEQ ID NO: 9) and GGLF (SEQ ID NO: 10) and optionally at least one pharmaceutically acceptable excipient and/or carrier.

The peptide according to the present invention may be formulated in a pharmaceutical preparation, which can be administered to a patient for preventing or treating a cerebral disease, in particular, a neurodegenerative disease. The pharmaceutical preparation may further comprise pharmaceutically acceptable excipients and/or carriers. Suitable excipients and carriers are well known in the art (see e.g. "Handbook of Pharmaceutical Excipients", 5th Edition by Raymond C. Rowe, Paul J. Sheskey, Sian C. Owen (2005), APhA Publications).

The composition of the present invention may further comprise at least one additional pharmaceutically active component, which is preferably IPRNEADGMPINV (SEQ ID NO: 4).

The pharmaceutical preparation according to the present invention may comprise, in addition to the peptide according to the present invention, further active components, which may exhibit similar properties when administered to an individual or which may cause other reactions in the treated patient.

According to the present invention, e.g., antioxidants like vitamins may be considered as further active components because antioxidants inhibit oxidation or suppress reactions promoted by oxygen, oxygen free radicals, oxygen reactive species including peroxides. Antioxidants, especially lipid-soluble antioxidants, can be absorbed into the cell membrane to neutralize oxygen radicals and thereby protect the membrane. The antioxidants useful in the present invention are preferably vitamin antioxidants that may be selected from the group consisting of all forms of Vitamin A including retinal and 3,4-didehydroretinal, all forms of carotene such as alpha-carotene, beta-carotene, gamma carotene, delta-carotene, all forms of Vitamin C (D-ascorbic acid, L-ascorbic acid), all forms of tocopherol such as Vitamin E (Alpha-tocopherol, 3,4-dihydro-2,5,7,8-tetramethyl-2-(4,8,12-trimethyltri-decyl)-2H-1-benzopyran-6-ol), beta-tocopherol, gamma-tocopherol, delta-tocopherol, tocoquinone, tocotrienol and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof.

According to another preferred embodiment of the present invention the composition is provided for intravenous, intramuscular, spinal, epidural, transdermal, intranasal, mucosal, parenteral, oral, enteral or rectal administration.

Depending on the route of administration the pharmaceutical composition according to the present invention may be formulated, for instance, as tablets, capsules, liquids, infusion and suppositories (see e.g. "Pharmaceutical Formulation Development of Compounds" by Sven Frokjaer (1999), CRC; "Handbook of Pharmaceutical Manufacturing Formulations" by Sarfaraz K. Niazi (2004), CRC).

The peptides are preferably comprised in the composition in an amount between 0.1 µg/g to 100 mg/g, preferably 1 µg/g to 80 mg/g. In any way, the effective dosages for prevention or treatment of human patients can be optimised for given patients or patient collectives according to the routine methods available for the present field.

Another aspect of the present invention relates to the use of at least one peptide with neurotrophic and/or neurogenic activity, as defined above, which may be part of a molecule consisting of a maximum of 50, preferably a maximum of 40, more preferred a maximum of 30, even more preferred a maximum of 20, amino acids, and/or at least one peptide having an amino acid sequence selected from the group consisting of G-D-G-G-L-F-E-K (SEQ ID NO: 5), G-L-F-E-K-K-L-W (SEQ ID NO: 6), V-G-D-G (SEQ ID NO: 7), G-D-G-G (SEQ ID NO: 8), D-G-G-L (SEQ ID NO: 9) and G-G-L-F (SEQ ID NO: 10) for the manufacture of a medicament for the treatment and/or prevention of a neurodegenerative disease.

According to the present invention all peptides disclosed herein and exhibiting neurotrophic and/or neurogenic activity may be used for manufacturing a medicament for the treatment and/or prevention of neurodegenerative diseases.

According to a preferred embodiment of the present invention the peptide is a peptide according to the present invention as defined above.

The neurodegenerative disease is preferably selected from the group consisting of Alexander disease, Alper's disease, Alzheimer disease, Amyotrophic lateral sclerosis, Ataxia telangiectasia, Canavan disease, Cockayne syndrome, Corticobasal degeneration, Creutzfeldt-Jakob disease, epilepsy, Huntington disease, Kennedy's disease, Krabbe disease, Lewy body dementia, Machado-Joseph disease (Spinocerebellar ataxia type 3), Multiple sclerosis, Multiple System Atrophy, Parkinson disease, Pelizaeus-Merzbacher Disease, Pick's disease, Primary lateral sclerosis, Refsum's disease, Sandhoff disease, Schilder's disease, Spinocerebellar ataxia, Steele-Richardson-Olszewski disease, stroke, depression and Tabes dorsalis.

Next to these preferred neurodegenerative diseases the peptide according to the present invention may also be used to treat other cerebral disorders.

In one embodiment of the invention a peptide or protein comprising or consisting of a peptide of the present invention can be employed as a drug stimulating cerebral reparative process and used for the treatment and prevention of trauma-associated cerebral lesions, including the treatment of cerebral lesions after a fracture of the cranial vault, skull base, multiple bone fractures, the treatment for the cerebral lesions in cases of intracranial trauma (e.g. posttraumatic cerebral concussion, cerebral wounds and contusion, subarachnoid, subdural and extradural haemorrhage), the treatment and prevention of traumatic shock, the treatment of the cerebral lesions associated with the impact of radiation, lowered temperature, heat and light, air pressure, electric and ultrahigh frequency current, the treatment and prevention of delayed-onset effects of skull fractures, the treatment and prevention of delayed-onset effects of intral cranial trauma, the treatment and prevention of delayed-onset cerebral lesions induced by radiation, complications after surgical and other medical interventions.

In another embodiment of the present invention the peptides according to the present invention may be used as a drug suppressing toxic effects of the neurotrophic agents, stimulating cerebral repair processes and revealing cerebroprotective activity for the treatment and prevention of cerebral lesions after poisoning including the treatment of cerebral lesions after poisoning with therapeutic agents, medicinal and biological compounds, the treatment of the cerebral impairment with agents of non-medical origin, the treatment and prevention of delayed-onset cerebral lesions induced by poisoning with drugs and nonmedical substances.

In another embodiment of the present invention the peptides according to the present invention may be used as drug with nootropic activity and stimulating cerebral repair processes for the treatment and prevention of mental deficiencies.

In another embodiment of the present invention the peptides according to the present invention may be used for stimulating cerebral repair processes and motional activity for the treatment and prevention of paralytic disorders including the treatment and prevention of hemiplegia, the treatment and prevention of infantile cerebral paralysis, the treatment and prevention of other paralytic syndromes (quadriplegia, paraplegia, diplegia of upper extremities, monoplegia of lower extremities).

In another embodiment of the present invention the peptides according to the present invention may be used as drug stimulating cerebral repair processes with cerebroprotective activity for the treatment and prevention of cerebral impairments in case of chromosome anomalies including Downs syndrome.

In another embodiment of the present invention the peptides according to the present invention may be used as drug stimulating cerebral repair processes with cerebroprotective activity for the treatment and prevention of cerebral impairments in case of inflammatory cerebral disorders including the treatment and prevention of cerebral impairments in case of bacterial meningitis including cryptococcus meningitis in AIDS patients, the treatment and prevention of cerebral impairments in case of nonbacterial meningitis, the treatment and prevention of cerebral impairments in case of meningitis of unclear origin, the treatment and prevention of cerebral impairments in case of encephalitis, myelitis and encephalomyelitis, including cerebral toxoplasmosis in AIDS patients, for the treatment and prevention of cerebral impairments in case of intracranial abscesses, for the treatment and prevention of cerebral impairments in case of phlebitis and thrombophlebitis of intracranial venous sinus, for the treatment and prevention of sequalae after intracranial abscesses or purulent infection.

In another embodiment of the present invention the peptides according to the present invention may be used as drug stimulating cerebral repair processes with cerebroprotective and nootropic activity for the treatment and prevention of cerebral impairments in case of cerebral-vascular disorders including the treatment and prevention of cerebral impairments in case of subarachnoid haemorrhage, treatment and prevention of cerebral impairments in case of cerebral haemorrhage, the treatment and prevention of cerebral impairments in case of occlusion and Stenosis of precerebral arteries, the treatment and prevention of cerebral impairments in case of occlusion of cerebral arteries, the treatment and prevention of cerebral impairments in case of transitory cerebral ischemia, the treatment and prevention of cerebral impairments in case of other cerebral-vascular disorders (acute cerebral-vascular disorders, cerebral atherosclerosis and other generalised cerebral-vascular disorders, hypertension encephalopathy, cerebral aneurysm, cerebral arteritis and non-purulent thrombosis of intracranial venous sinus).

In another embodiment of the present invention the peptides according to the present invention may be used as drug stimulating cerebral repair processes, having cerebroprotective and nootropic activity for the treatment and prevention of alcoholic psychosis including the treatment and prevention of delirium tremens at abstinence syndrome, the treatment and prevention of alcoholic amnestic syndrome and other alcoholic dementia disorders, the treatment and prevention of pathologic alcoholic intoxication, the treatment and prevention of alcoholic paranoia and alcoholic psychosis of paranoid type.

In another embodiment of the present invention the peptides according to the present invention may be used as drug stimulating cerebral repair processes, having cerebroprotective and nootropic activity for the treatment and prevention of cerebral impairment in case of alcoholism.

In another embodiment of the present invention the peptides according to the present invention may be used as a drug suppressing toxic effects of neurotropic agents and having cerebro-protective and nootropic activity for the treatment and prevention of drug-induced psychosis including the treatment and prevention of the drug abstinence syndrome, the treatment and prevention of drug-induced paranoid and/or hallucinatory disorders, the treatment and prevention of pathologic intoxication with medical agents, the treatment and prevention of other drug-induced psychic disorders (delirium, dementia, amnestic syndrome and organic affective syndrome).

In another embodiment of the present invention the peptides according to the present invention may be used as a drug sup-pressing toxic effects of neurotropic agents and having cerebro-protective activity for the treatment and prevention of drug addiction including the treatment and prevention of addiction to opioid agents, the treatment and prevention of addiction to barbiturate, sedative agents and tranquillisers, the treatment and prevention of cocaine addiction, the treatment and prevention of addiction to *cannabis* and derivatives thereof, the treatment and prevention of addiction to amphetamine and psychostimulating agents, the treatment and prevention of addiction to hallucinogenic agents, treatment and prevention of cerebral impairments caused by drug abuse without drug addiction (abuse of alcohol, tobacco, *cannabis*, hallucinogens, opioids, cocaine, psychostimulating agents, antidepressants).

In another embodiment of the present invention the peptides according to the present invention may be used as an agent for treatment and prevention of psychogenic symptoms and syndromes including the treatment and prevention of psychogenic physiologic impairments, the treatment and prevention of other psychogenic symptoms and syndromes (stammering and impediments, psychogenic anorexia tics, repeated stereotype movements, inorganic sleep disorders, psychogenic diet disorders, enuresis, psychalgia), the treatment and prevention of acute stress response, the treatment and prevention of reactions induced by psychological directions.

In another embodiment of the present invention the peptides according to the present invention may be used as an agent for treatment and prevention of inorganic psychoses including the treatment and prevention of Schizophrenie disorders, the treatment and prevention of affective psychoses, the treatment and prevention of paranoid conditions, the treatment and prevention of other inorganic psychoses (psychoses of depressive and agitate types, reactive confusion, acute paranoid reactions, psychogenic paranoid psychoses) and non-differentiated psychoses including psychoses induced with cerebral impairments in AIDS patients, the treatment and prevention of infantile psychoses including infantile autism and disintegrative psychoses.

In another embodiment of the present invention the peptides according to the present invention may be used as a drug stimulating cerebral repair processes and having cerebroprotective and nootropic activity for the treatment and prevention of cerebral impairments in case of other cerebral disorders including the treatment and prevention of cerebral impairments in case of cerebral cysts, the treatment and prevention of hypoxic cerebral damage, the treatment and prevention of cerebral impairments in case of intracranial hypertension, the treatment and prevention of cerebral impairments in case of encephalopathy.

In another embodiment of the present invention the peptides according to the present invention may be used as drug stimulating cerebral repair processes and motional activity, having cerebroprotective and nootropic effects for treatment and prevention of symptoms and syndromes in case of various cerebral disorders including the treatment and prevention of cognitive disorders, memory and artention, impairments (for instance, in case of amnestic diseases, mental deficiency, inorganic psychoses, etc.), the treatment and prevention of aphasia and apraxia (for instance, in case of amnestic diseases, inorganic psychoses, cerebral impairments due to chromosome anomalies, etc.), the treatment and prevention of emotional disorders (for instance, in case of inorganic psychoses, demyelinising cerebral disorders, etc.), the treatment and prevention of psychopathologic syndrome (for instance, in case of transitional organic psychotic conditions, drug-induced psychoses, drug addiction, etc.), the treatment and prevention of asthenic-depressive syndrome (for instance, in case of inorganic psychoses, cerebral impairments due to chromosome anomalies, etc.), the treatment and prevention of delirium syndrome (for instance, in case of drug-induced psychoses and drug addiction, inorganic psychoses, etc.), the treatment and prevention of sleep disorders (for instance, in case of cerebral tumours, transitional organic psychotic conditions, etc.), for treatment and prevention of cerebral-focal syndrome (focal pathologic symptoms) (for instance, in case of cerebral impairments caused by complications of surgical or other medical intervention, demyelinising cerebral disorders, etc.), the treatment and prevention of syndrome of motor disorders (for instance, in case of cerebral tumours, cerebral impairments caused by poisoning, etc.), the treatment and prevention of peripheral neuropathy, preferably diabetic neuropathy.

According to a preferred embodiment of the present invention the medicament further comprises a pharmaceutical acceptable excipient and/or carrier as defined above.

According to another preferred embodiment of the present invention the composition further comprises at least one additional pharmaceutically active component.

The medicament is preferably provided for intravenous, intramuscular, spinal, epidural, transdermal, subcutaneous, intranasal, mucosal, parenteral, oral, enteral or rectal administration.

According to a preferred embodiment of the present invention the medicament comprises the peptide in an amount between 0.1 µg/g to 100 mg/g, preferably 1 µg/g to 80 mg/g.

It is in particular preferred to use as peptide in a medicament of the present invention a peptide having the amino acid sequence SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and/or SEQ ID NO: 10.

Another aspect of the present invention relates to a method for preventing a break out of a neurodegenerative disease in an individual and for treating an individual suffering from a neurodegenerative disease comprising the administration of a pharmaceutical composition or of an effective amount of at least one peptide according to the present invention.

The term "effective amount" of a peptide as used herein will depend among other factors on the route of administration and physical condition of the individual to be exposed to said peptide. Methods for the determination of the effective amount are known to the skilled person.

The neurodegenerative disease is preferably selected from the group consisting of Alexander disease, Alper's disease, Alzheimer disease, Amyotrophic lateral sclerosis, Ataxia telangiectasia, Canavan disease, Cockayne syndrome, Corticobasal degeneration, Creutzfeldt-Jakob disease, epilepsy, Huntington disease, Kennedy's disease, Krabbe disease, Lewy body dementia, Machado-Joseph disease (Spinocerebellar ataxia type 3), Multiple sclerosis, Multiple System Atrophy, Parkinson disease, Pelizaeus-Merzbacher Disease, Pick's disease, Primary lateral sclerosis, Refsum's disease, Sandhoff disease, Schilder's disease, Spinocerebellar ataxia, Steele-Richardson-Olszewski disease, peripheral neuropathy, diabetic neuropathy, stroke, depression and Tabes dorsalis.

According to a preferred embodiment of the present invention the peptide is administered to said individual at a dose of 0.1 µg/kg to 20 mg/kg body weight, preferably 0.5 µg/kg to 10 mg/kg body weight.

Another aspect of the present invention relates to the use of at least one peptide with neurotrophic and/or neurogenic activity and/or at least one peptide having an amino acid sequence selected from the group consisting of G-D-G-G-L-F-E-K (SEQ ID NO: 5), G-L-F-E-K-K-L-W (SEQ ID NO: 6), V-G-D-G (SEQ ID NO: 7), G-D-G-G (SEQ ID NO: 8), D-G-G-L (SEQ ID NO: 9) and G-G-L-F (SEQ ID NO: 10) for the manufacture of a medicament for improving learning memory capacities in an individual.

Another aspect of the present invention relates to the use of a molecule consisting of a maximum of 50 amino acids with neurotrophic and/or neurogenic activity comprising at least one peptide according to the present invention or IPR-NEADGMPINV (SEQ ID NO: 4) or a fragment thereof for the manufacture of a medicament for the treatment or enhancement of motor deficiencies in an individual.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 5:
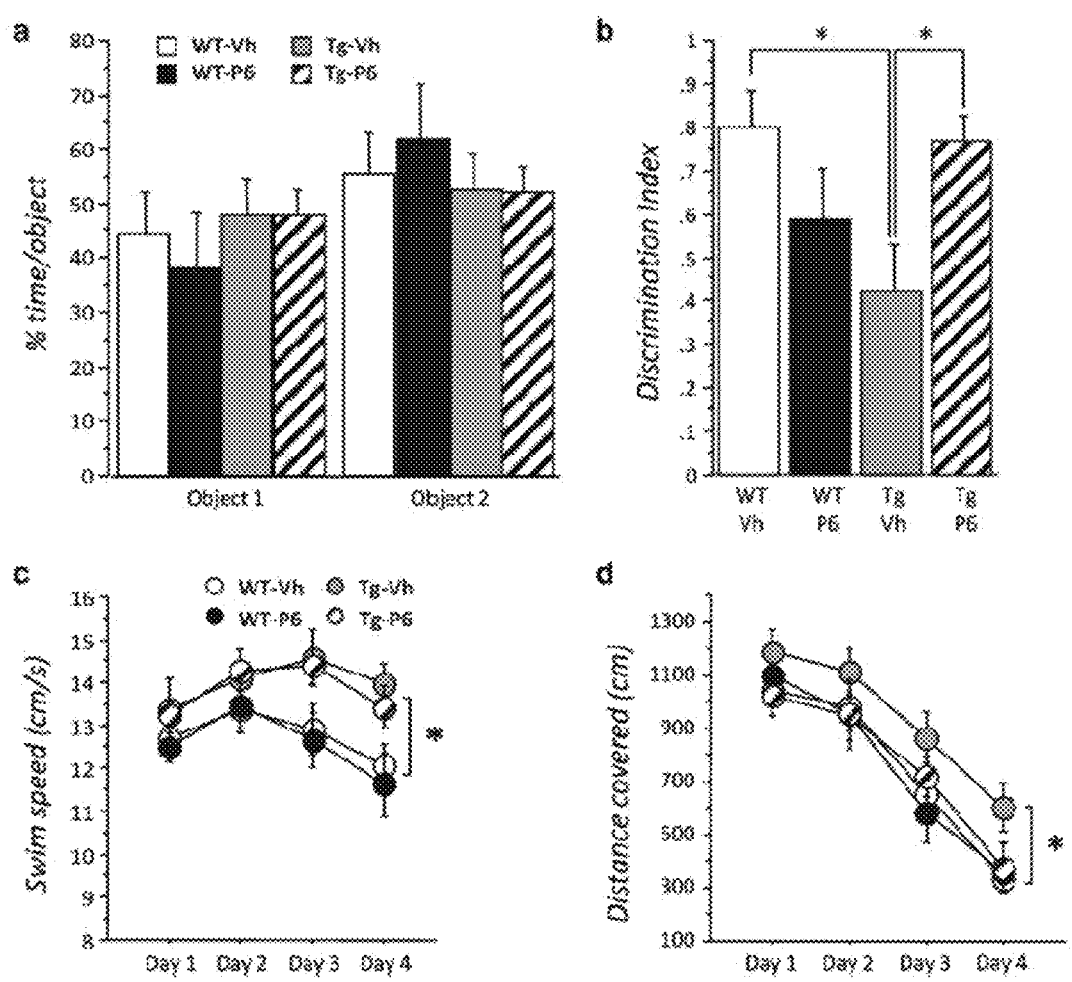

FIG. 5 is a series of graphs showing the rescue of cognitive impairments through treatment with Peptide 6, where (a) shows that in the sample phase of the one-trial object recognition task, all animal groups similarly explored both objects; (b) shows that in the test phase of the one-trial object recognition task, 3xTg-AD mice similarly explored the familiar and the new object (discrimination index 0.5), reflecting an impairment of discrimination, and treatment with Peptide 6 reversed this impairment; (c) shows that in the spatial reference memory task, 3xTg-AD mice swam faster than WT controls, and treatment with Peptide 6 did not have any effect on velocity; and (d) shows that during the training of the spatial reference memory task, performance of 3xTg-AD mice was delayed compared to WT controls, but treatment with Peptide 6 reversed this impairment ($*p<0.050$).

Figure 6:
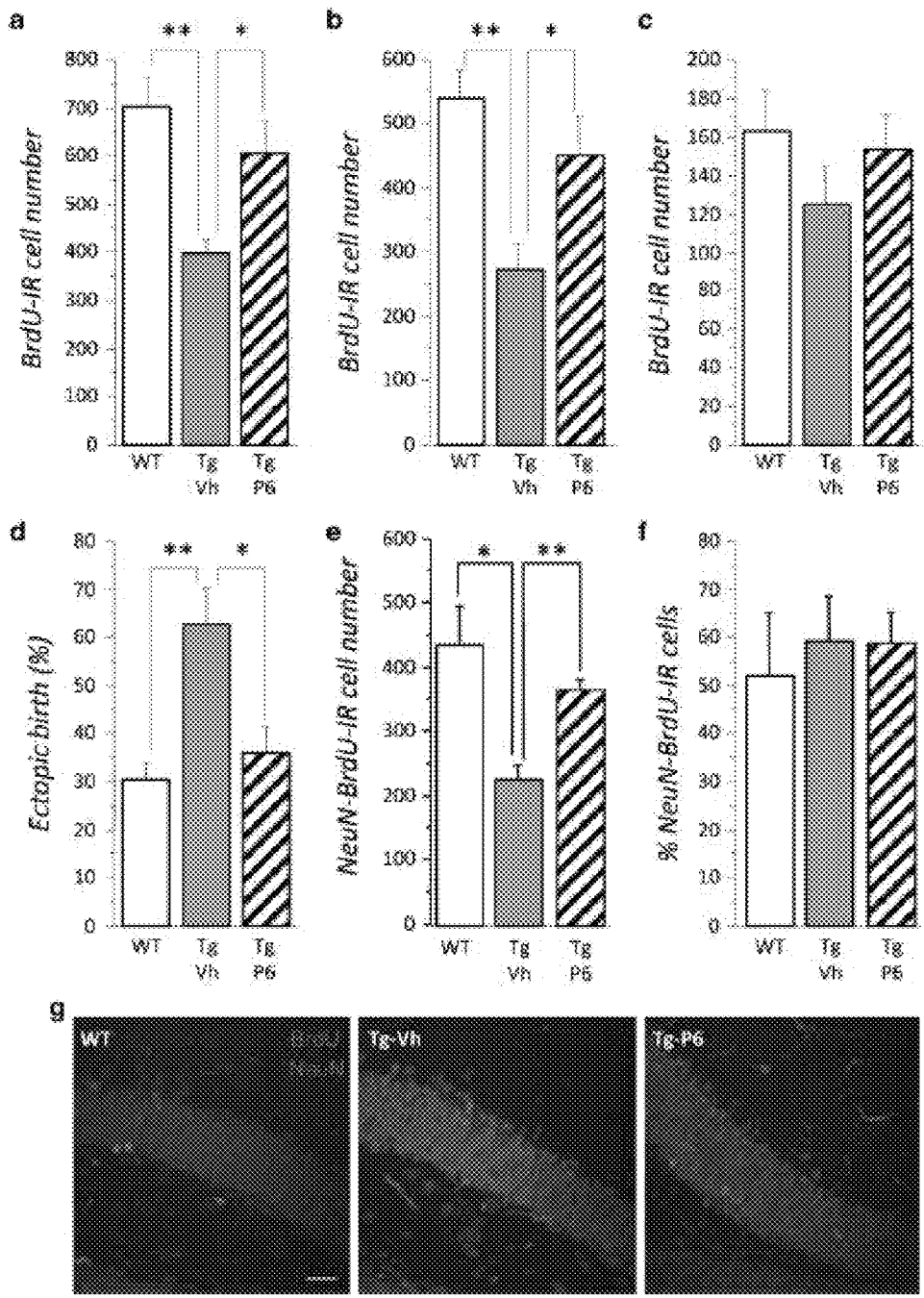

FIG. 6 is a series of graphs showing that treatment with Peptide 6 rescued neurogenic abnormalities in 3xTg-AD mice, where in the subgranular zone (SGZ) (a) and in the inner granular cell level (iGCL) (b) of the DG, the pool of new born cells in the DG was significantly reduced in 3xTg-AD mice, but treatment with Peptide 6 restored the number of BrdU-IR cells to WT control levels; in the outer granule cell layer (oGCL) (c) of the DG, no difference in the number of BrdU-IR cells was observed among groups; (d) shows that in the SGZ, ectopic birth was increased in 3xTg-AD mice, but treatment with Peptide 6 restored this abnormality; (e) shows that in the SGZ, the number of BrdU-NeuN-IR cells, i.e. net neurogenesis, was significantly reduced in 3xTg-AD mice, but treatment with Peptide 6 restored it to WT controls levels; (f) shows that the proportion of BrdU-IR cells expressing NeuN in the SGZ was similar in all groups, suggesting no change in the neuronal commitment of the progenitor cells; and (g) shows photomicrographs illustrating the ectopic birth abnormality in 3xTg-AD mice (scale bar 20 µm; $*p<0.050$, $**p<0.010$).

Figure 7:
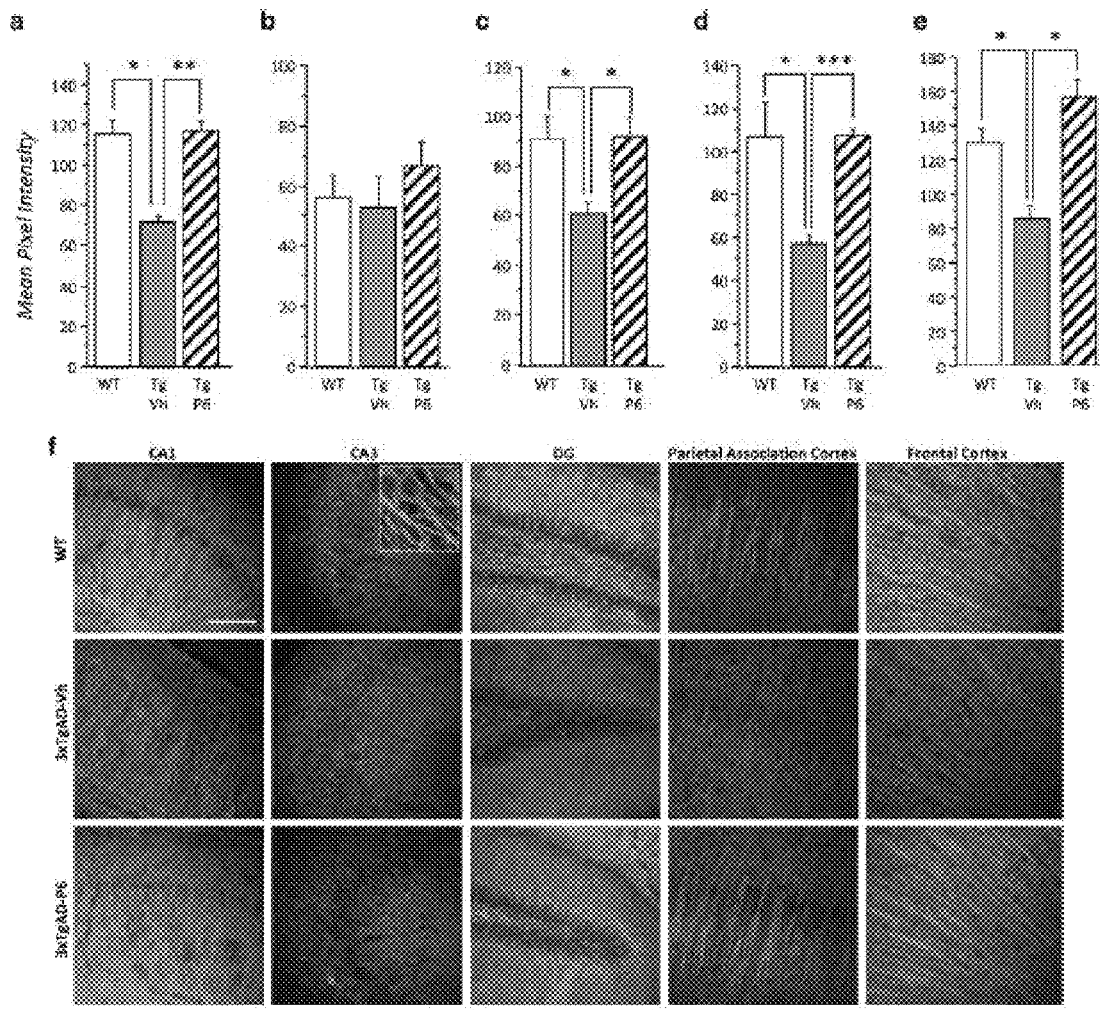

FIG. 7 is a series of graphs showing that treatment with Peptide 6 prevented the loss of dendritic density in 3xTg-AD mice, where 3xTg-AD mice displayed reduced MAP2 density in the CA1 (a) and the DG (b) of the hippocampus and in the parietal association (d) and frontal (e) cortices which were restored to WT controls levels by treatment with Peptide 6 and no significant difference in MAP2 immunoreactivity was observed in the CA3 of the hippocampus (b), and (f) shows photomicrographs illustrating MAP2 immunoreactivity in the different brain areas studied (scale bar 100 µm; $*p<0.050$, $p<0.010$, $*p<0.001$).

Figure 8:
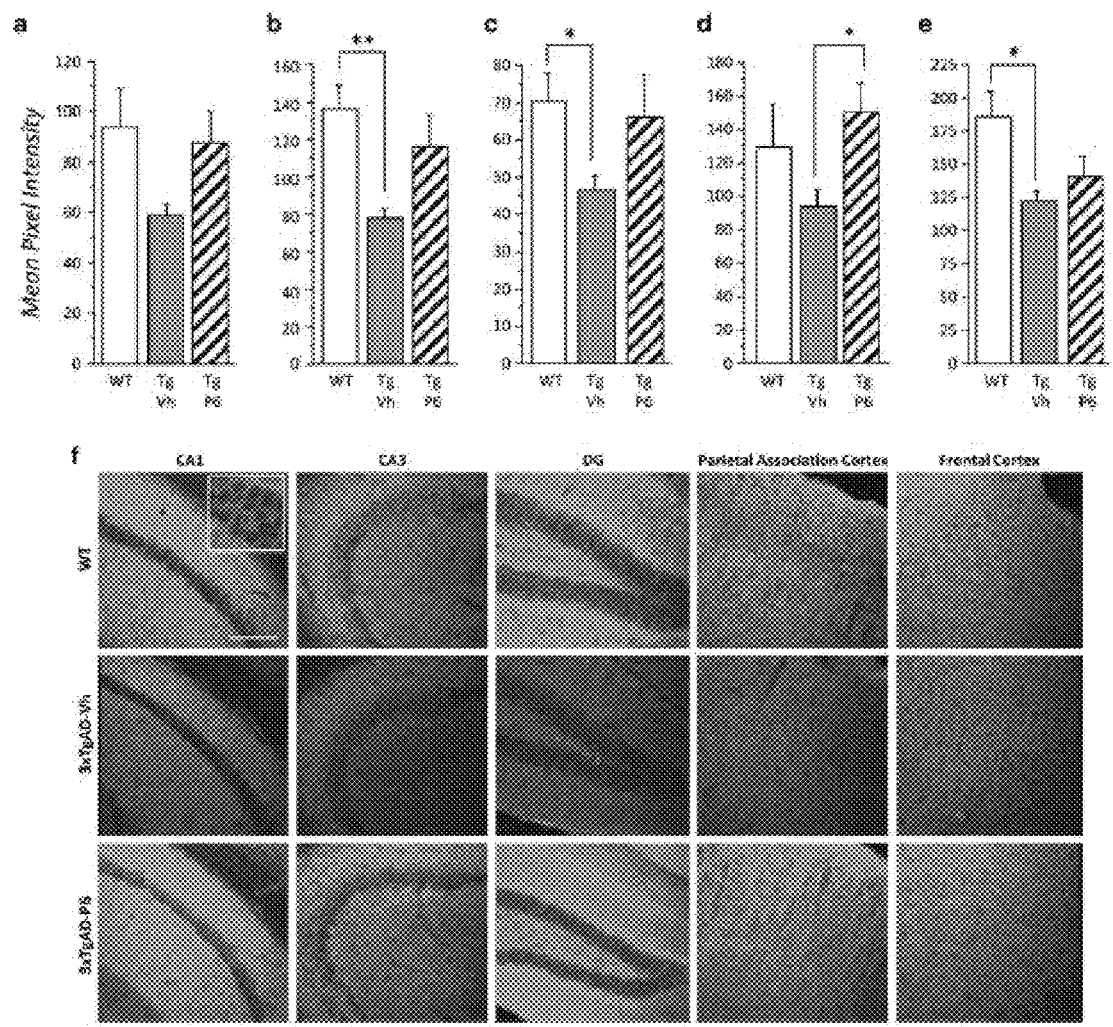

FIG. 8 is a series of graphs showing that treatment with Peptide 6 prevented synaptic loss in 3xTg-AD mice, where 3xTg-AD mice displayed significantly reduced synaptophysin density in the CA3 (b) and the DG (c) of the hippocampus and in the frontal cortex (e), there was also a tendency for reduced density of synaptophysin in the CA1 of the hippocampus (a) and in the parietal association cortex (d) in 3xTg-AD mice, treatment with Peptide 6 restored synaptophysin densities to WT control levels since no significant difference was observed between WT controls and 3xTg-AD mice treated with Peptide 6 in the brain areas studied, and (f) shows photomicrographs illustrating synaptophysin immunoreactivity in the different brain areas studied. Scale bar 100 µm ($*p<0.050$, $**p<0.010$).

Figure 9:
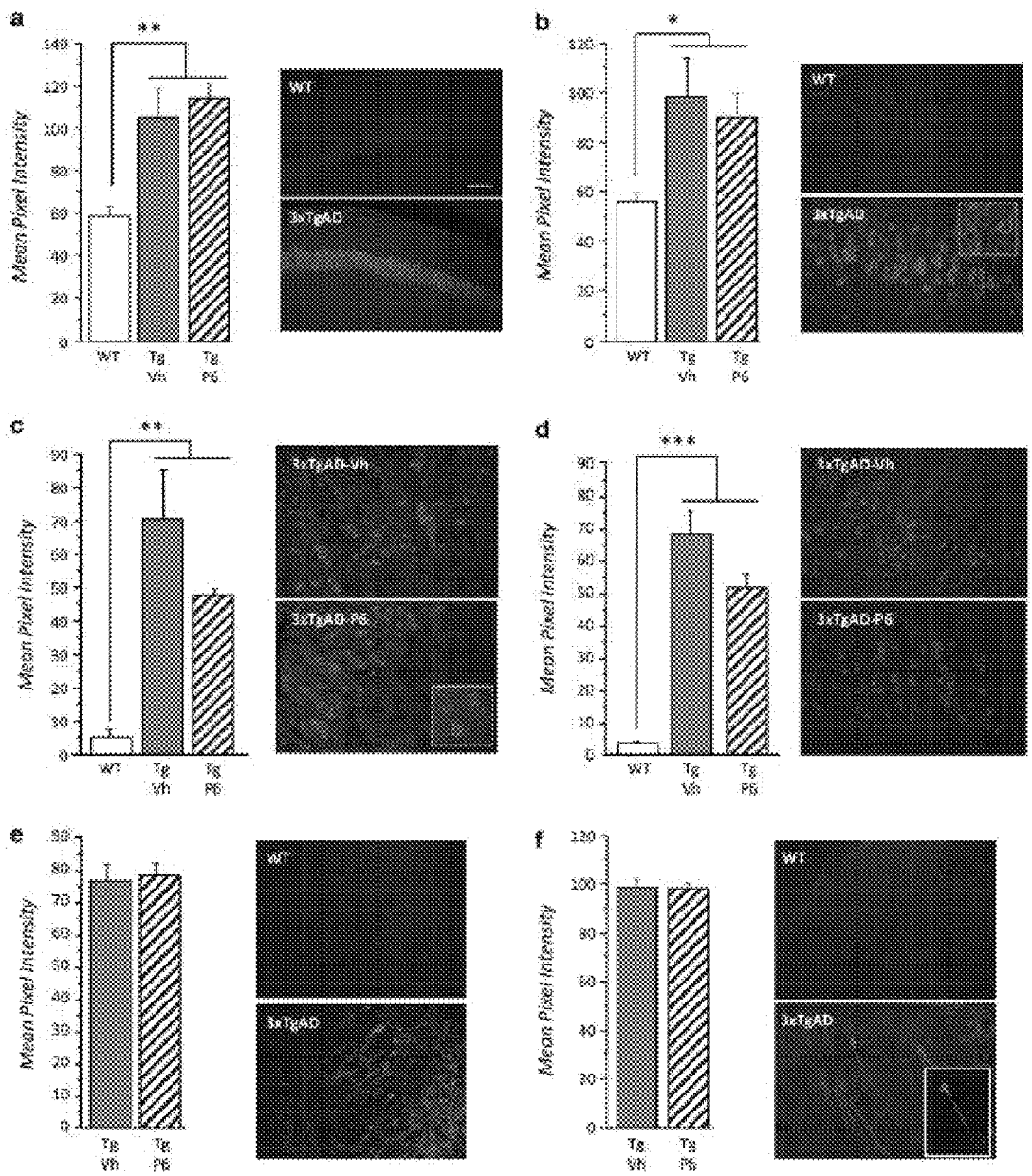

FIG. 9 is a series of graph showing treatment with Peptide 6 did not have any significant effect on Ab and tau pathologies, where in the CA1 of the hippocampus (a) and in parietal association cortex (b), 4G8 (Ab, bAPP) immunoreactivity was significantly increased in 3xTg-AD mice, and no effect of Peptide 6 was observed, in the frontal (c) and parietal association (d) cortices, Ab1-40 immunoreactivity was significantly increased in 3xTg-AD mice, but treatment with Peptide 6 had no significant effect, in the subiculum (e) and the CA1 of the hippocampus (f), AT8 (tau pSer202, pThr 205) immunoreactivity was similar in 3xTg-AD mice treated with Peptide 6 and vehicle, and WT animals showed only background staining (scale bar 20 µm. $*p<0.050$, $p<0.010$, $*p<0.001$).

Figure 10:
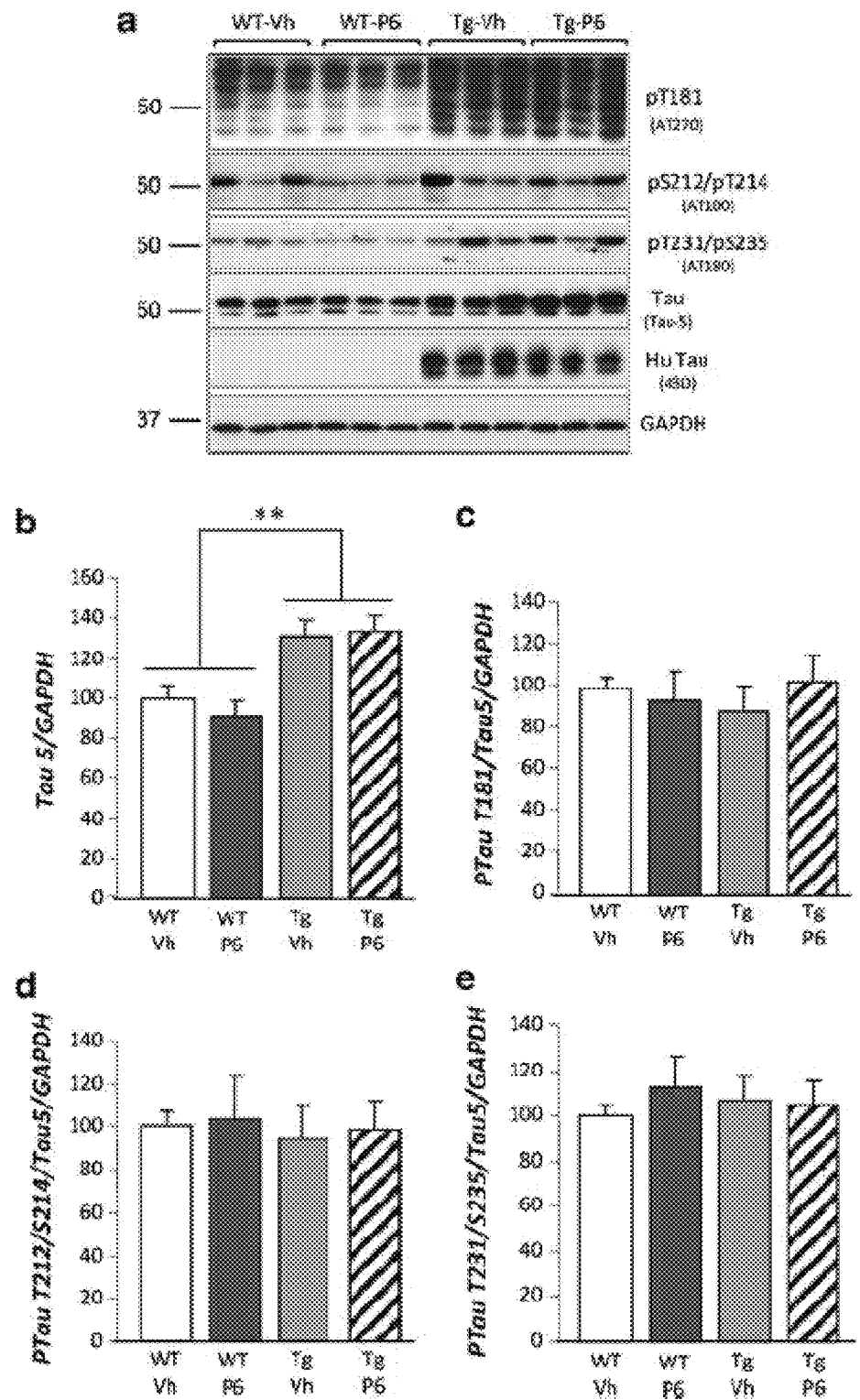

FIG. 10 is a series of graphs showing that treatment with Peptide 6 had no significant effect on abnormal hyperphosphorylation of tau, where (a) shows representative Western blots from three animals from each group and the blots were developed with human specific tau antibody 43D showed the protein expression only in 3xTg-AD mice, and quantification of blots showed (b) increase in expression of tau normalized with GAPDH blots as loading control in 3xTg-AD mice, but no significant effect on hyperphosphorylation of tau at (c) pTh181, (d) pThr212/pSer214, or (e) pThr231/pSer235, and the quantification of Western blots shown as mean±SEM from, WT-Vh, n=7; WT-P6, n=8; Tg-Vh, n=10; and Tg-P6, n=11.

FIG. 11(a) shows the experimental design of example 4; (b) and (c) show the proliferation of progenitors in four sub-regions of the hippocampus (for anatomical definitions, see "Materials and Methods" section): iGCL (inner granule cell layer, which included the SGZ), oGCL (outer granule cell layer), Mol (molecular layer) and Hil (hilus), revealed that compared to control group, CNTF 6c increased the number of BrdU-IR cells in the iGCL by 45% (p<0.001, Student's t-test), whereas no significant differences were observed in either oGCL, Mol or Hil.

Figure 12:
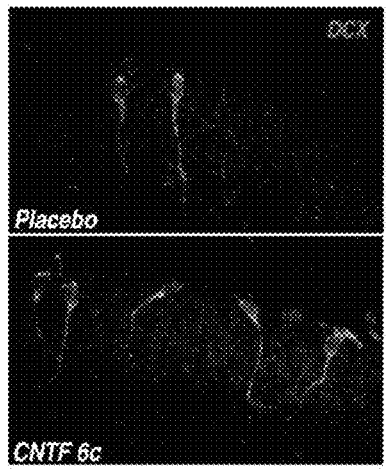
Figure 12:
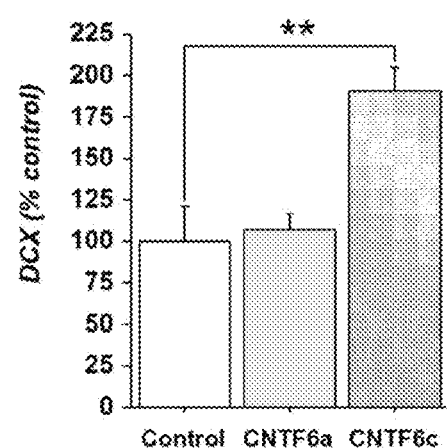
Figure 12:
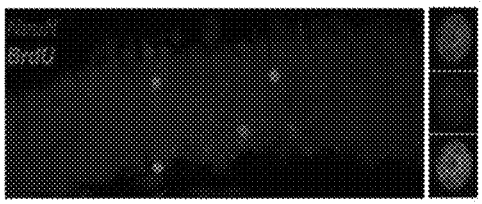
Figure 12:
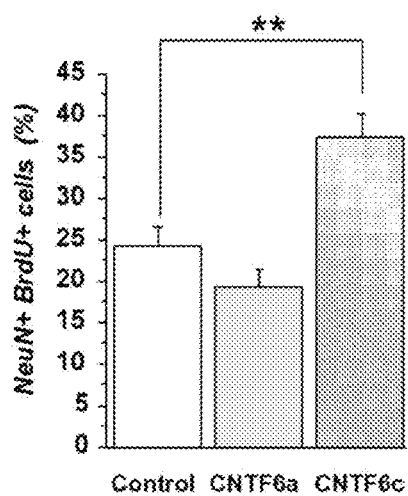

FIG. 12 shows the proliferation of immature neurons in the dentate gyrus (a) and the neuronal differentiation of progenitor cells in the dentate gyrus (b).

Figure 13:
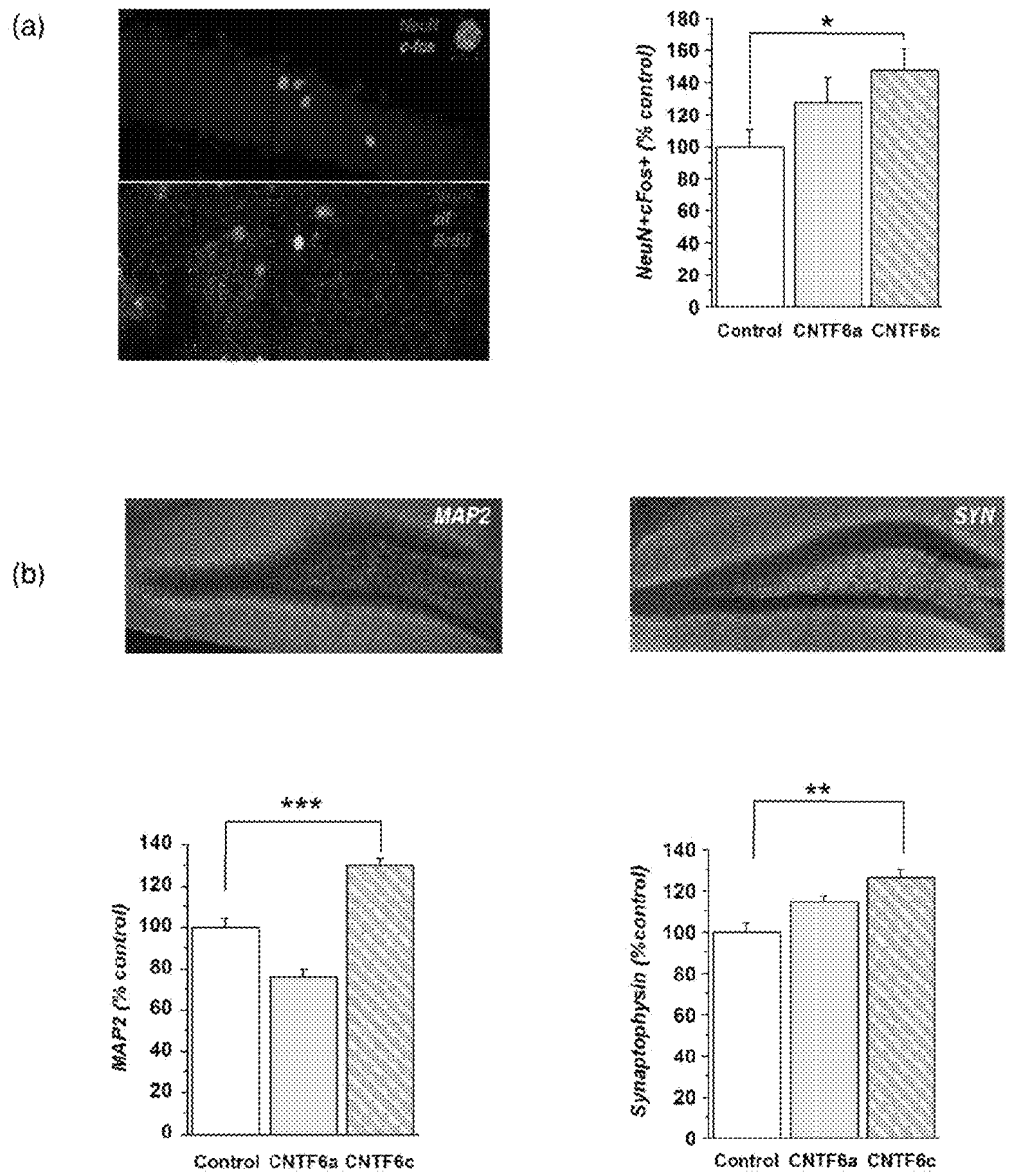

FIG. 13 shows the induction of immediate-early gene expression in resident neurons (a) and neurotrophy and neuroprotection in the dentate gyrus.

Figure 14:
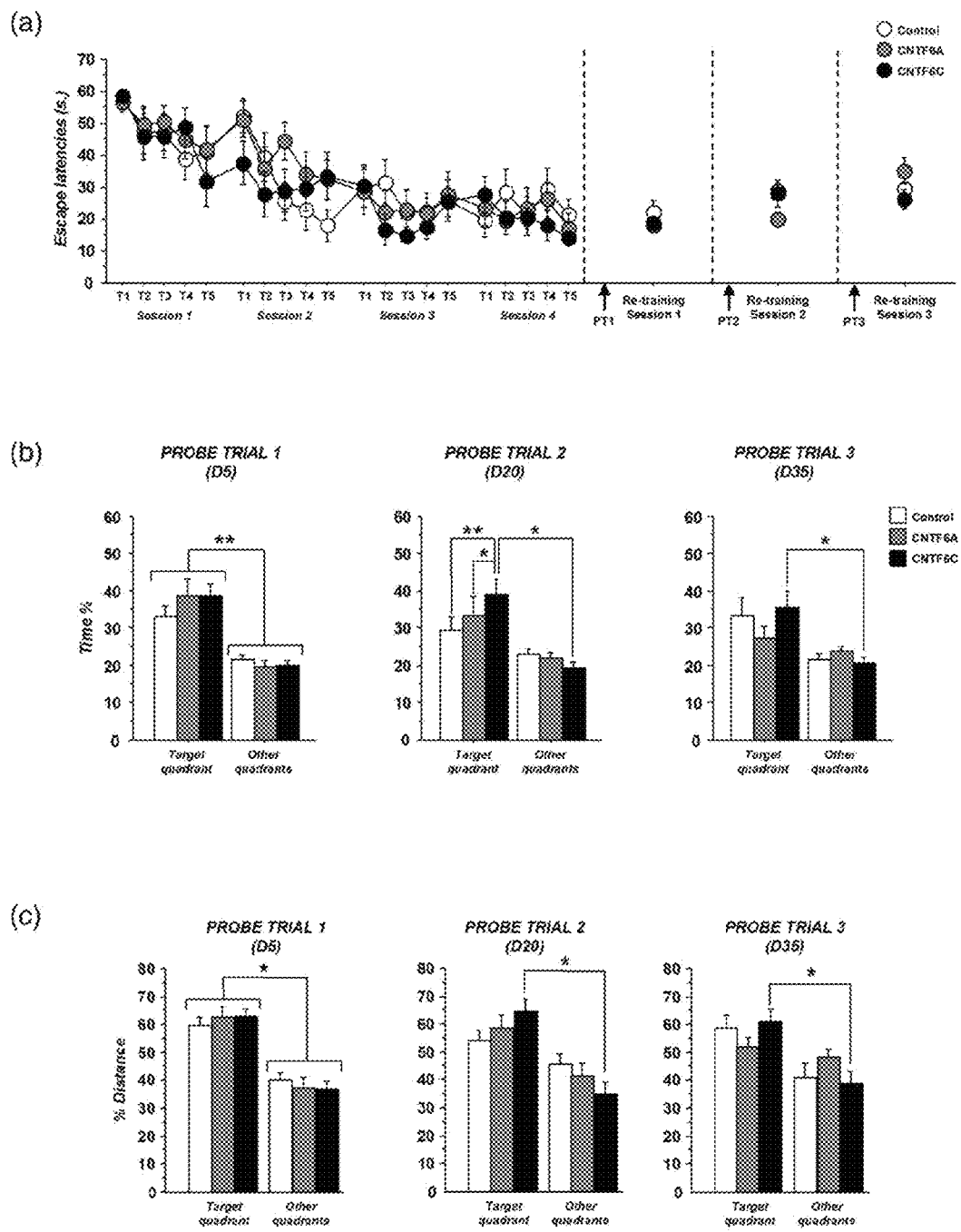

FIG. 14 shows the enhancement of memory by the administration of CNTF 6a and c.

Figure 15:
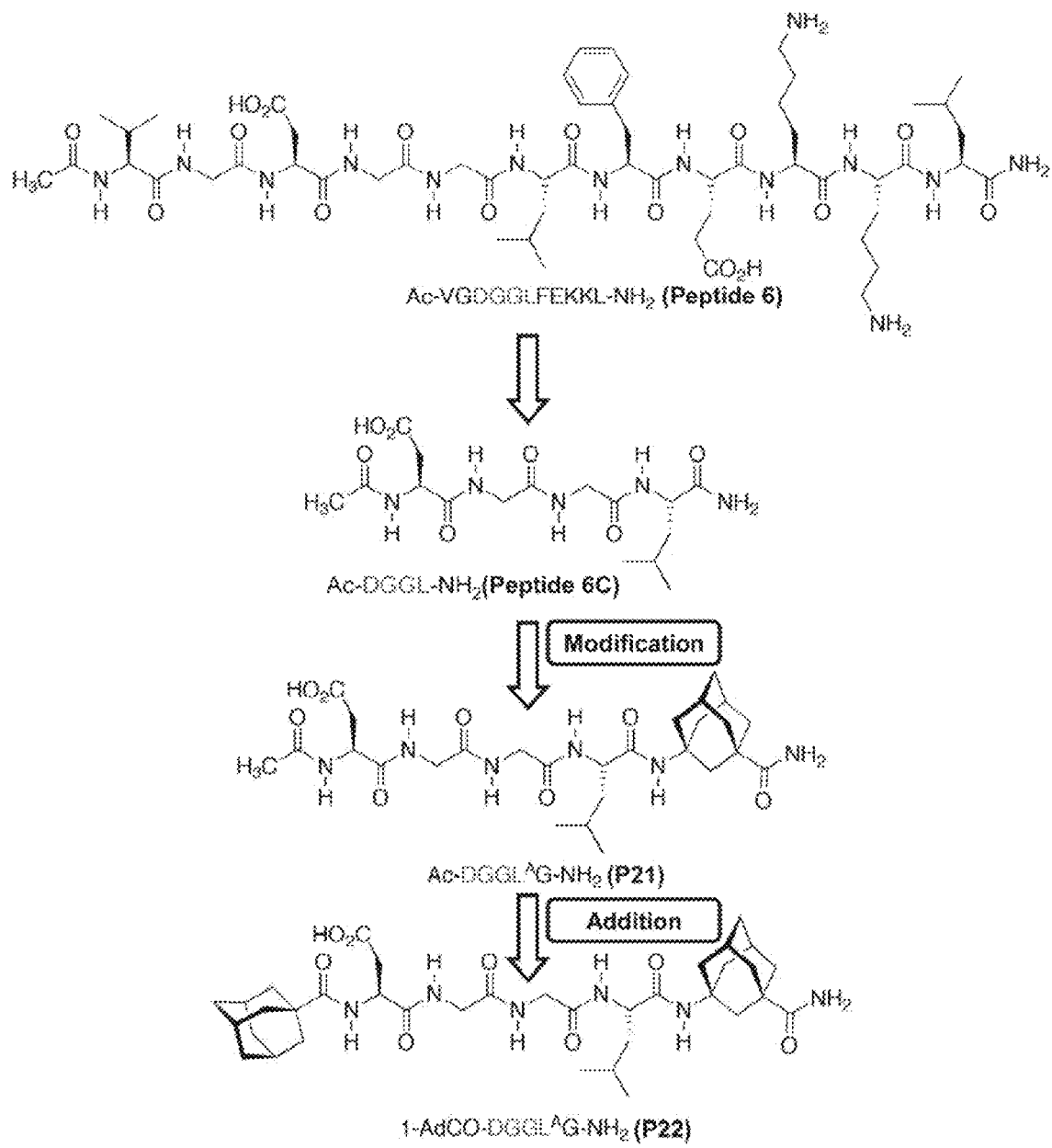

FIG. 15 shows the design and structures of neurogenic peptidergic compounds incorporating adamantane building blocks. From the neurogenic undecamer Ac-VGDG-GLFEKKL-NH$_2$ (SEQ ID NO: 1) (Peptide 6) a truncated, still neurogenic tetramer Ac-DGGL-NH$_2$ (SEQ ID NO:9) (Peptide 6c) was designed. Addition of an unnatural amino acid based upon adamantane to the C-terminus of this subsequence via SPPS methods produced Ac-DGGL$^A$G-NH$_2$ (P21) (SEQ ID NO: 12); capping of the N-terminus of P21 with adamantane-1-carboxylic acid yielded 1-AdCO-DG-GL$^A$G-NH$_2$ (P22) (SEQ ID NO: 13)

Figure 16:
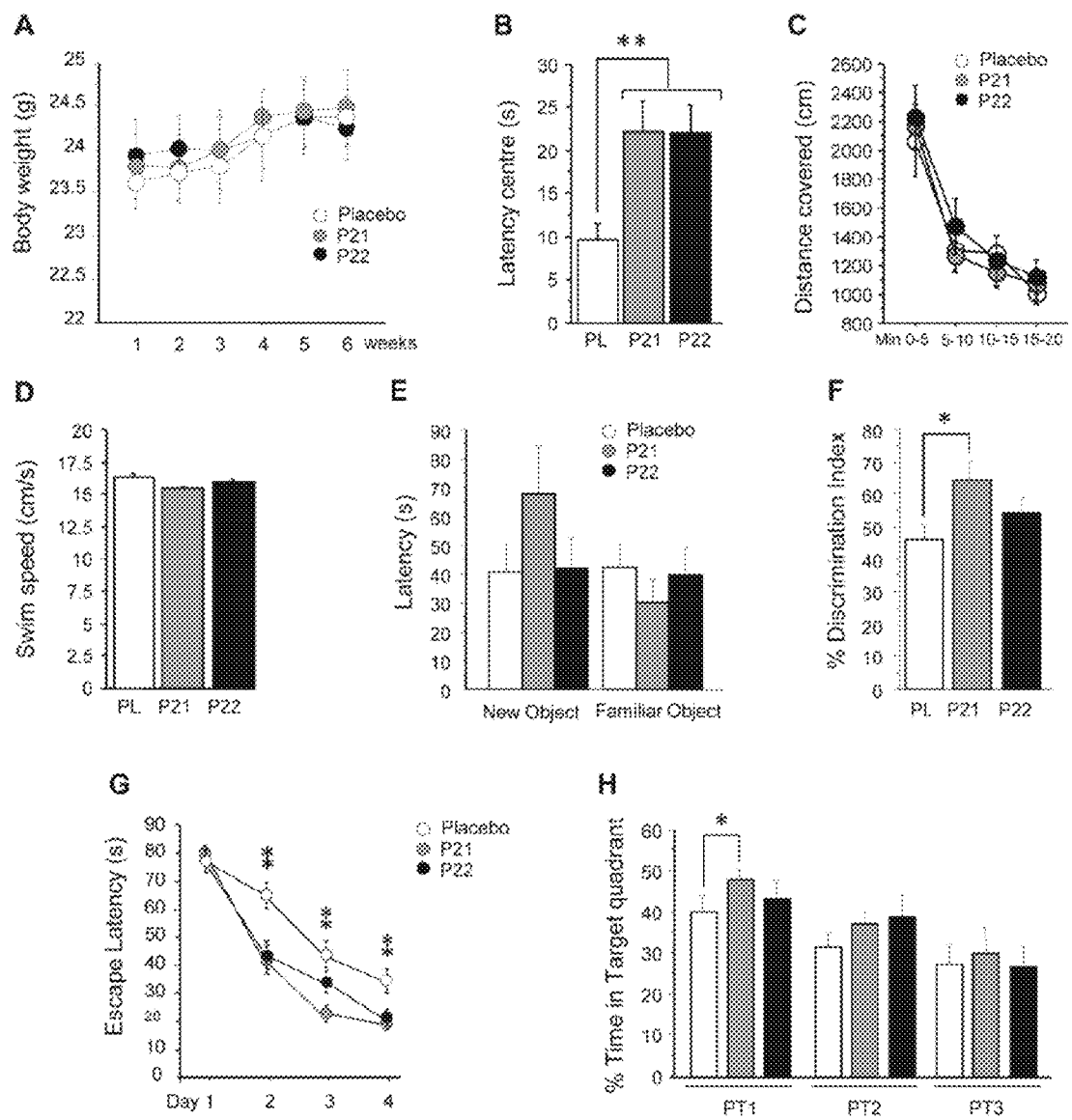
Figure 17:
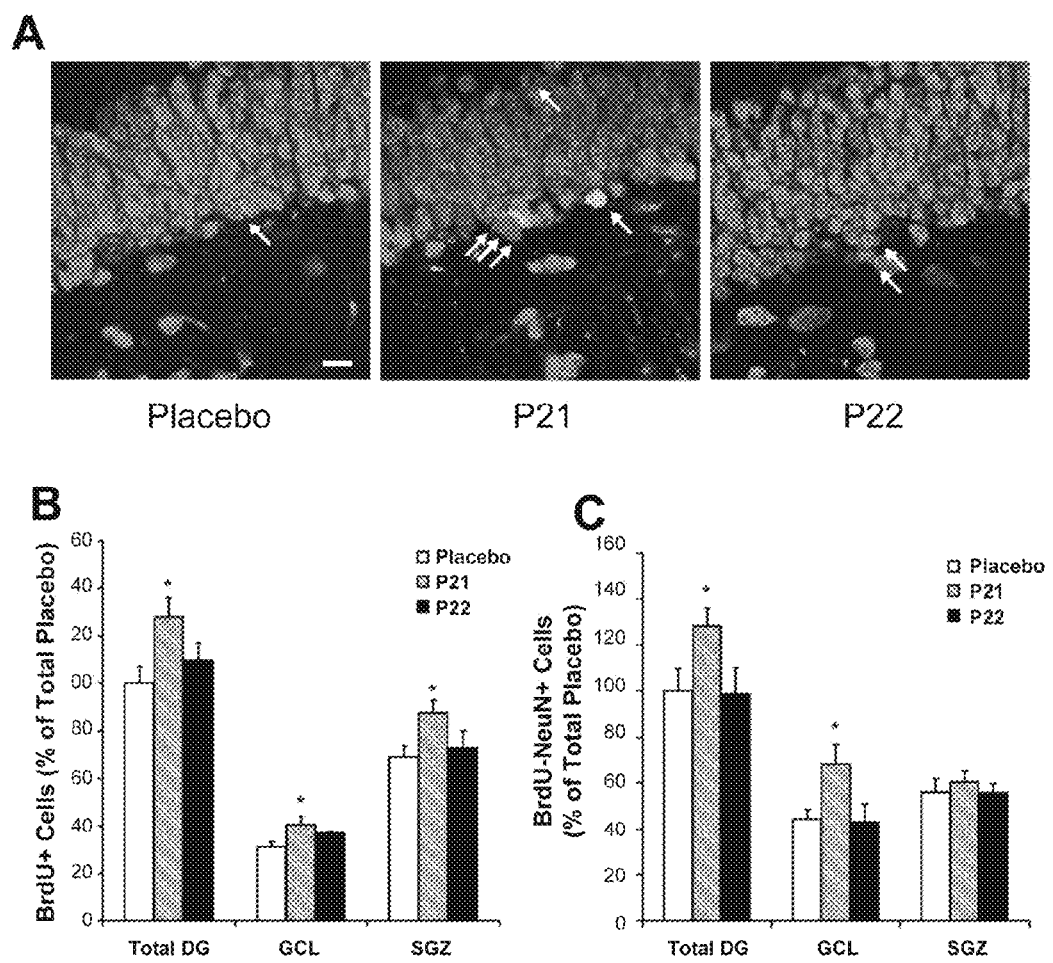
Figure 18:
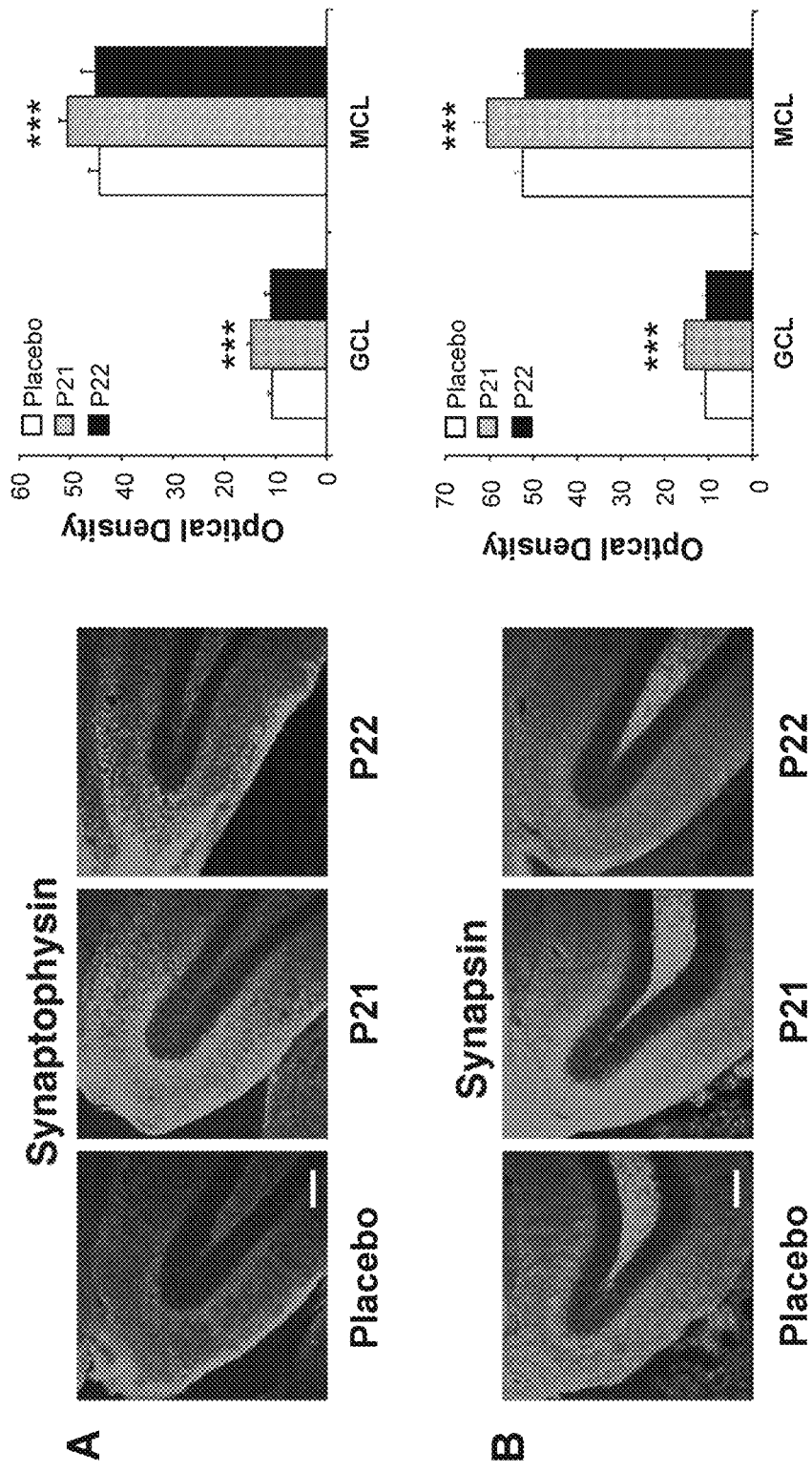

FIG. 16 shows that peptides incorporating AGly improve cognition. P21 and P22 did not induce any effect on body weight (A), exploratory activity (C) or swim speed (D) but reduced anxiety level of mice (B). (E-F) P21 significantly improved the ability to discriminate a new object versus a familiar object. *p<0.05; Student's t-test. (G) P21 and P22 increased performance in the learning of spatial memory task in water maze. **p<0.001; two-way ANOVA with post hoc Fisher LSD test. (H) P21 improved performance in the first probe trial, but treatment with P21 showed no effect 15 days (PT2) or 30 days (PT3) after the end of the treatment. *p<0.05; Student's t-test FIG. 17 shows that compound P21 promotes neurogenesis in the DG. (A) Representative picture of double labeled BrdU (red) and NeuN (green) positive cells. Scale bar represents 20 μm. (B) Numbers of BrdU positive cells were significantly increased in P21 treated animals in the total DG, GCL and in the SGZ (C) P21 treatment significantly increased the number of BrdU/NeuN positive cells in the GCL and in the total DG. *p<0.05, two-way ANOVA and post hoc Fisher LSD test FIG. 18 shows that compound P21 promotes synaptic plasticity in the DG. P21 significantly promoted expression of synaptophysin (A) and synapsin I (B) in the GCL and the MCL of the DG. ***p<0.001, two-way ANOVA and post hoc Fisher LSD test. Scale bars represent 100 μm.

Figure 19:
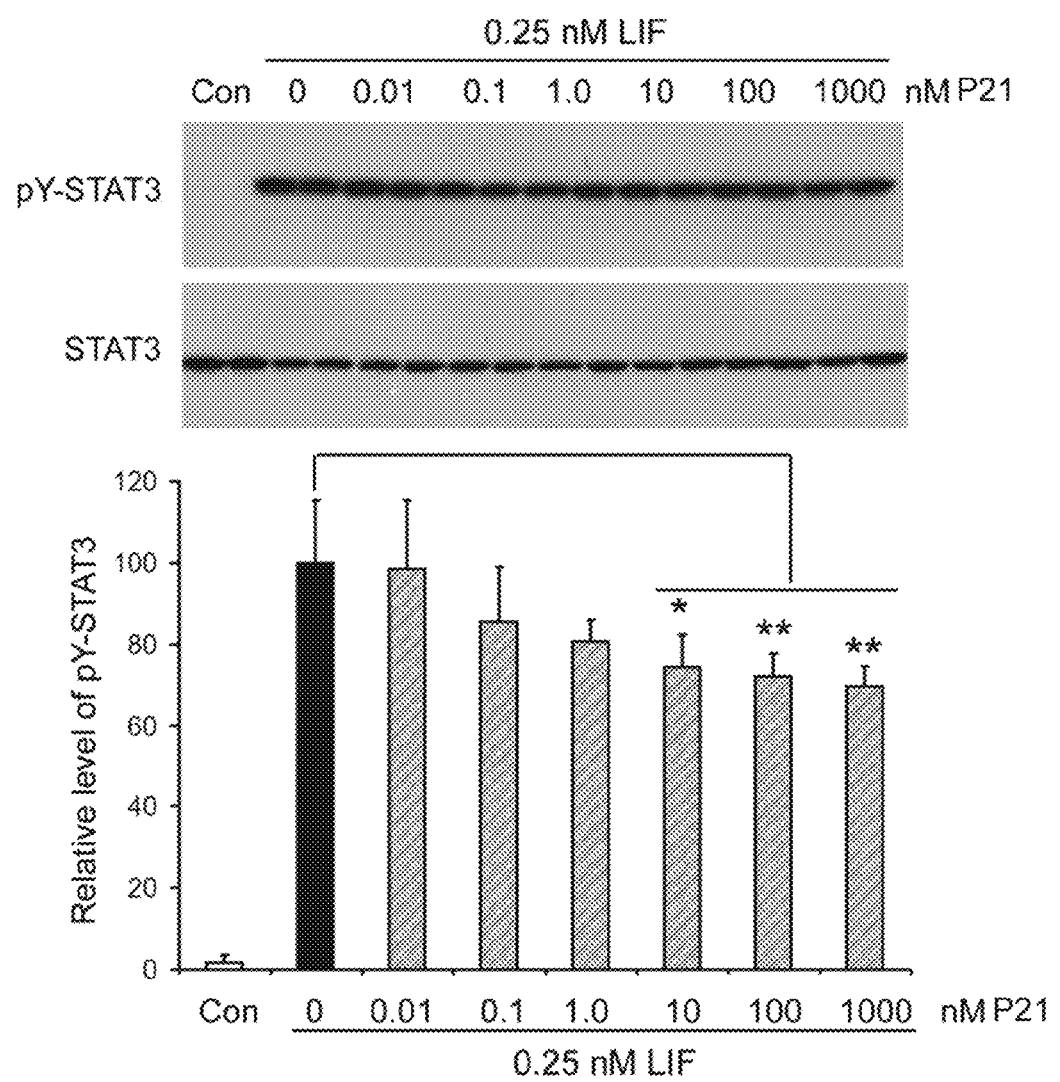

FIG. 19 shows the inhibition of LIF-induced STAT3 phosphorylation by P21 in a dose-dependent manner in HepG2 cells. HepG2 cells were treated with different concentrations of P21 together with 0.25 nM LIF for 15 min, and then the STAT3 phosphorylation at Tyr705 (pY-STAT3) was determined by Western blots. The pY-STAT3 value was normalized to total STAT3 expression. Data are presented as percentages of the value from cells treated with 0.25 nM LIF alone (100%). *p<0.05; **p<0.01.

Figure 20:
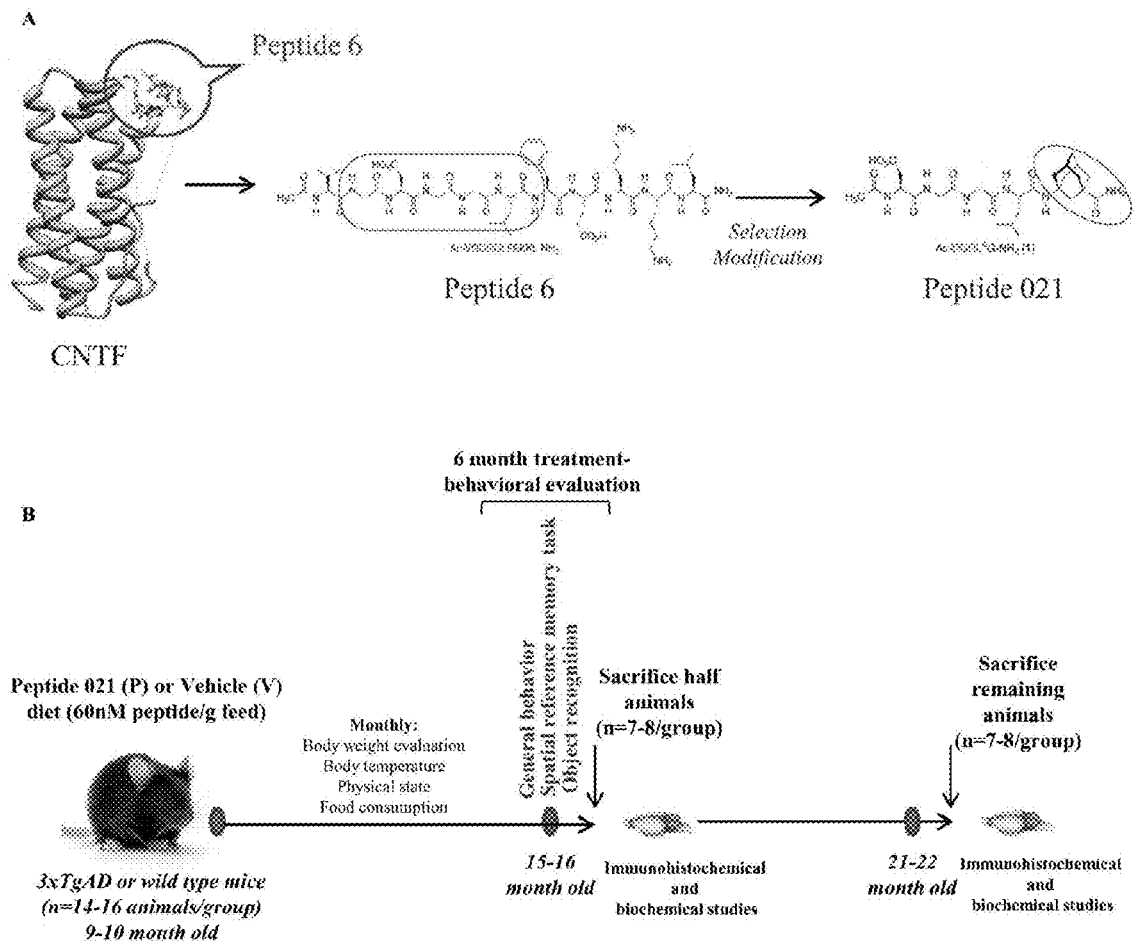

FIG. 20 is is a series of graphs showing: (A) the design and structures of CNTF derived peptidergic compounds with the position of peptide 6 in CNTF is shown. Protein Data Base rendering of one 4-helix bundle of truncated human CNTF (Residues 2-187), generated from CNTF. Only one protein chain is shown for clarity. Residues $^{149}$GGLFEKKL$^{156}$ (SEQ. ID NO. 15) are shown as a tube model, while the rest of the sequence are presented as ribbon. The structures of peptides 6 and 021 are also shown. From the neurogenic undecamer Ac-VGDGGLFEKKL-NH$_2$ (Peptide 6) (SEQ. ID NO. 1), a truncated, still neurogenic tetramer Ac-DGGL-NH$_2$ (Peptide 6c) (SEQ. ID NO. 9) was designed. Addition of an unnatural amino acid based upon adamantane to the C-terminus of this subsequence via solid phase peptide synthesis methods produced Ac-DGGL$^A$G-NH$_2$ (P021) (SEQ. ID NO. 12); and (B) shows the design of the study.

Figure 21:
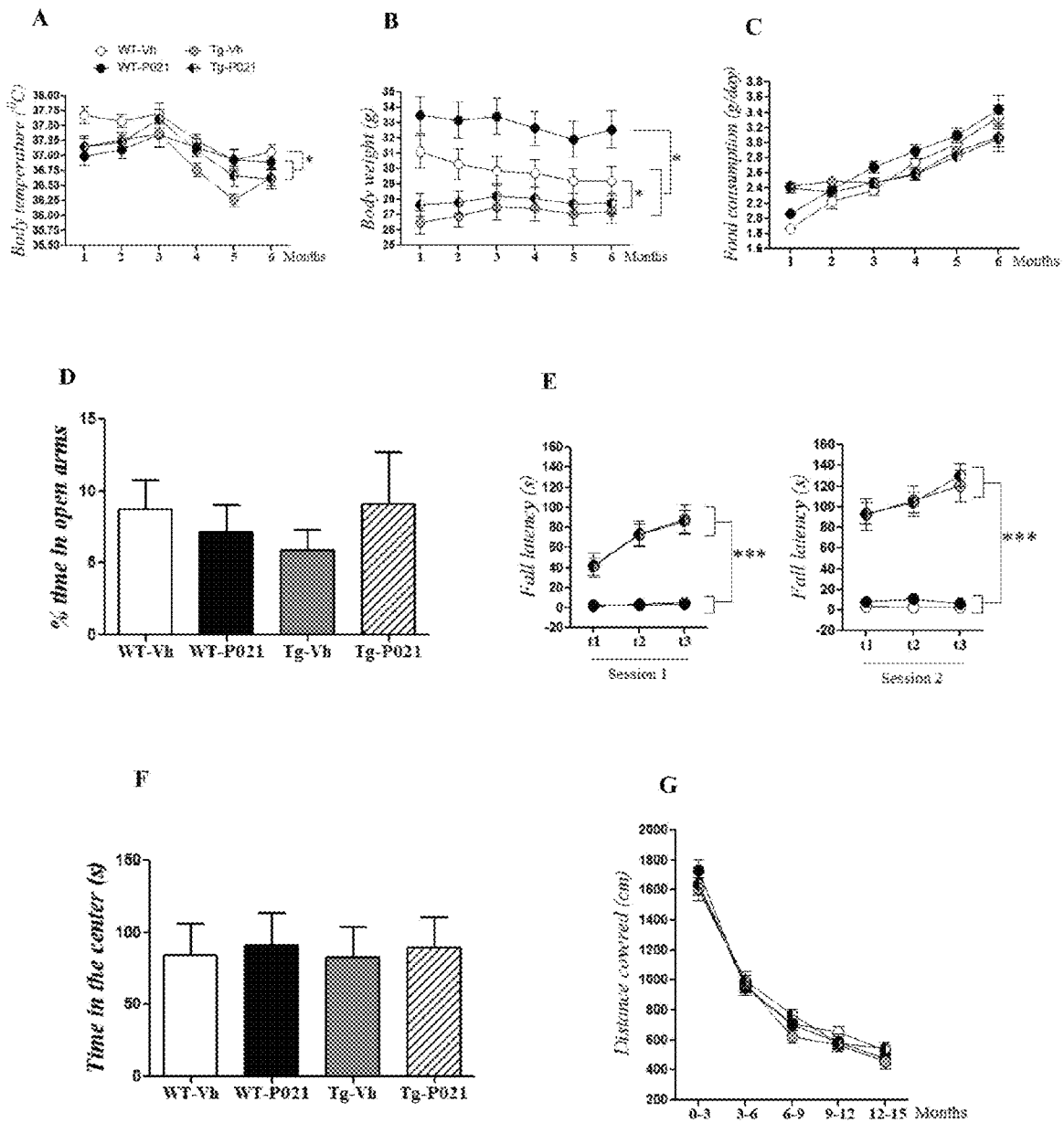

FIG. 21 is a series of graphs showing general behavioral evaluation at 15-16 months of age (6-month treatment). Treatment with Peptide 021 did not induce side effects. FIGS. 21(A-C) show monthly evaluation of body temperature, body weight, and food consumption. The WT animals treated with vehicle compared to other groups had higher body temperatures. The treatment with Peptide 021 induced an increase of weight in WT animals, and the WT mice irrespective of treatment remained heavier than 3xTg-AD mice. The treatment with Peptide 021 did not induce any significant change of weight in 3xTgAD mice. No significant differences were found in food consumption. FIG. 21(D) shows genotype or treatment did not induce any significant difference in anxiety levels. FIG. 21(E) shows 3xTgAD mice exhibited higher scores than WT animals in the Rotarod task suggesting higher locomotivity and locomotor coordination. FIGS. 21(F-G) show that in open-field free exploration task, no significant differences were found the amount of time spent in the center of the arena and the overall distance covered suggesting comparable motivation for exploration. No effect of the treatment with Peptide 021 was observed. Data are shown as mean±S.E.M. Data based on WT-Vh (n=15), wT-P021 (n=14), Tg-Vh (n=15), and Tg-P021 (n=16). *p<0.05, p<0.01, and *p<0.001.

Figure 22:
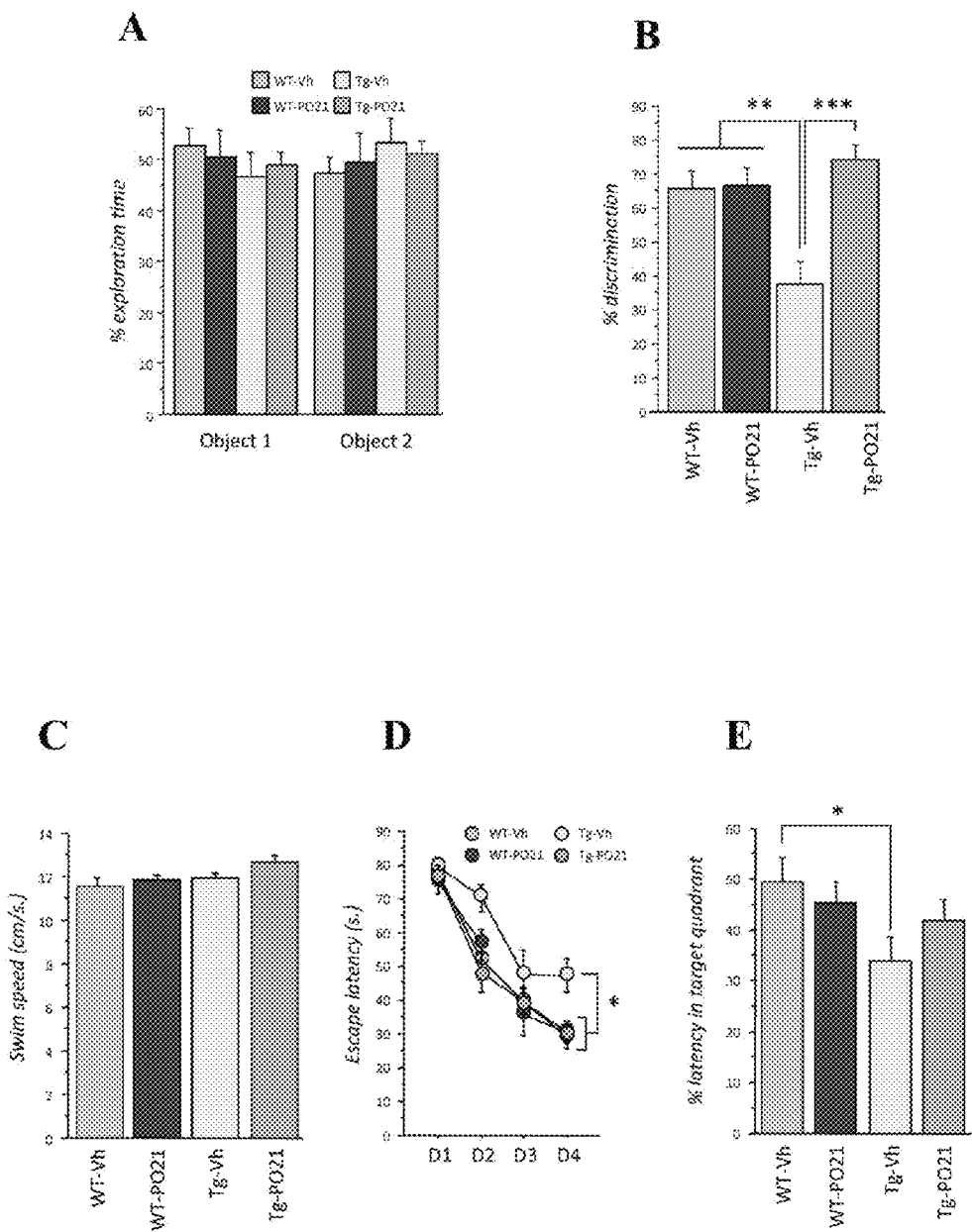

FIG. 22 is a series of graphs showing treatment with Peptide 021 rescued cognitive impairments in 15-16 months old 3xTg-AD mice. FIGS. 22(A-C) show that in the sample phase of the one-trial object recognition task, all animal groups similarly explored both objects. In the test phase of the one-trial object recognition task, 3xTg-AD mice explored the familiar object more (discrimination index, 0.37), reflecting an impairment of discrimination. Treatment with Peptide 021 reversed this impairment. FIGS. 22(D-E) sow that in the spatial reference memory task, 3xTg-AD mice and WT controls displayed similar swim speed and treatment with Peptide 021 did not have any effect on velocity. During the training of the spatial reference memory task, performance of 3xTg-AD mice was delayed compared to WT controls, but treatment with Peptide 021 reversed this impairment. In probe trial, 3xTgAD mice spent less time in the target quadrant. This deficit was rescued by treatment with Peptide 021. Data are shown as mean±S.E.M. Data based on WT-Vh (n=15), WT-P021 (n=14), Tg-Vh (n=15), and Tg-P021 (n=16). *p<0.05, p<0.01, and *p<0.001.

Figure 23:
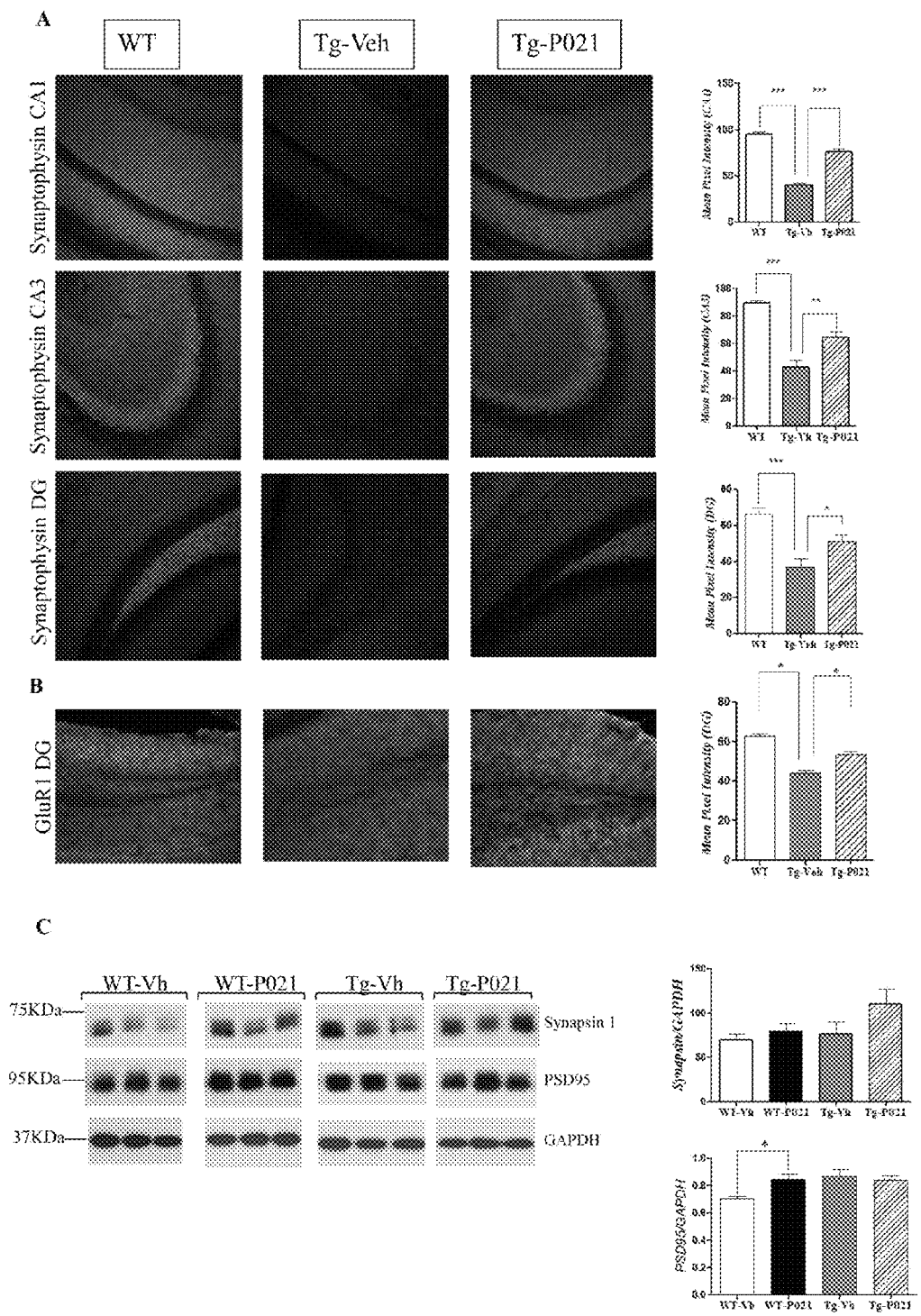

FIG. 23 is a series of graphs showing treatment with Peptide 021 prevented synaptic loss in 15-16 months old 3xTgAD mice. FIG. 23A shows that 3xTgAD mice showed significantly reduced synaptophysin density in the CA1, CA3, and dentate gyrus of the hippocampus. Treatment with Peptide 021 restored synaptophysin densities to WT control levels. Representative photomicrographs illustrating synaptophysin immunoreactivity in the different regions of hippocampus are shown. FIG. 23B shows Peptide 021 induced increase in the glutamate receptor expression (GluR1 in dentate gyrus). FIG. 23C shows Western blots developed with specific synaptic marker antibodies, synapsin 1 and PSD95. A significant increase in PSD95 expression was induced by Peptide 021 treatment in WT animals. Representative Western blots from 3 animals from each group are shown. Quantification of the Western blots is shown as mean±S.E.M. from WT-Vh (n=7), WT-P021 (n=7), Tg-Vh (n=7), and Tg-P021 (n=8). *p<0.05, p<0.01, and *p<0.001.

Figure 24:
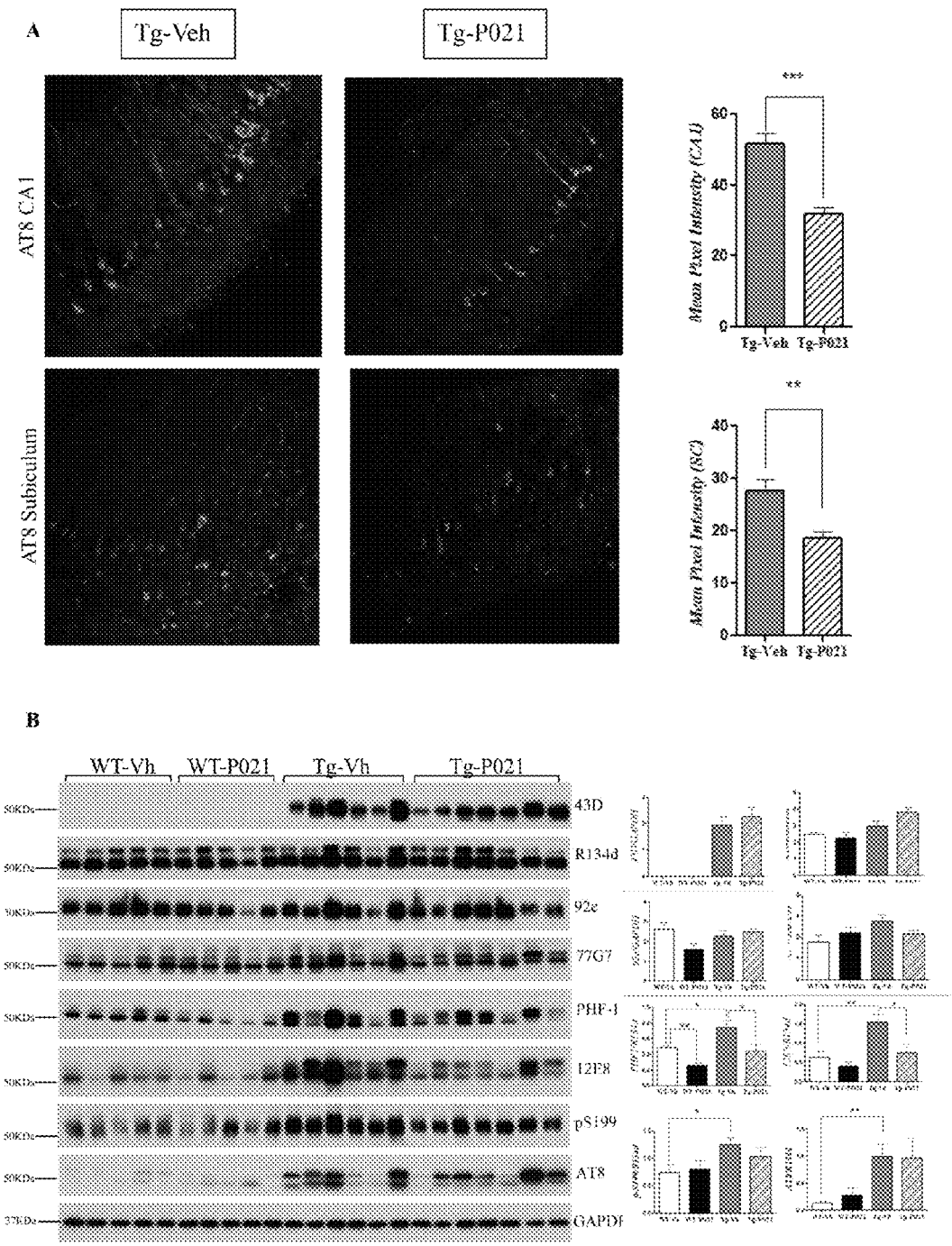

FIG. 24 is a series of graphs showing treatment with Peptide 021 significantly reduced abnormal hyperphosphorylation tau both in 15-16 months old (6 months treatment) and 21-22 months old (12 months treatment) animals. FIG. 24A shows that in the subiculum and the CA1 regions of the hippocampus, AT8 (tau pSer202, pThr 205) density was decreased by treatment with Peptide 021 in 3xTg-AD mice. Representative photomicrographs illustrating AT8 immunoreactivity in the different regions of hippocampus are shown. FIG. 24B shows that Peptide 021 treatment significantly reduced abnormal hyperphosphorylation of tau at sites pSerine 396/pSerine 404 (PHF-1) and pSerine-262/pSerine-368 (12E8). Blots developed with human specific tau antibody 43D showed the protein expression only in 3xTgAD mice. Pan-tau antibodies, 92e, R134d, and 77G7 did not show any significant difference between groups. Quantification of the Western blots is shown as mean±S.E.M. from WT-Vh (n=5), WT-P021 (n=5), Tg-Vh (n=6), and Tg-P021 (n=7). *p<0.05, p<0.01, and *p<0.001.

Figure 25:
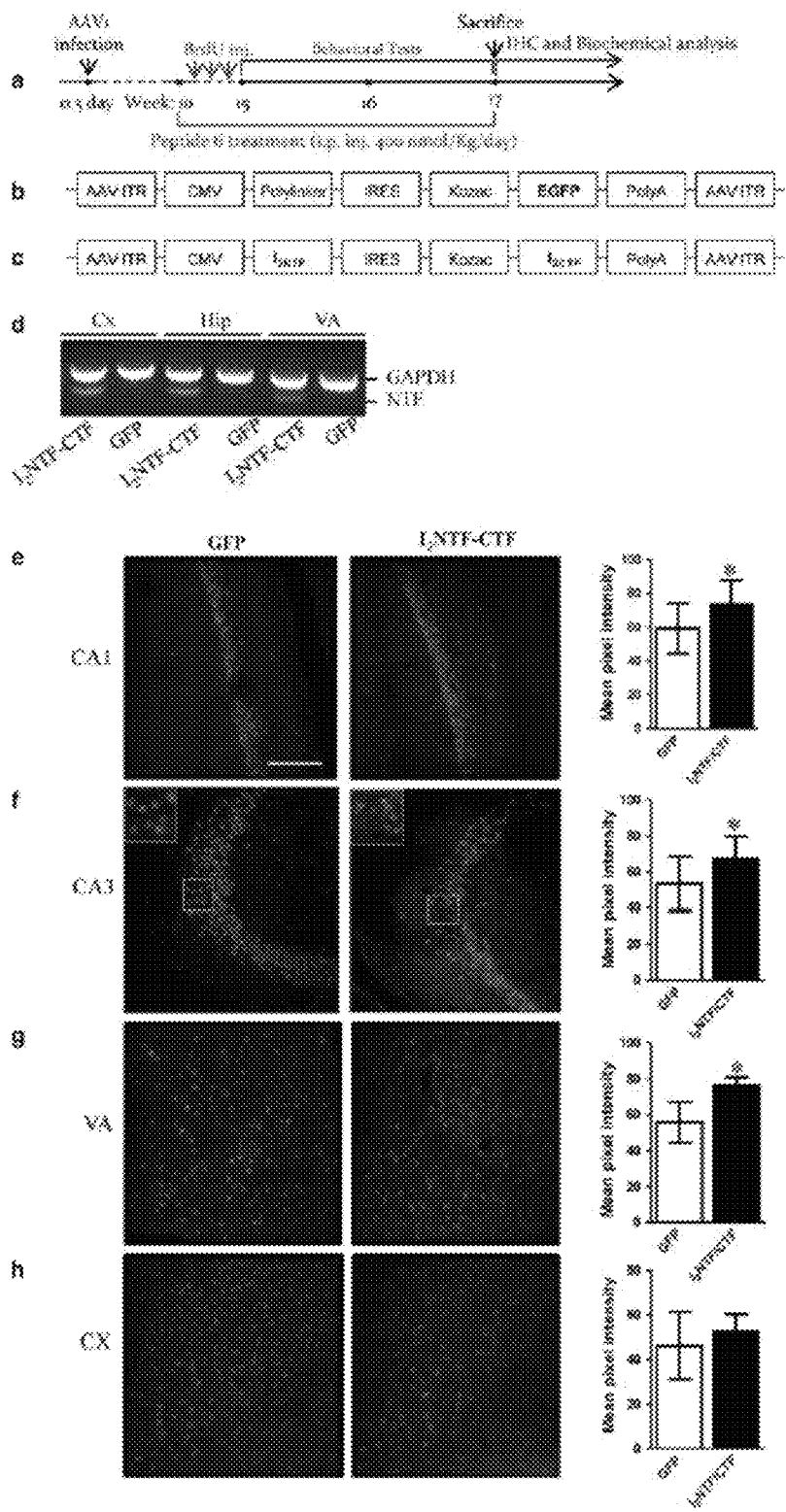

FIG. 25 is a series of graphs showing transduction of the brains of newborn rats with AAV1-$I_{2NTF-CTF}$ and stable expression of $I_{2NTF}$ and $I_{2CTF}$ 4 months postinjection, where (a) is a schematic representation of the outline of the study and includes linear maps of the AAV vector plasmids (based on pTRUF12). With the exception of the inverted terminal repeats (ITR) all viral genes had been removed and replaced with (b) GFP, or (c) $I_{2NTF}$ and $I_{2CTF}$. CMV cyglomegalovirus promoter, IRES internal ribosomal entry site from poliovirus. FIG. 25(d) shows that the mRNA expression of $I_{2NTF}$ was detected by reverse-transcriptase polymerase chain reaction (rt-PCR) of RNA extracted from cortex (CX), hippocampus (Hip) and ventricular area (VA) of GFP and $I_{2NTF-CTF}$ rats and separated by agarose gel. FIGS. 25(e)-(h) are representative confocal images illustrating the expression of $I_2^{PP2A}$ in GFP and $I_{2NTF-CTF}$ rats; the GFP auto fluorescence was negligible and the scale bar is 100 µm. Quantification of $I_2^{PP2A}$ staining fluorescence intensity in CA1 (e), CA3 (f) of the Hip, VA (g) and CX (h). Data are presented as mean±SD. *p<0.05

Figure 26:
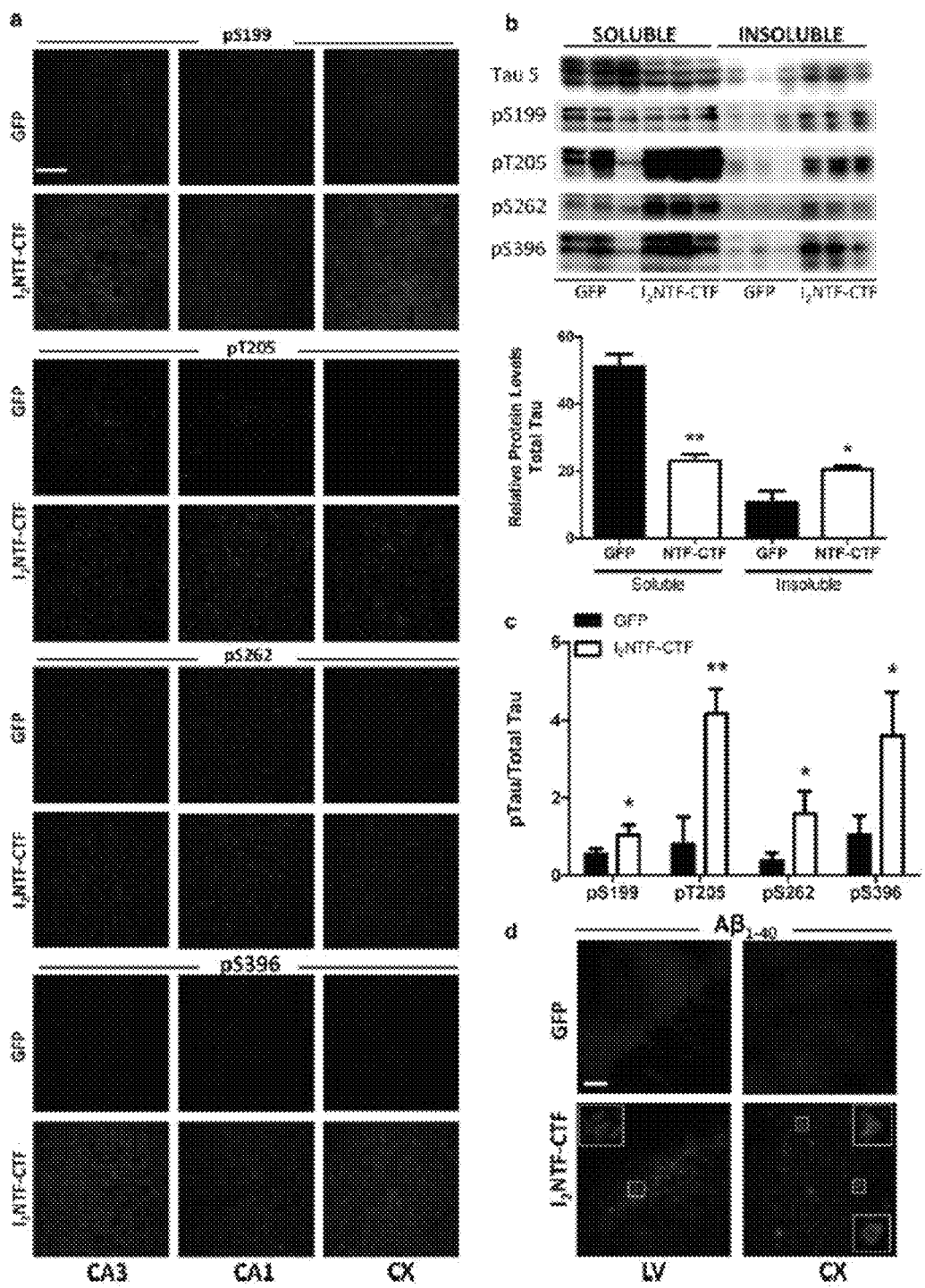

FIG. 26 is a series of graphs showing that $I_{2NTF-CTF}$ rats at 13 months of age show an increase in abnormal hyperphosphorylation and aggregation of tau and intraneuronal Ab, where (a) is immunohistochemical staining with anti-tau pSer199, pThr205, pSer262, and pSer396 in CA3 and CA1 areas of the hippocampus and in the cerebral cortex (CX) in $I_{2NTF-CTF}$ and GFP control rats; (b) are Western blots and quantitation of sarkosyl-soluble and sarkosylinsoluble fractions from the cerebral cortices of $I_{2NTF-CTF}$ and GFP rats developed with a pan tau antibody Tau5 and phosphotau antibodies pSer199, pThr205, pSer262, and pSer396; (c) is abnormal hyperphosphorylation of tau (ptau/total tau) determined by quantitation of Western blots from the cerebral cortices of $I_{2NTF-CTF}$ and GFP rats; (d) is immunohistochemical staining with anti-Ab40 (Invitrogen) of the lateral ventricle (LV) area and the cerebral cortex (CX) in $I_{2NTF-CTF}$ and GFP rats, where insets show intraneuronal Ab, the magnification bar in a 50 µm, d 100 µm, and *p<0.05; **p<0.01.

Figure 27:
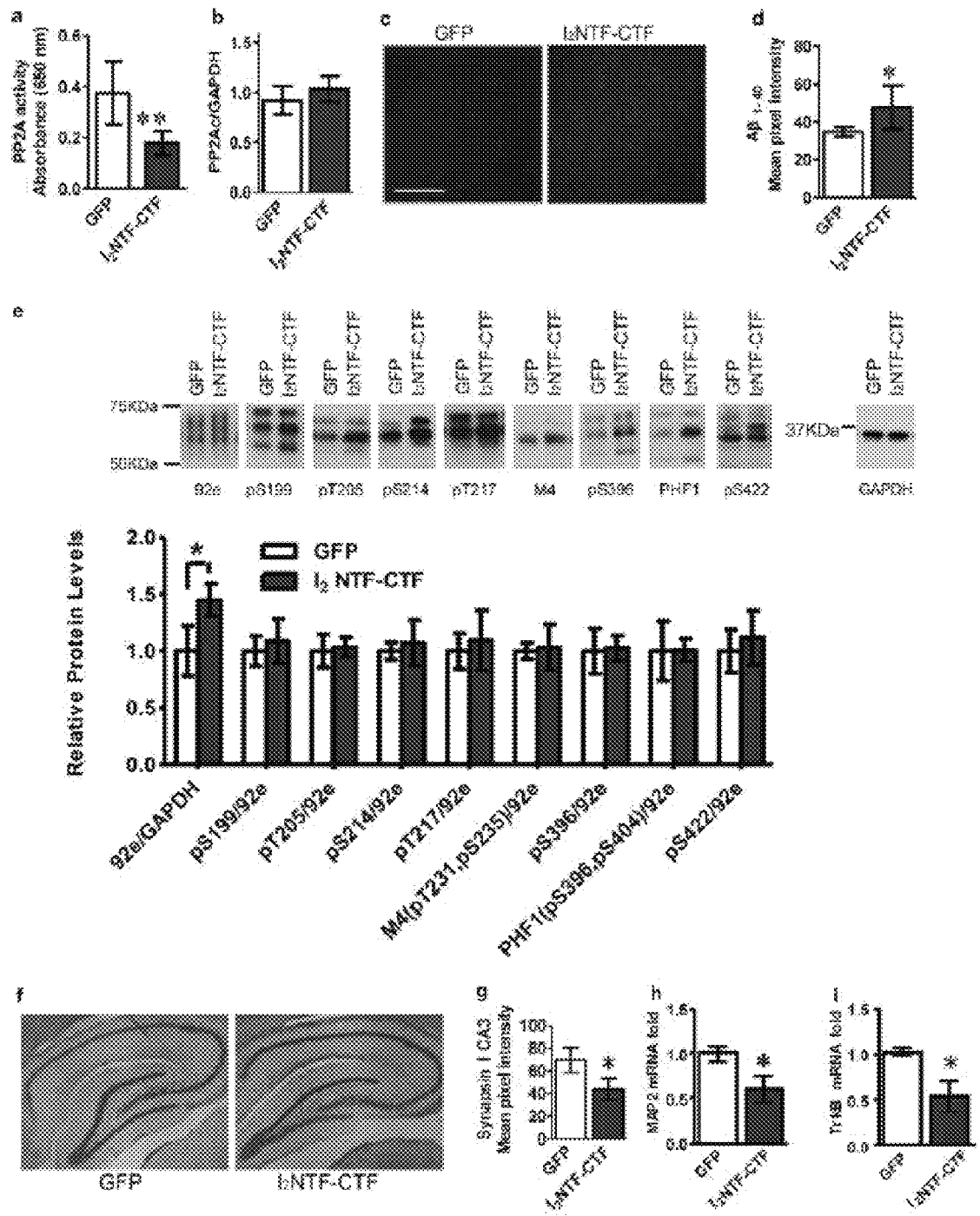

FIG. 27 is a series of graphs showing reduced PP2A activity, accumulation of Ab1-40 and tau, and loss of neuronal plasticity in $I_{2NTF-CTF}$ rats, where (a) is PP2A activity in hippocampus extract of 4-month-old rats; (b) is PP2A catalytic subunit (PP2Ac) level assayed by Western blots in hippocampus homogenatel; (c) is representative photomicrographs; and (d) is semi-quantitative expression level of Ab1-40 in the cortex of GFP and $I_{2NTF-CTF}$ rats. FIG. 22(e) is representative Western blots developed with phospho-specific tau antibodies, where quantification of total tau, and hyperphosphorylation of tau at pSer199, pThr205, pSer214, pThr217, pThr231/pSer235, pSer396, pSer396/pSer404, and pSer422. Quantification of Western blots is shown as ±SD, normalized by GAPDH for total tau and for all the phosphorylation sites by total tau. FIG. 27(f) are images of Nissl staining of hippocampus from GFP and $I_{2NTF-CTF}$ rats; (g) is the expression level of synapsin I in CA3 of the hippocampus detected by immunohistochemistryl (h) is mRNA expression level of MAP2, quantified by RTqPCR, in cortex form GFP and $I_{2NTF-CTF}$ rats; and (i) is mRNA expression level of TrkB receptor, quantified by RT-qPCR, in cortex form GFP and $I_{2NTF-CTF}$ rats, where *p<0.05.

Figure 28:
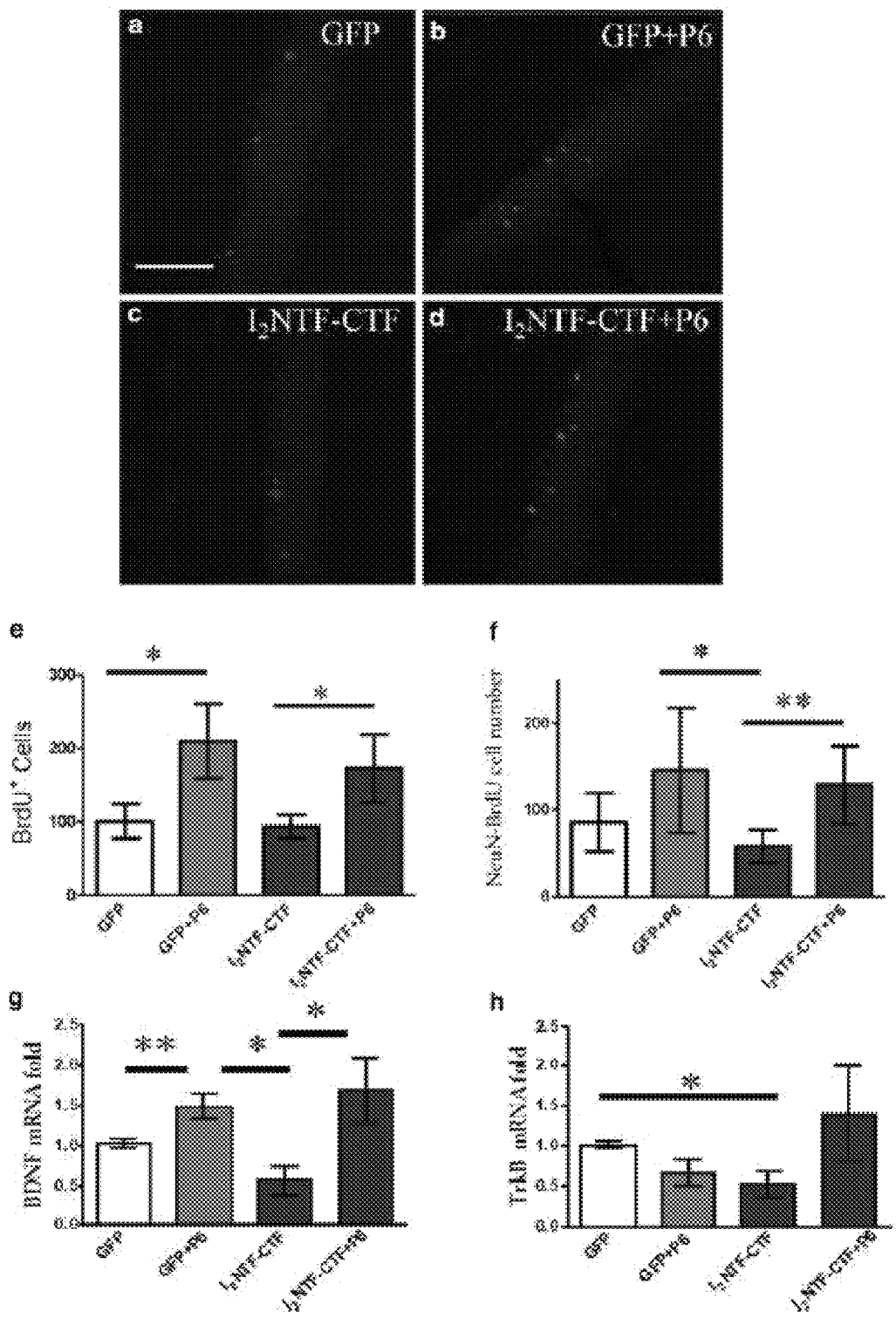

FIG. 28 is a series of graphs showing Peptide 6-induced increase in neurogenesis in $I_{2NTF-CTF}$ and GFP rats, where (a-d) are photomicrographs illustrating expression of BrdU- (red) and NeuN-positive cells (blue) and the scale bar 20 µm; (e) is the quantification of BrdUpositive cells in the iGCL of the DG; (f) is the co-localization of BrdUNeuN-IR cells in the SGZ; (g) is the mRNA expression level of BDNF and h TrkB receptor, quantified by RT-qPCR, in cortex from GFP and $I_{2NTF-CTF}$ rats treated with Peptide 6 (P6) or vehicle only, and data are expressed as the fold difference compared with vehicle-treated GFP animals (*p<0.05, **p<0.01).

Figure 29:
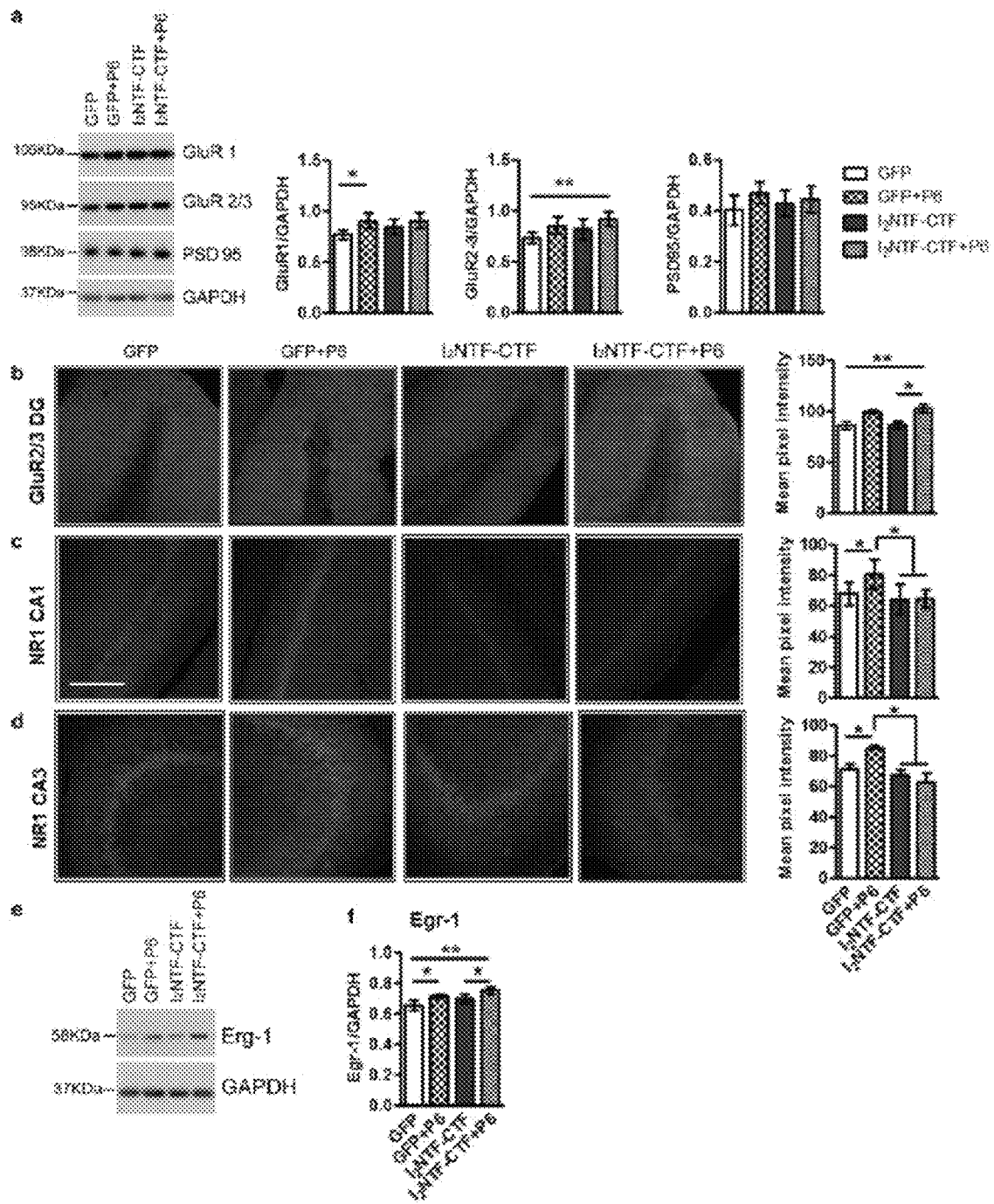

FIG. 29 is a series of graphs showing Peptide 6 (P6)-induced increase in glutamate receptor levels, where (a) is representative immunoblots and relative quantification in the whole hippocampus of GluR1, GluR2-3 and PSD-95; and representative photomicrographs and semi-quantitative expression level of GluR2/3 in DG (b), NR1 in CA1 (c), and CA3 (d) and the scale bar is 100 µm; (e) are representative Western blots and relative quantification of Egr-1 normalized against GAPDH in hippocampus homogenate, where *p<0.05, **p<0.01.

Figure 30:
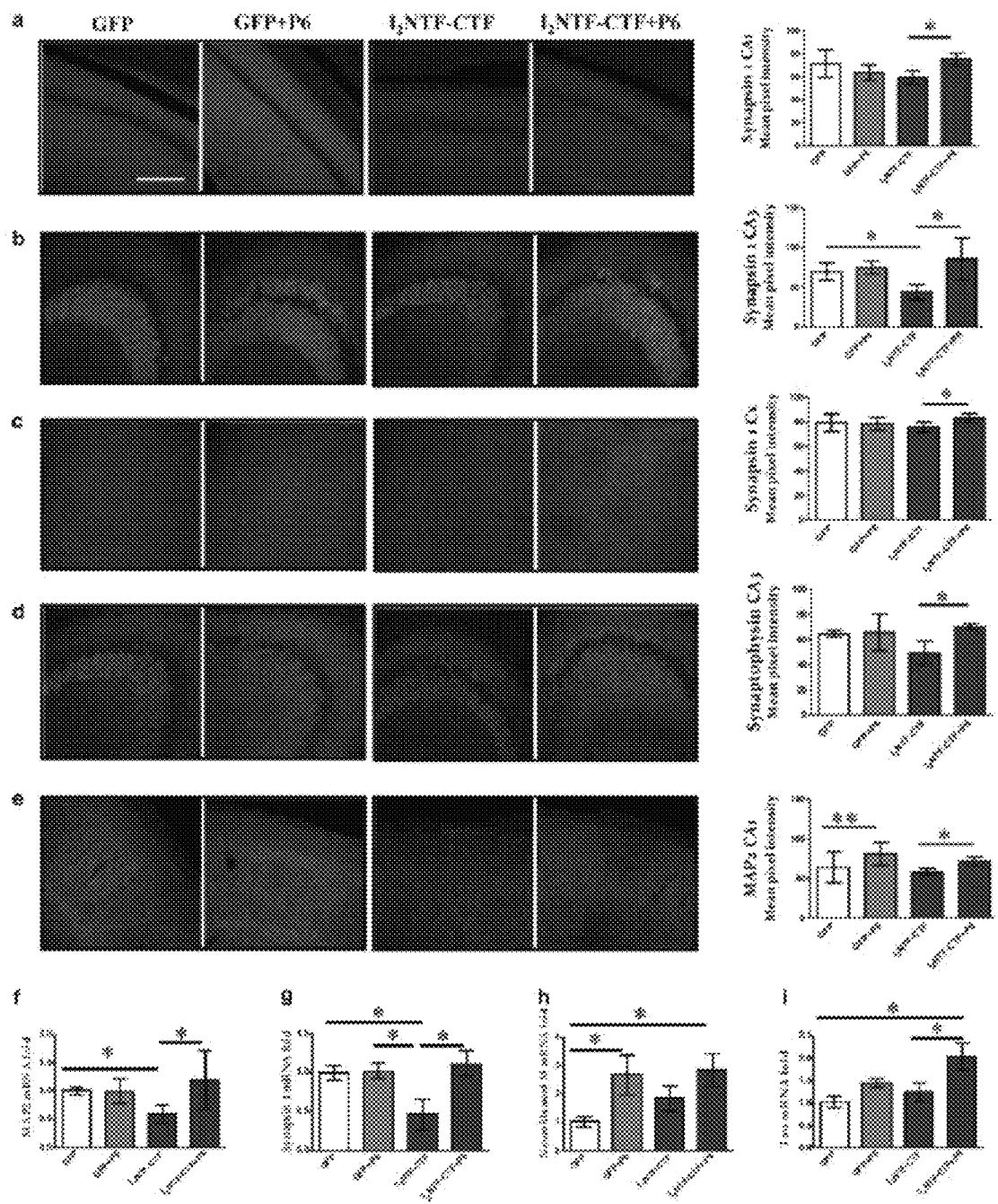

FIG. 30 is a series of graphs showing Peptide 6 (P6)-induced increase in dendritic and synaptic plasticity, where representative photomicrographs and semi-quantitative expression level of synapsin I in CA1 (a), CA3 (b) and cortex (c), synaptophysin in CA3 (d), and MAP2 in CA1 (e) and the scale bar 100 µm. The mRNA expression level of MAP2 are seen in (f), synapsin I (g), neurofilament M (h) and tau (i) quantified by RT-qPCR in cortex (*p<0.05, **p<0.01).

Figure 31:
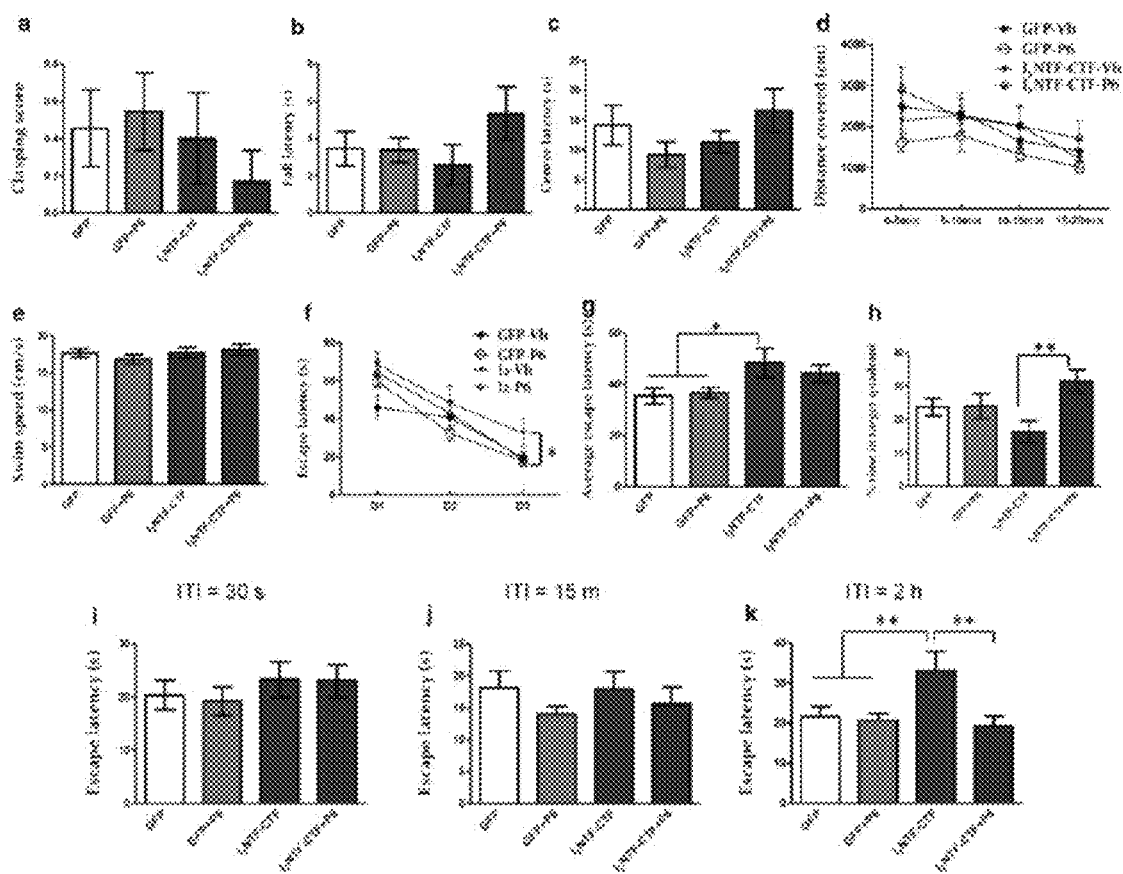

FIG. 31 is a series of graphs showing that treatment with Peptide 6 (P6) rescued cognitive impairments in $I_{2NTF-CTF}$ rats, where (a-d) show general behavior and. more particularly, (a) is clasping reflex, (b) is prehensile traction test, (c) is anxiety in the open field, (d) is exploration in the open field. FIG. 31(e)-(h) are spatial reference memory tasks, namely, (e) swim speed; (f) learning performance across training; (g) training performance, average escape latencies; (h) probe trial, % of time spent in the target quadrant. FIG. 26(i)-(h) are working memory tasks, namely, (i) Day 1 inter-trial intervals (ITI) 30 s; (j) Day 2 ITI 15 min; and (k) Day 3 ITI 2 h.

DETAILED DESCRIPTION OF THE INVENTION

As described in co-pending application Ser. No. 13/044,323, hereby incorporated by reference, the ciliary neurotrophic factor (CNTF) peptide referred to as Peptide 6 and having the sequence VGDGGLFEKKL (SEQ ID NO: 1), which comprises residues 145-155 of CNTF (or residues 146-156 if the starting amino terminal methionine is counted), was found to be neurogenic and neurotrophic, as well as blood-brain-barrier permeable with an in vitro plasma stability and a half-life of over six hours.

Example 1

Figure 1:
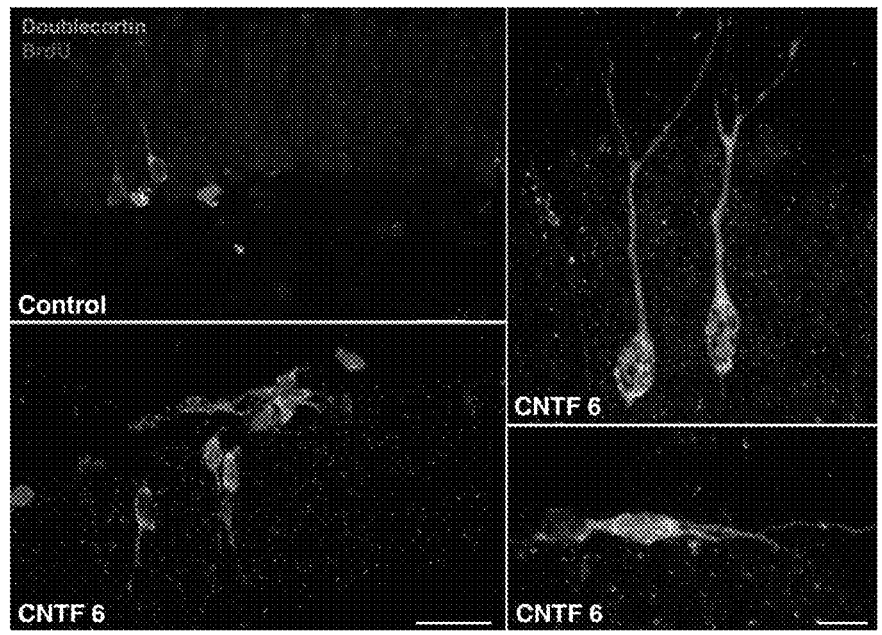
FIG. 1 shows the effect of Peptides 5, 9 and 10 on the expression of DCX in BrdU, bromodeoxyuridine, labeled progenitors in the dentate gyrus.
Figure 1:
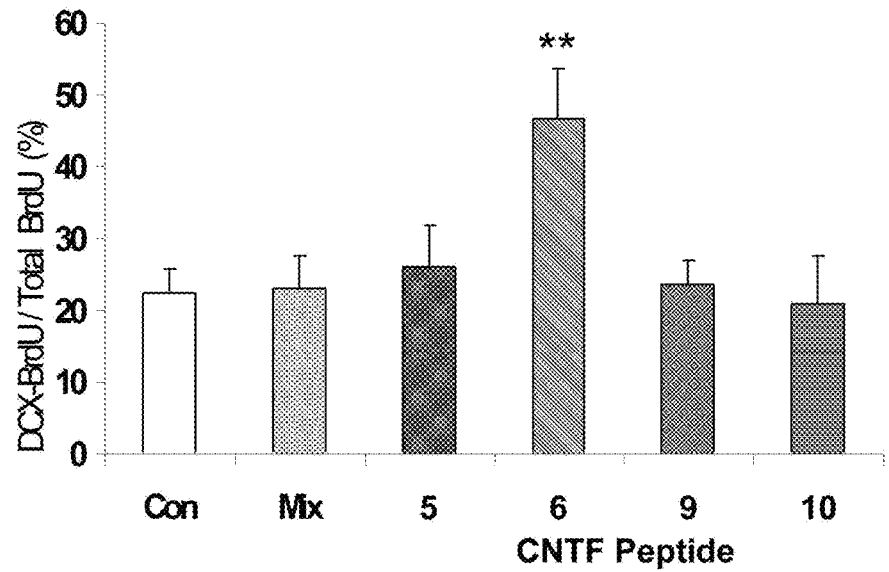
Figure 2:
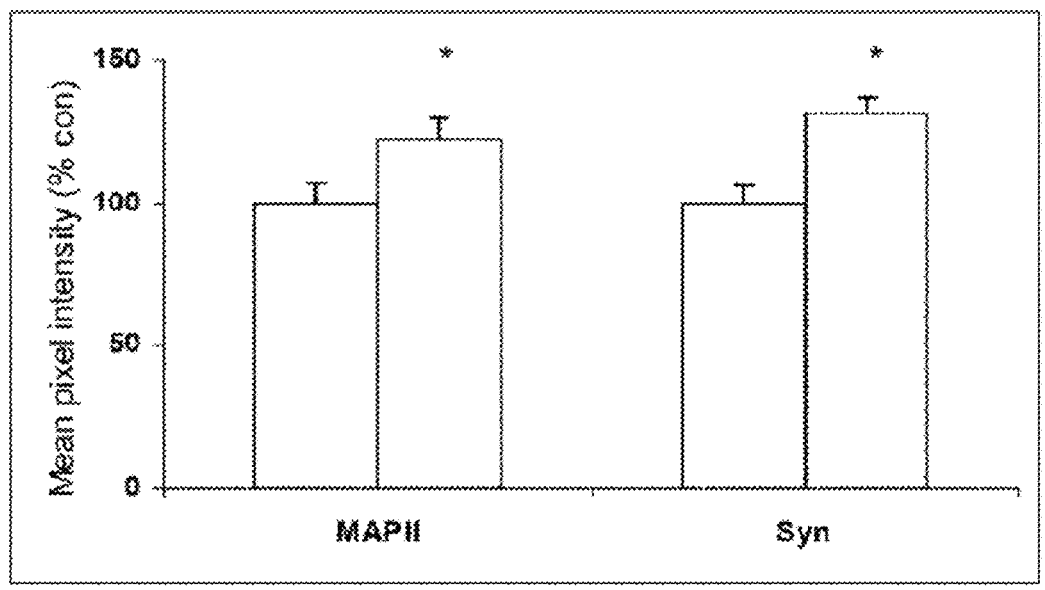
FIG. 2 shows the MAP2 and synaptophysin immunoreactivity in the dentate gyrus when Peptide 6 is administered.

Efficacy of the present invention in improving cognitive impairment has been established in animal models. More particularly, Peptide 6 induced a two fold increase in the differentiation of dentate gyrus progenitors into DCX (doublecortin) expressing cells in a 14 day treatment group of the mouse model C57/BL6. As seen in FIG. 1, Peptides 5, 9 and 10 did not have any effect on the expression of DCX in BrdU labeled progenitors in the dentate gyrus. As seen in FIG. 2, Peptide 6 also caused a statistically significant increase in MAP2 and synaptophysin immunoreactivity in the dentate gyrus of treated mice as measured by mean pixel intensity in the outlined area of interest.

Behavioral tests employing Morris Water maze task-based memory acquisition, retention and recall paradigms have also been carried out. Two groups of 18 mice each were treated with Peptide 6/Placebo containing implantable subcutaneous pellets with user specified timed release kinetics: 14 days for group 1 and 30 days for group 2. In particular, the 30 day group showed significant improvement in memory acquisition as evaluated by time spent in the target quadrant and distance covered in the target quadrant in the Morris Water Maze task.

All experiments involving mice were done on 8-10 month old female retired breeders of C57BL6 background. A total of 33 mice were divided into 10 groups of 3 animals each (except control group which had 6 mice). The groups are described in Table 1. Details of CNTF peptides are described in Table 2.

TABLE 1

| Group | Description | Concentration | # of mice |
|---|---|---|---|
| 1 | Control [normal saline] | | 6 |
| 2 | Peptide mix | 0.5 nmal | 3 |
| 3 | Peptide 5-1 | 0.5 nmal | 3 |
| 4 | Peptide 5-2 | 5 nmal | 3 |
| 5 | Peptide 6-1 | 0.5 nmal | 3 |
| 6 | Peptide 6-2 | 5 nmal | 3 |
| 7 | Peptide 9-1 | 0.5 nmal | 3 |
| 8 | Peptide 9-2 | 5 nmal | 3 |
| 9 | Peptide 10-1 | 0.5 nmal | 3 |
| 10 | Peptide 10-2 | 5 nmal | 3 |

TABLE 2

| CNTF Peptide | Position in CNTF | MW | SEQ ID NO: |
|---|---|---|---|
| Peptide 5 | 133-145 | 1384 | 4 |
| Peptide 6 | 145-155 | 1203 | 1 |
| Peptide 9 | 91-102 | 1427 | 2 |
| Peptide 10 | Loop | 1192 | 11 (CHQGCGGLFEC) |

The animals were kept in groups of 3 per cage. The mice were given daily intraperitoneal injections of four CNTF peptides either separately or in a mixture for 2 weeks as described in Table 1. From day 2, BrdU (Bromodeoxyuridine; 150 mg/kg) was added to the injections. The animals were sacrificed 24 hours after the last injection. Briefly, the animals were perfused transcardially with PBS and their brains taken out and dissected into halves. One hemisphere from each animal was frozen for biochemical analysis and the other was fixed in 4% paraformaldehyde for 48 hours followed by equilibration in 30% sucrose in PBS overnight. These were then processed for immuno-histochemistry.

Fixed tissues were cut into 40 μm sections on a freezing sliding microtome. One in 5 sections per brain was processed for BrdU staining and visualized by immunoflorecence. Cell counting was done on these sections to determine the number of BrdU labeled cells (representing newly born cells) in the dentate gyrus of the hippocampus. The area of counting was limited to the granule cell layer and the subgranular zone (a two-nucleus thick layer adjacent to the granule cell layer). For counting purposes, the dentate gyrus was divided into two areas, the outer granule cell layer (oGCL) consisting of out half of the granule cell layer, and the subventricular zone (SVZ) comprising of the inner half (towards the hilus) of the granule cell layer plus a two-nucleus thick layer adjacent to the outer border of the hilus. Cell counting was done on confocal images of the sections according to the optical dissector principle. Volumetric analysis was carried out with the help of Image Pro software.

Example 2

The efficacy of present invention has further been established in animal models designed to evaluate the treatment of specific neurological diseases, such as Alzheimer disease (AD). In addition to the occurrence of numerous neurofibrillary tangles and Aβ plaques, neurogenesis and neuronal plasticity are markedly altered in AD. Although the most popular therapeutic approach has been to inhibit neurodegeneration, another is to promote neurogenesis and neuronal plasticity by utilizing the regenerative capacity of the brain.

In a transgenic mouse model of AD, 3xTg-AD mice, there is a marked deficit in neurogenesis and neuroplasticity, which occurs before the formation of any neurofibrillary tangles or Aβ plaques, as is associated with cognitive impairment. Peripheral administration of Peptide 6, restored cognition by enhancing neurogenesis and neuronal plasticity in these mice. Although this treatment had no detectable effect on Aβ and tau pathologies in 9-month animals, it enhanced neurogenesis in dentate gyrus, reduced ectopic birth in the granular cell layer, and increased neuronal plasticity in the hippocampus and cerebral cortex. These findings, for the first time, demonstrate the possibility of therapeutic treatment of AD and related disorders by peripheral administration of a peptide corresponding to a biologically active region of CNTF.

Peptide 6, which comprises residues 146-156 of human CNTF, synthesized by solid phase peptide synthesis (SPPS) methods, purified by reversed phase HPLC to greater than 96 percent purity, lyophilized, and characterized via HPLC, NMR, and ESI-MS.

The 3xTg-AD homozygous mice harboring PS1M146V, APP$^{Swe}$, and tau$^{P301L}$ transgenes were obtained from Jackson Laboratory (New Harbor, Me., USA). The background of the 3xTg-AD mice is a hybrid 129/Sv×C57BL/6. NonTg wild type (WT) mice used were from the same strain and genetic background and were obtained from Jackson Laboratory. Mice were housed and bred in accordance with approved protocols from our Institutional Animal Care and Use Committee, according to the PHS Policy on Human Care and Use of Laboratory animals (revised Mar. 15, 2010). This study was performed on homozygous 3xTg-AD female mice. Mice were group-housed (4 animals per cage) with a 12:12 hour light/dark cycle and with ad libitum access to food and water.

Figure 3:
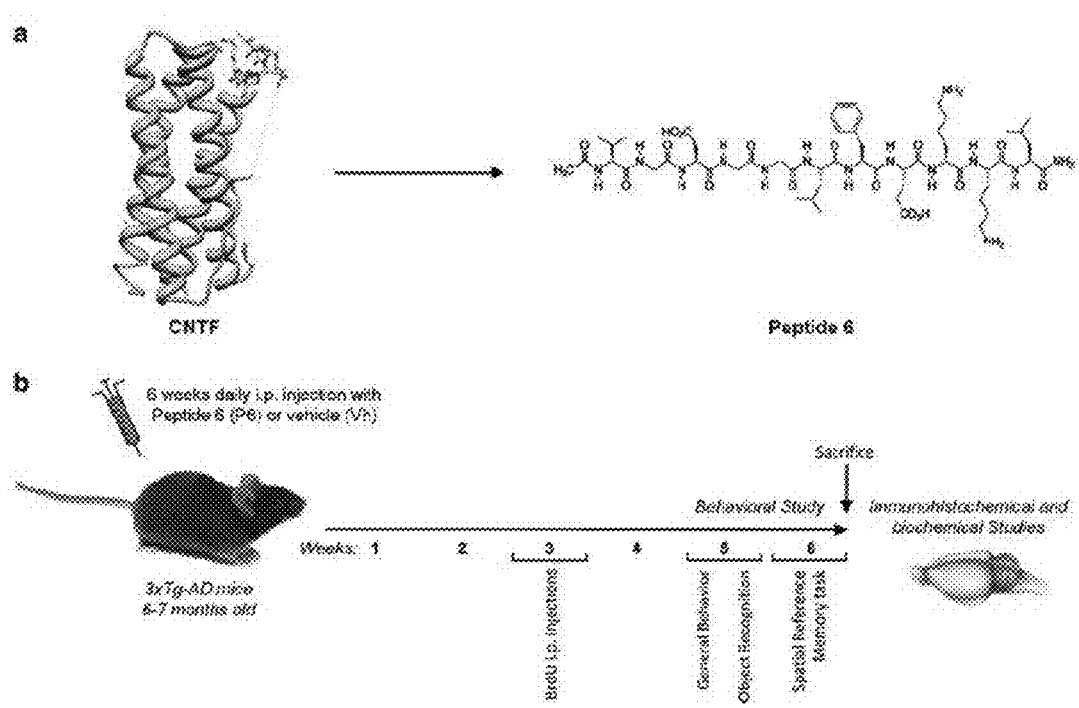
FIG. 3 is a schematic showing the position of Peptide 6 in CNTF along with its structure as well as the design of the study described in Example 2 below.

3xTg-AD mice (6-7 months old) (n=20) and WT controls (n=18) were administered peripherally with Peptide 6 or vehicle control (NaCl, 0.9%) for 6 weeks (daily i.p. 50 nmol 0.1 ml$^{-1}$ injection-1 day$^{-1}$). After 3 weeks of treatment with Peptide 6, animals were injected with BrdU (2 daily i.p. injections, 75 mg/Kg/dose, 5 days) to investigate neurogenesis. After 4 weeks of chronic treatment with Peptide 6, animals were first submitted to a general behavioral battery, and then cognitive tests were carried out, as illustrated in FIG. 3(b).

The elevated plus-maze consisting of four arms (30×5 cm) connected by a common 5×5 cm center area was used. All arms and the central area were constructed with dark opaque Plexiglas. Two opposite facing arms were open (OA), whereas the other two facing arms were enclosed by walls (CA, 20 cm height). The entire plus-maze was elevated on a pedestal to a height of 82 cm above floor level. Ambient luminosity was maintained at 60 Lux to control the anxiogenic feature of light for rodents. During a single 8-min session, an animal was placed onto the central area. A videotracking system detected the presence of the animal and the time it spent in the different zones of maze-arms. Between each session, any feces were cleared from the maze, and the maze floor was cleaned with 70 percent alcohol to remove any urine or scent cues. For each animal, the number of CA entries, OA entries, and amount of time spent in CA and OA were recorded. As OA are more anxiogenic for rodents than CA, the percentage of time spent in OA was calculated to evaluate anxiety-like behavior of animals. The percentage of time spent in OA corresponds to the ratio of the time spent in OA compared to the time spent in all arms (OA+CA).

Testing on accelerating Rotarod was conducted by giving each mouse two sessions of three trials each with the motor in accelerating mode (factory settings). In this mode, the rotating speed increased steadily, at a rate of 0.02 cm/s, from 4 to 40 rpm. The latency to fall off the Rotarod was calculated. Inter-trial intervals were 10-15 min for each mouse.

An open-field and one-trial object recognition test was also used. The testing apparatus was a classic open field, i.e., a PVC square arena, 50×50 cm, with walls 40 cm high. The open field was placed in a part of the room separated from the experimenter with a black opaque curtain. The open field was surmounted by a video camera connected to a computer. Three different objects were employed in this task. The general procedure consisted of three different phases: a familiarization phase (two sessions of 15 min each), a sample phase, and a test phase. On the first and second days, mice were individually submitted to the familiarization sessions during which they were introduced in the empty arena in order to become familiar with the apparatus and eventually to observe exploratory behavior (measuring the distance covered in the open-field and the time spent in the center of the arena). On the third day, animals were first submitted to the sample phase for which two identical objects were placed in a symmetric position from the center of the arena. After a 15-min delay during which the mouse returned to its home cage, the animal was reintroduced in the arena to perform the test phase. The mouse was then exposed to two objects: a familiar object (previously presented during the sample phase) and a new object, placed at the same location as during the sample phase. Data collection was performed using a videotracking system (Smart version 2.0.14 software, Pan Lab/San Diego Instruments). Object discrimination was evaluated by the index: [(time spent close to the new object)/(time spent close to both old and new objects)] during the test phase.

A spatial reference memory task in a water-maze was performed in a 180-cm diameter circular tank. The pool was filled with water (21±1° C.) made opaque by adding white non-toxic paint. Acquisition started with the escape platform (13 cm diameter submerged 1 cm below water surface) in the Northwest quadrant, and each animal was given 90 seconds to find the platform. If the mouse did not find the platform in 90 seconds, it was gently guided to it. At the end of each trial, the mouse was left on the platform for 20 seconds, then dried, and returned to its home cage until the next trial. Three such acquisition trials were given on each day for four consecutive days. Each animal performed a total of 12 trials corresponding to a partial training of the spatial reference memory task. The measures of learning were the time and the distance swum to reach the escape platform. Mice behavior in the water-maze was monitored by a Samsung Digital Camera (SDC 4304) mounted to the ceiling and tracked and timed using a SMART version 2.0.14 software.

After completion of the behavioral task, animals were anesthetized with an overdose of sodium pentobarbital (125 mg/kg) and transcardially perfused with 0.1 M phosphate buffered saline (PBS). After perfusion, the brains were removed from the skull; the left hemisphere was immediately frozen in dry ice for biochemical analysis, and the right hemisphere was fixed in 4% paraformaldehyde in 0.1 M PBS for at least 24 h at room temperature. Tissues were then post-fixed in a 30% sucrose solution at 4° C. overnight. 40-μm sagittal sections of the entire hippocampus were cut on a freezing microtome. The sections were stored in glycol anti-freeze solution (Ethylene glycol, glycerol and 0.1 M PBS in 3:3:4 ratio) at −20° C. until further processing.

For immunohistochemical study, four animals per group were randomly selected. Briefly, every fifth brain section was chosen for stereological quantification of new born cells (BrdU-IR cells) and every tenth section for neuronal progenitor cells (NeuN-BrdU-IR cells). Quantification of MAP2, synaptophysin, Aβ, and phosphorylated tau were carried out every tenth section by densitometry. For immunohistochemistry studies, brain sections of four animals per group were randomly selected and analyzed.

The following primary antibodies were used: anti-BrdU (1:400; Accurate, Westbury, N.Y., USA); anti-NeuN (1:500; Chemicon, Temecula, Calif., USA); SMI52 to the adult isoforms of MAP2, MAP2a,b (1:1000; Sternberger Monoclonals, MD, USA); anti-synaptophysin SYN (1:200; Chemicon, Temecula, Calif., USA); anti-AB 4G8 (1:200; anti-AB1-40 (1:500, Invitrogen, CA, USA); antiphosphotau pSer202/pThr205 AT8 (1:500, ThermoScientific, Rockford, Ill., USA). The following secondary antibodies were used: Alexa 488-conjugated goat antimouse IgG antibody (1:500, Molecular Probes, Carlsbad, Calif., USA) and Alexa 594-conjugated goat anti-rabbit IgG antibody (1:500, Molecular Probes, Carlsbad, Calif., USA).

Neurogenesis was assessed in the DG by counting the number of BrdU-immunoreactive (BrdU-IR) and BrdU-NeuN-IR cells in various layers of the DG. The granule cell layer (GCL) was subdivided into an inner and outer half (iGCL and oGCL). The iGCL consisted of the subgranular zone (SGZ), defined as a 2-3-nuclei-thick layer bordering the inner half of the GCL adjacent to the Hilus (Hil); the outer GCL (oGCL) was defined as the half of the GCL adjacent to the molecular layer (Mol). A cell in the middle of the GCL was considered part of the SGZ, and a cell bordering the GCL in the Mol was included in oGCL counts. Mol was defined as the region between the superior limb of GCL and hippocampal fissure and between the inferior limb of the GCL and the inferior borders of the DG. Hil included the superficial polymorphic layer.

All sections were collected using the random uniform sampling scheme. For BrdU-IR cells, counting was performed using 40× oil objective of a Nikon 90i fluorescent microscope equipped with Nikon C1 three-laser confocal system and a Nikon DS U1 digital camera.

Employing principles of unbiased stereology, the optical fractionator method was used to estimate cell counts for the DG. The total number of BrdU-IR or NeuN-BrdU-IR cells (N) for each DG was estimated as: $N=\Sigma Q^{-} \times 1/tsf \times 1/asf \times 1/ssf$; where tsf was the thickness sampling fraction, asf was the area sampling fraction, and ssf was the section sampling fraction. $\Sigma Q^{-}$ was the total number of cells actually counted in the dissectors that fell within the sectional profiles of the region of interest within sampled sections. All layers of the DG described above were analyzed separately for cell counts. For each DG, at least 100 cells were counted based on coefficient of error determinations.

For BrdU-NeuN-IR cells, only GCL (consisting of SGZ and oGCL described above) was counted using 60× oil objective in every tenth section. To ensure objectivity, zstacks were collected for each double IR cell and analyzed later by generating maximum projection and 3D constructs. A cell was counted only when it showed double IR on 3D reconstructed images.

For densitometry, the region of interest was outlined on every tenth section. For MAP2 and synaptophysin, the entire area of the GCL, the CA1, and the CA3 of the hippocampus and parietal association and frontal cortices were analyzed. For immunohistochemistry with antibodies to AB and tau, only brain regions showing positive specific staining were quantified, namely the CA1 of the hippocampus and the parietal association cortex for 4G8, the frontal and parietal association cortices for anti-AB1-40, and the CA1 of the hippocampus and the subicullum for AT8. Maximum projection images were then generated based on confocal z-stacks, and the antibody staining was quantified by measuring mean pixel intensity (MPI) with the software ImageProPlus 5.0 (Media Cybernetics, Silver Spring, Md., USA)

Left cerebral hemisphere stored at −80° C. from each PBS perfused mouse was homogenized in a Teflon-glass homogenizer to generate 10% (w/v) homogenate. The homogenization buffer contained 50 mM Tris-HCl, pH 7.4, 0.25 M sucrose, 2 mM EDTA, 10 mM (3-mercaptoethanol plus the following protease and phosphatase inhibitors: 0.5 mM AEBSF, 8 µg/ml aprotinin, 10 µg/ml leupeptin, 4 µg/ml pepstatin, 5 mM benzamidine, 20 mM (3-glycerophosphate, 50 mM sodium fluoride, and 1 mM sodium vanadate. Protein concentration of each brain homogenate was determined by modified Lowry assay. The tissue homogenates were boiled in Laemmli's buffer for 5 min, and then subjected to 10% SDS-polyacrylamide gel electrophoresis, followed by transfer of separated proteins on 0.45 µm immobilon for Western blots. The blots were developed with a pan tau antibody, mouse mono-clonal antibody (mAb) Tau-5 (1:2,000; Millipore, Bedford, Mass., USA), human-specific mAb 43D (0.5 µg/ml; Grundke-Iqbal, in preparation), mAb AT270 to pThr181, mAb AT100 to pSer212/pThr214 tau (1 µg/ml; Thermo), or mAb AT180 to pThr231/pSer235 tau (1 µg/ml; Thermo). For loading control, the blots were developed with mAb to GAPDH (1 µg/ml; Abcam, Cambridge, Mass., USA). Immunoreactive protein bands were visualized with enhanced chemiluminescence (ECL) reagents (Pierce, Rockford, Ill., USA). The ECL films of the blots were scanned and analyzed using TINA 2.0 software (Raytest, Straubenhardt, Germany). Mean values for each group of animals were analyzed by t test. Differences with $p<0.05$ were considered significant.

Statistical analyses were conducted with SASv5 software (SAS Institute, Cary, N. C., USA). Data are presented as mean f SEM. For analysis involving multiple groups, ANOVA with post hoc Tukey's or Fisher's test was used. For all other comparisons (including inter-group comparisons), Student's t test was used. Differences with $p<0.05$ were considered significant.

For immunohistochemical studies, data from WT animals treated with vehicle and Peptide 6 were pooled since no significant differences were observed between these two groups.

Figure 4:
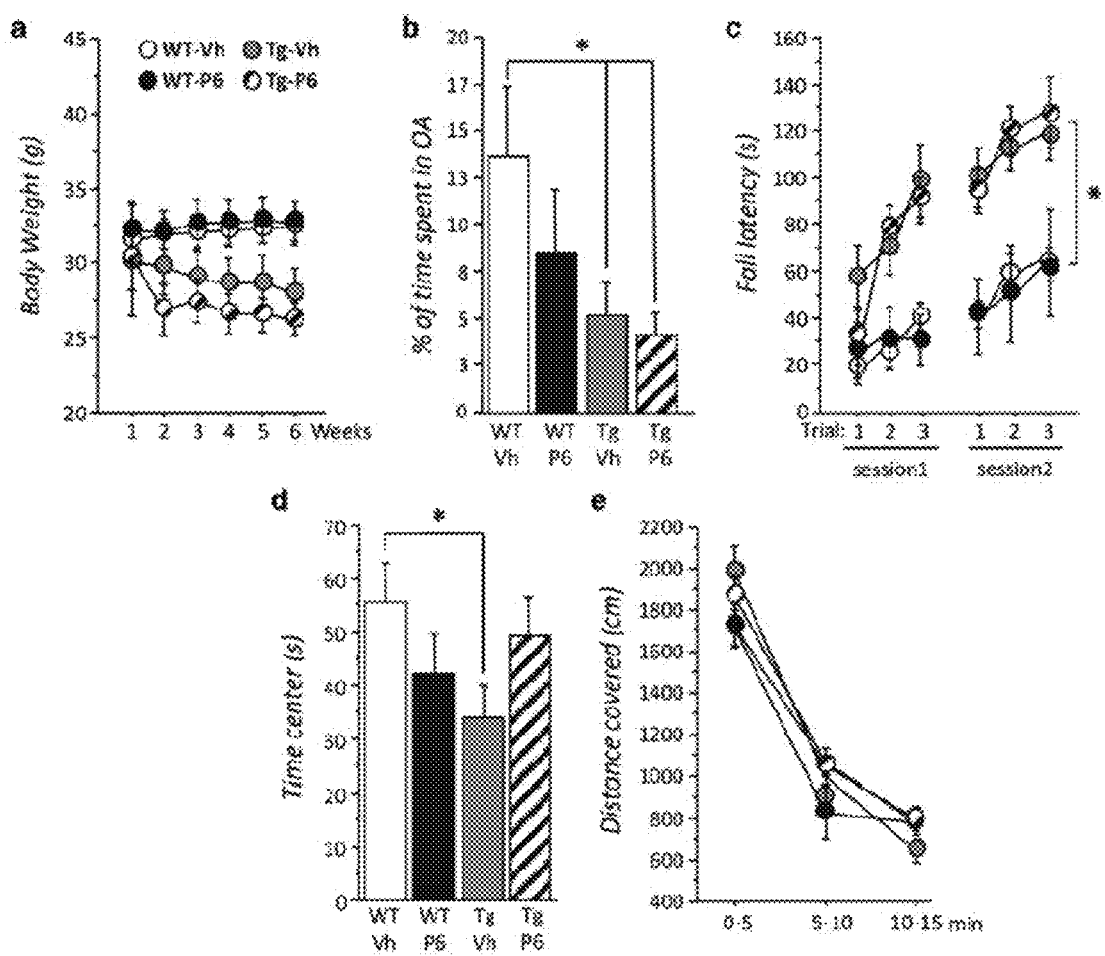
FIG. 4 is a series of graphs showing the lack of side effects induced by Peptide 6.

Since administration of the full-length CNTF protein in human clinical trials is known to cause anorexia, skeletal muscle loss, hyperalgesia, severe cramps, and muscle pain, the physical state and general behavior of animals were carefully checked throughout the period of the study. During the 6-week period of the study, animals were carefully checked and weighed once a week. No alterations in general physical state, including grooming, posture, and clasping reflex, due to either the genotype or the treatment with Peptide 6 were observed. Statistical analysis did not reveal any significant group effect (ANOVA; p=0.067) or group×week interaction (ANOVA; p=0.064) in bodyweight, as seen in FIG. 4(a). These data suggested that neither the genotype nor the treatment with Peptide 6 induced significant effect on bodyweight among groups. Anxiety was evaluated in the elevated plus-maze task. 3xTg-AD mice spent less time in OA than WT control animals treated with vehicle (marginal significant effect with ANOVA, p=0.056; post-hoc tests, p<0.013; Student's t test; p<0.046), revealing higher anxiety level for transgenic animals, as seen in FIG. 4(b). The treatment with Peptide 6 did not have any significant effect on the level of anxiety either in WT (Student's t test; p=0.317) or in 3xTg-AD animals (Student's t test; p=0.642). These data suggested that 3xTg-AD mice displayed anxiety that could not be lessened by treatment with Peptide 6. Locomotivity and motor coordination were evaluated in the accelerating Rotarod. 3xTg-AD mice displayed higher scores and improved performance faster than WT control mice, as seen in FIG. 4(c) (ANOVA; group effect: p<0.001, group×session interaction: p=0.009; post-hoc comparison; p<0.023). However, no effect of the treatment with Peptide 6 was observed in WT or 3xTg-AD mice (ANOVA; p>0.221).

During the first familiarization session of the open-field task, the tracking of animal's behavior allowed to evaluate exploratory behavior. For rodents, less time spent in the center of the arena reflects high anxiety. Measuring the time spent in the center of the arena allowed evaluation of the impact of anxiety on exploratory behavior. WT animals treated with vehicle spent significantly more time in the center of the arena than 3xTg-AD mice treated with vehicle, as seen in FIG. 4(d) (marginal significant effect with ANOVA, p=0.063; post-hoc test, p=0.010; Student's t test; p=0.035). However, no significant difference was observed between 3xTg-AD mice treated with Peptide 6 and WT animals treated with vehicle (Student's t test; p>0.141), suggesting that transgenic mice treated with Peptide 6 displayed a similar pattern of exploration as WT mice. These data suggested that anxiety of 3xTg-AD animals detected in the elevated plus-maze (see above) had repercussions on the exploration of a new environment, but that treatment with Peptide 6 minimized this effect.

To examine if animals displayed similar level of exploratory activity in a new environment, the total distance covered in the arena during the first familiarization session was analyzed in three intervals of 5 min each. All animals displayed similar level of exploration and covered comparable distance in the open field, as seen in FIG. 4(e) (ANOVA; p>0.623). These results suggested that neither the genotype nor the treatment with Peptide 6 altered general motivation for exploration of a new environment.

It is widely reported that in AD patients, during initial phases of the disease, the clinical symptoms include memory loss, particularly of recent events. In 3xTgAD mice, the onset of cognitive impairment is known to occur around 5 months of age, in advance of overt plaque and tangle pathologies, and consists of hippocampusdependent impairment of spatial memory retention.

To test whether treatment with Peptide 6 can alleviate early cognitive deficits in 3xTg-AD mice, a test for short-term memory and a hippocampal-dependent spatial reference memory was performed. In the one-trial object recognition task, animals are exposed to two different objects which they have to identify as novel or familiar based on the memory of an earlier experience with one of the two objects they encountered in the same open-field. The familiar object is explored a shorter time than the novel object because the representation of the former is still available in memory. The one-trial object recognition task tests some aspects of episodic memory, but is limited to memory of an object (what), the location of an object (where), and the context in which it was encountered (which). However, the temporal dimension of the episode remains inaccessible to the experimenter, and because of this reason this task in animals is considered a test of short-term memory. The one-trial object recognition task is thought to critically depend on the entorhinal cortex, hippocampus, and frontal cortex. During the sample phase of the task, see FIG. 5(a), all groups spent the same percentage of time close to each object, i.e. all animals explored similarly both objects (ANOVA; p>0.791). However, during the test phase, See FIG. 5(b), 3xTgAD mice treated with vehicle showed significantly lower discrimination index than WT mice treated with vehicle and 3xTg-AD mice treated with Peptide 6 (ANOVA, p=0.019; post-hoc test, p<0.006). The index of discrimination was close to 0.5 for 3xTg-AD animals treated with vehicle meaning that these animals spent similar time exploring both new and familiar objects. This null preference did not reflect a lack of interest for novelty, but rather enhanced attraction for familiarity. This revealed that familiar-object representation was yet to be built and finalized, therefore requiring as much attention as the novel object to complete the encoding. In contrast, 3xTg-AD mice treated with Peptide 6 displayed a marked preference for the novel object, similar to WT control animals. This suggested that the representation of the familiar object had been fully encoded, and then was not anymore a subject of attention at the expense of the novel stimulus. These results showed that chronic treatment with Peptide 6 reversed difficulty of 3xTg-AD mice to encode object's representation, and thus, in the present experimental conditions, improved short-term memory performance.

The spatial reference memory task assesses hippocampus-dependent reference memory in rodents, requiring that mice use a spatial navigational strategy to find a fixed submerged escape platform. The hippocampal system processes information about the relationships among distal environmental cues into a spatial map where spatial coordinates of the submerged platform are encoded. The hippocampus is also crucial for memory storage, consolidation, and restitution of the spatial information. Since the Rotarod task revealed that 3xTg-AD mice displayed higher locomotivity than WT control animals, swim speed was first analyzed. 3xTg-AD mice swam faster than WT control animals, see FIG. 5(c) (ANOVA; p=0.031, post-hoc test; p<0.033). Accordingly, training performance of animals was analyzed in distance covered to reach the submerged platform, see FIG. 5(d). Statistical analysis revealed that animals in all four groups learned as evidenced by declining distance covered to reach the submerged platform across days (ANOVA; p<0.001). However, there was a significant group effect (ANOVA; p=0.049), and post-hoc analyses revealed that 3xTg-AD mice treated with vehicle covered more distance than the three other groups to reach the submerged platform (posthoc test; p<0.026). These results suggested that 3xTg-AD mice treated with vehicle had difficulties to precisely encode, store, and/or remember the spatial coordinates of the platform within the environment as previously demonstrated. In contrast, 3xTg-AD mice treated with Peptide 6 displayed similar performance as WT controls, suggesting that the treatment with the peptide restored spatial and memory capabilities of 3xTg-AD mice to WT control levels.

Since the present Example demonstrated the reversal of cognitive impairment by treatment with Peptide 6 in 6-7 month-old 3xTg-AD mice, which is several months before these animals develop any Aβ plaques or neurofibrillary tangles, the effect of this peptide on neurogenesis and neuronal plasticity was investigated. In 3xTg-AD mice treated with vehicle, the number of BrdU-IR cells was dramatically decreased in the SGZ compared to WT animals, see FIG. 6(a); ANOVA, p=0.010, post-hoc test, p=0.003). In contrast, in 3xTgAD mice treated with Peptide 6, the number of BrdU-IR cells was increased compared to 3xTg-AD mice treated with vehicle (post-hoc test, p=0.056; Student's t test; p=0.033; 52% increase) and not significantly different to WT controls (post-hoc test, p=0.155). Considering the different sublayers of the SGZ, it appeared that in the iGCL, see FIG. 6(b), the marked decrease of the number of BrdU-IR cells in 3xTg-AD mice treated with vehicle compared to WT animals (ANOVA, p=0.004, post-hoc test, p=0.001) was prevented when 3xTg-AD mice were treated with Peptide 6 (post-hoc test, p=0.026, 65% increase). In the oGCL, no difference in the number of the BrdU-IR cells was observed among groups, see FIG. 6(c) (ANOVA, p=0.592). These results suggested that the global reduction of the number of BrdU-IR cells in the SGZ of 3xTg-AD mice was due to and limited to the iGCL. This indicated a disequilibrium in the distribution of the progenitor cells within the SGZ of 3xTg-AD mice. Normally, of the total BrdU-IR cells in the GCL, only ~25% are present in the oGCL. An increase of progenitor cells in the oGCL could be a result of ectopic birth, a phenomenon referring to an abnormal and selective increase in proliferation of progenitors in the oGCL which may cause abnormal connectivity. Statistical analysis conducted on the calculated index of ectopic birth {%[oGCLBrdU-IR cells/(iGCLBrdU-IR cells+ oGCLBrdU-IR cells)]} showed that in 3xTg-AD mice this phenomenon was significantly enhanced, see FIG. 6(d), ANOVA, p<0.001, posthoc test, p<0.001) compared to WT controls. Treatment with Peptide 6 reduced ectopic birth in 3xTg-AD mice (post-hoc test, p=0.002), therefore restoring the proliferation and distribution of progenitor cells in the DG to WT animal levels (post-hoc test, p=0.651).

Finally, differentiation of newborn progenitor cells was assessed measuring the expression of the mature neuronal marker, NeuN, in the BrdU-IR cells in the SGZ. The number of NeuN-BrdU-IR cells in 3xTg-AD mice was dramatically decreased compared to WT controls, see FIG. 6(e) (ANOVA, p=0.001, post-hoc test, p<0.001). Treatment with Peptide 6 significantly increased the number of NeuN-BrdU-IR cells in 3xTg-AD mice (post-hoc test, p=0.024) to WT control level (post-hoc test, p=0.055). However, considering the percentage of BrdU-IR cells expressing NeuN, see FIG. 6(*f*), the neuronal commitment of new born progenitor cells did not differ between groups (ANOVA, p=0.403). These findings suggested that impairment of neurogenesis in 3xTg-AD mice consisted in a global reduction of proliferation and ectopic birth of progenitor cells in the SGZ, but the neuronal commitment of the progenitor cells was not altered. Moreover, the chronic treatment with Peptide 6 successfully rescued these neurogenic abnormalities in 3xTg-AD mice.

Synapse loss, as reflected by changes in the presynaptic marker synaptophysin, correlates better with cognitive deficits than either plaques or tangles in AD patients. 3xTg-AD mice develop dysfunction in synaptic plasticity by 6 months of age, including deficits in LTP and paired-pulse facilitation. Thus, Peptide 6 was investigated to determine whether it could restore neuronal plasticity in 3xTg-AD mice by studying MAP2 and Synaptophysin density in the hippocampus and the cortex. MAP2 is a neuron-specific cytoskeletal protein involved in microtubule assembly and stabilization of dendrites, which is an essential step during neuron development. A dramatic decrease of MAP2 immunoreactivity in 3xTg-AD mice treated with vehicle was found when compared to WT mice in CA1, see FIGS. 7(*a*) and 7(*f*) (ANOVA, p=0.009, post-hoc test, p=0.004), DG, see FIGS. 7(*c*) and 7(*f*) (ANOVA, p=0.028, posthoc test, p=0.022), parietal association cortex, see FIGS. 7(*d*) and 7(*f*) (ANOVA, p=0.011, post-hoc test, p=0.006), and frontal cortex, see FIGS. 7(*e*) and 7(*f*) (ANOVA, p=0.011, post-hoc test, p=0.021), but not in CA3 of the hippocampus, see FIGS. 7(*b*) and 7(*f*) (ANOVA, p=0.454). In 3xTg-AD mice treated with Peptide 6, in all these brain areas which showed decreased MAP2 immunoreactivity, it was restored to similar levels as WT controls (post-hoc tests, p>0.078) and significantly higher than in 3xTg-AD mice treated with vehicle (post-hoc tests, p<0.013).

Synaptophysin is a glycoprotein of pre-synaptic vesicles involved in the vesicle trafficking machinery by regulating synaptic vesicle exocytosis. There was a general pattern of synaptophysin immunoreactivity which was similar to that of MAP2 immunoreactivity, as seen in FIG. 8. There was a significant decrease of synaptophysin immunoreactivity in 3xTg-AD mice treated with vehicle compared to WT controls in the CA3, see FIGS. 8(*b*) and 8(*f*) (ANOVA, p=0.028, post-hoc test, p=0.009), in the DG, see FIGS. 8(*c*) and 8(*f*) (ANOVA, p=0.146, post-hoc test, p=0.065; Student's t test, p=0.037), and in the frontal cortex, see FIGS. 8(*e*) and 8(*f*) (ANOVA, p=0.044, post-hoc test, p=0.019). But, for all brain areas studied, synaptophysin immunoreactivity was similar for 3xTg-AD mice treated with Peptide 6 and WT controls (post-hoc tests, p>0.071; Student's t tests, p>0.127). In the parietal association cortex, it was observed that synaptophysin immunoreactivity was significantly higher in 3xTgAD mice treated with Peptide 6 than in 3xTg-AD mice treated with vehicle, see FIGS. 8(*d*) and 8(*f*) (ANOVA, p=0.211, Student's t test, p=0.032).

Studies of MAP2 and synaptophysin, taken together, showed a decrease of dendritic and synaptic densities in the hippocampus and cortex of 3xTg-AD mice that could be restored by chronic treatment with Peptide 6.

In 3xTg-AD mice, intraneuronal Aβ immunoreactivity is first detectable in neocortical regions by 3-4 months of age and subsequently in CA1 pyramidal neurons by 6 months. In contrast, tau pathology occurs several months later and is first visible in the CA1 pyramidal neurons, becoming readily apparent in the hippocampus and in cortical structures by 12-15 months of age. To finally investigate whether Peptide 6 had any effect on the development of AB or tau pathology, immunohistochemical studies were conducted. To detect Aβ deposition, the antibodies 4G8 and anti-Aβ1-40 were used. To detect tau phosphorylation, the antibody AT8 was used, which recognizes tau phosphorylated at serine 202/threonine 205, two specific sites where the level of phosphorylation is greatly increased in AD. Because 3xTg-AD mice were 8-9 months when killed, AB and tau pathologies were observed only in specific brain areas.

Total AB load, as detected with antibody 4G8, which recognizes AB as well as (3APP), was significantly increased in the CA1, see FIG. 9(*a*) (ANOVA, p<0.001, post-hoc test, p<0.001) and in the parietal association cortex, see FIG. 9(*b*) (ANOVA, p=0.018, post-hoc test, p<0.036) of 3xTg-AD mice compared to WT controls. However, no significant effect of the treatment with Peptide 6 on AB in 3xTg-AD mice (post-hoc test, p>0.493) was detected. Immunohistochemistry using anti-AB1-40 showed significant ABx-40 accumulation in 3xTg-AD mice only in the frontal cortex, see FIG. 9(*c*) (ANOVA, p<0.001, post-hoc test, p<0.001) and in the parietal association cortex, see FIG. 9(*d*) (ANOVA, p=0.018, post-hoc test, p<0.036) when compared to WT controls. Treatment with Peptide 6 had no significant effect on this Aβ pathology in 3xTg-AD mice (post-hoc test, p>0.493 and Student's t tests, p>0.082).

Finally, immunohistochemistry with tau antibody AT8 revealed specific immunoreactivity in the subiculum, see FIG. 9(*e*), and in the CA1 of the hippocampus, see FIG. 9(*f*), of 3xTg-AD mice, but no effect of treatment with Peptide 6 was observed (ANOVA, p>0.812).

As expected, Western blots developed with the humanspecific tau antibody 43D showed human tau expression only in 3xTg-AD, but not the control mice, as seen in FIG. 10(*a*). Quantification of the blots developed with pan tau antibody Tau-5 normalized with the GAPDH immunostaining as a loading control showed expression of tau in all animals, see FIG. 10(*a*), and increase in 3xTg-AD mice, see FIG. 10(*b*) (ANOVA, p<0.001, post-hoc, p<0.006). The 8-9-month-old 3xTg-AD mice examined in this study did not show any detectable increase in the abnormal hyperphosphorylation of tau at pThr181, pThr212/pSer214, or pThr231/pSer235 when the immunoreactivities observed with the phosphotau antibodies were normalized with pan tau antibody Tau-5 corrected for equal protein loading by GAPDH blots, see FIGS. 10(*c*)-10(*e*). Furthermore, treatment with Peptide 6 had no significant effect on the abnormal hyperphosphorylation of tau at any of the sites studied either in 3xTg-AD or control mice.

These results showed that treatment with Peptide 6 did not have any significant effect on AB and tau pathologies, but showed their levels in 8-9-month female 3xTg-AD mice.

In the race to discover AD-directed efficient pharmacological therapy, the most popular approach is to inhibit neurodegeneration by inhibiting or clearing accumulation of Aβ peptide and hyperphosphorylated tau protein. But, beside these two key pathological hallmarks of AD, several mechanisms are compromised in AD brain, among which are neurogenesis and neuronal plasticity. Given the multifactorial nature of Aβ and tau pathologies and possible interactions between these two lesions, it is exceedingly tempting to investigate restoration of cognition by shifting the balance from neurodegeneration to neurogenesis and neuroplasticity by employing the regenerative capacity of the brain. In AD mouse models, conflicting observations have been reported regarding the level of neurogenesis, but significant decrease of neurogenesis is generally observed in models overexpressing APP. The present invention demonstrated impairment of neurogenesis and neuroplasticity and associated cognitive deficits in 3xTg-AD mice several months before these animals develop Aβ plaques or neurofibrillary tangles. Furthermore, more importantly, the present invention demonstrated, by peripheral administration of an 11-mer CNTF peptide (Peptide 6), restoration of cognition associated with enhanced neuro-genesis and neuronal plasticity in the 3xTg-AD mouse model of AD. These findings suggest that pharmacological rectification of neurogenesis and neuronal plasticity can rescue early AD-like associated cognitive deficit, opening up a new approach for therapy of this disease and other neurodegenerative disorders.

The significance of the present invention, however, lies in the use of a druggable peptide, resembling a biologically active region of CNTF, which can be administered peripherally and is effective at a nanomolar level and in a temporally and spatially controlled manner. Another important aspect of the present invention is that Peptide 6 improved cognition but without inducing severe side effects like its parent molecule. Treatment with Peptide 6 did not induce any side effect since it neither amplified modifications of general behavior due to transgenicity nor induced new alterations. Although chronic treatment with Peptide 6 could not directly reverse increased anxiety in 3xTg-AD mice in the elevated plus-maze, it did however, have a positive effect on exploratory activity in the open-field, adjusting exploration pattern similar to that of WT control animals. Effect of Peptide 6 on anxiety was mild since it was observed only during the free exploration of the open-field, but not in the elevated plus-maze task which is more anxiogenic than the former. But this effect of treatment with Peptide 6 lessening the impact of anxiety to explore a novel environment is important to consider since exploration of the environment is a crucial step at the beginning of a learning and memory task due to the impact of the context in hippocampus-dependent memory. Chronic treatment with Peptide 6 significantly enhanced two different cognitive mechanisms early impaired in both AD patients and in 3xTg-AD mice, i.e. the short-term capability to encode and remember new information and declarative memory modeled as spatial reference memory in rodents.

In the present Example, a significant decrease of MAP2 immunoreactivity was observed and, although significance was not reached in all brain areas studied, there was a strong tendency toward reduced synaptophysin immunoreactivity in 3xTg-AD mice. These observations reflected dendritic loss and synaptic pruning accounting for altered synaptic plasticity in 3xTg-AD mice and corroborated previous report of altered basal synaptic transmission (reduced maximum fEPSPs) and reduced LTP. However, chronic treatment with Peptide 6 reversed this neuroplastic failure. Thus, Peptide 6 may be ameliorating the homeostasis of the brain milieu and optimizing the micro-environment for neuronal proliferation, synaptogenesis, and neurotrophy. Therefore, since newly born mature cells have an inherent advantage of being recruited into patterns of memory networks, Peptide 6 might have promoted functional neural integration into networks, thereby strengthening biological substrates of memory processing in 3xTg-AD mice, reversing cognitive impairment. Despite absence of overt pathology, i.e., plaques and tangles, intraneuronal accumulation of Ab in the cortex and CA1 of the hippocampus and hyperphosphorylated tau at serine 202/threonine 205 in the subicullum and the CA1 of the hippocampus of 3xTg-AD mice were detected. This spatial distribution of pathological hallmarks of the AD-like pathology agreed with previous descriptions of this mouse model and confirmed that the study was conducted on an early stage of the AD-like pathology. No effect of Peptide 6 was observed on Aβ deposition and tau hyperphosphorylation although these pathologies were detected in hippocampal and cortical areas which are involved in the cognitive functions tested and restored with Peptide 6. These findings suggested that the dysregulation and disequilibrium of neuronal plasticity precedes the formation of Aβ plaques and neurofibrillary tangles in AD-like etiopathogenesis, and that restoration of cognition by pharmacologic regeneration of the brain is a feasible therapeutic approach for AD and other neurodegenerative disorders.

Example 3

All in vivo studies for characterization of peptides (stereology and behavioral analysis) were performed on 8-10-month-old female retired breeders of C57B16 background. The animals were acclimatized for at least 3 weeks to exclude occasional pregnant mice from the studies. Mice were group-housed (3 animals per cage) with a 12:12 light:dark cycle and with free access to food and water. All procedures were conducted in accordance with approved protocols from our institutional Animal Welfare Committee.

Based on Peptide 6, a set of four tetrapeptides with overlapping residues to the sequence of the parent peptide CNTF 6 (see Table 3) was further constructed. These peptides, CNTF 6a-d, were synthesized on a commercial basis by the Pan Biotechnology Facility of Stanford University (Palo Alto, Calif.).

TABLE 3

| CNTF Peptide | Position in CNTF |
|---|---|
| Peptide 6a | 145-148 |
| Peptide 6b | 146-149 |
| Peptide 6c | 147-150 |
| Peptide 6d | 148-151 |

To study neurogenesis, mice received subcutaneous implants of extended release depot pellets containing either CNTF pep-tides 6a or 6c for 30 days of continuous dosing (Innovative Research of America, Sarasota, Fla.). For control groups, the pellets consisted of the carrier biopolymer only. For implantation, the mice were anesthetized with 2.5% Avertin (0.38 ml for a 25 g animal). Under sterile conditions, the pellets were then subcutaneously implanted along the anterolateral aspect of the right shoulder with a precision trochar (Innovative Research of America). The animals were then transferred to the animal colony after recovery from anesthesia. There were no complications associated with the implantation and treatment. BrdU was given as two daily i.p. injections (100 mg/kg/dose) for five days starting on day 2 of peptide treatment. Neurogenesis was assessed in the dentate gyrus (DG) by counting the number of BrdU-immunoreactive (BrdU-IR), BrdU-DCX-IR and BrdU-NeuN-IR cells in various layers of the DG. Employing principles of unbiased stereology, the optical fractionator method was used to estimate cell counts for the DG.

The following primary antibodies were used for immunohistochemistry: anti-BrdU (1:400; Accurate) a rat monoclonal raised against BrdU; anti-DCX (1:200; Santa Cruz Biotechnology Inc.), a goat polyclonal antibody raised against an 18-amino acid peptide representing residues 384-410 of human doublecortin; anti-NeuN (1:500; Chemicon), a mouse monoclonal antibody raised against purified cell nuclei from mouse brain; Anti-c-Fos (Ab-5) (1:500; Calbiochem), a rabbit polyclonal antibody raised against a synthetic peptide corresponding to amino-acids 4-17 of human c-Fos; SMI52 (1:1000; Sternberger Monoclonals), a mouse monoclonal antibody specific for the mature neuronal marker MAP2a,b; antisynaptophysin, SYN (1:200; Chemicon), a mouse monoclonal antibody raised against vesicular fraction of bovine brain. The following secondary antibodies were used: Alexa 488-conjugated goat anti-mouse IgG antibody and Alexa 594-conjugated goat anti-rabbit or anti-rat IgG antibody (Molecular Probes); biotinylated anti-rat IgG antibody and Cy5-conjugated goat anti-mouse antibody (Jackson ImmunoResearch).

At the end of treatment, all animals were anesthetized with an overdose of sodium pentobarbital and transcardially perfused with 0.1 M PBS. After perfusion, the brains were removed from the skull, the left hemisphere was immediately frozen for future biochemical analysis and the right hemisphere was fixed in 4% paraformaldehyde in 0.1 M PBS for at least 24 hours at room temperature. Tissues were then stored in 30% sucrose solutions at 4° C. until sectioning. The brains were sectioned sagittaly on a freezing sliding microtome at 40 pm through the entire hippocampus and the sections were stored in glycol anti-freeze solution (Ethylene glycol, glycerol and 0.1 M PBS in 3:3:4 ratio) at −20° C. till further processing.

Immunohistochemistry was performed as described elsewhere (Kuhn et al., J. Neurosci 17 (15) (1997): 5820-5829). Briefly, every 5th brain section was chosen for quantification of cell number and every 10" section was chosen for staining intensity scanning. Immunohistochemistry was performed on free floating sections. For BrdU immunohistochemistry, epitope retrieval and staining were performed as previously described (Kuhn et al., J. Neurosci 17 (15) (1997): 5820-5829).

Neurogenesis was assessed in the DG by counting the number of BrdU-immunoreactive (BrdU-IR), BrdU-DCX-IR and BrdU-NeuN-IR cells in various layers of the DG. The granule cell layer (GCL) was subdivided into an inner and outer half (iGCL and oGCL). The iGCL consisted of the subgranular zone (SGZ, defined as a 2-3 nuclei thick layer bordering the GCL) and the inner half of the GCL adjacent to the Hilus (Hil); the outer GCL (oGCL) was defined as the half of the GCL adjacent to the Molecular layer (Mol). A cell in the middle of the GCL was considered part of the iGCL and a cell bordering the GCL in the Mol was included in oGCL counts. Mol was defined as the region between the superior limb of GCL and hippocampal fissure and between the inferior limb of the GCL and the inferior borders of the DG. Hil included the superficial polymorphic layer.

All sections were collected using the random uniform sampling scheme. For BrdU-IR cells, counting was performed on every 5th section using 40× oil objective of a Nikon 90i fluorescent microscope equipped with Nikon C1 three laser confocal system and a Nikon DS U1 digital camera. Employing principles of unbiased stereology, the optical fractionator method was used to estimate cell counts for the DG (West et al., Anat Rec 231 (1991): 482-497). All layers of the DG described above were analyzed separately for cell counting. For each brain, at least 100 cells were counted based on coefficient of error determinations.

For BrdU-DCX-, BrdU-NeuN-, and c-Fos-NeuN-IR cells, only GCL (consisting of iGCL and oGLC described above) was counted using 100× oil objective in every 10th section. To ensure objectivity, z stacks were collected for each double IR cell and analyzed later by generating maximum projection and 3D constructs. A cell was counted only when it showed double IR on 3D reconstructed images.

For MAP2 and Synaptophysin IR, the entire area of GCL was outlined on every 10th section. Maximum projection images were then generated based on confocal z stacks, and the antibody staining was quantitated by measuring mean pixel intensity (MPI) with the help of Image-Pro Plus 5.0 software (Media Cybernetics).

All quantitations based on immunohistochemistry were verified independently on coded slides by a second investigator.

For behavioral studies, performance on the Morris Water Maze task was assessed in three groups of 10 mice each (placebo, CNTF6a and CNTF6c) which received peptide treatment for 30 days. To avoid daily stress due to injections, all animals undergoing behavioral studies received subcutaneous implants of CNTF 6a, CNTF 6c or placebo pellets as described above.

All animals for behavioral testing were coded such that the experimentator was blind to the assignment of the animals to specific treatment groups. The Morris Water Maze procedure was performed using a 110 cm diameter circular tank. Before training, the mice were handled gently for 2-3 min/day during 3 days to minimize non-specific stress. Acquisition was started with the submerged (invisible) escape platform in the North-East quadrant and each animal was given 60 sec to find the submerged escape platform. If the mouse did not find the platform in 60 sec, it was guided to it. Five such acquisition trials were given on each day, for four consecutive days. A test for retention, or probe trial, was given 24 hours later. During the probe trial the mouse was allowed to swim in the tank without the escape platform for 60 seconds. This was followed by second and third probe trials 15 and 30 days from the first probe trial. Each probe trial was immediately followed by a "retraining session" consisting of 5 trials/animal to consolidate learned behavior.

The measures of learning were the time and distance swum to reach the escape platform. For retention during the probe trial, the tank was divided into four imaginary quadrants and a small zone where the escape platform had been (virtual platform). The measures of retention were the percent of time spent and the percent of distance swum in each quadrant, and the number of entries into the platform zone.

Mouse behavior in the Morris Water Maze was monitored by a Samsung Digital Camera (SDC 4304) mounted to the ceiling and tracked and timed by a SMART (Pan Lab/San Diego Instruments) version 2.0.14 software.

Data are represented as mean±SEM. For analysis involving multiple groups, ANOVA with post hoc Tukey's test was used. For analysis of data with skewed distributions, the non-parametric Mann-Whitney U-test was used. For all other comparisons (including inter-group comparisons), Student's t-test was used. Differences with $p<0.05$ were considered significant.

The four CNTF tetrapeptides were initially screened in a behavioral paradigm employing the Morris Water Maze. Two CNTF tetrapeptides, CNTF 6a and CNTF 6c, were chosen for detailed stereological and behavioral analysis.

Figure 11:
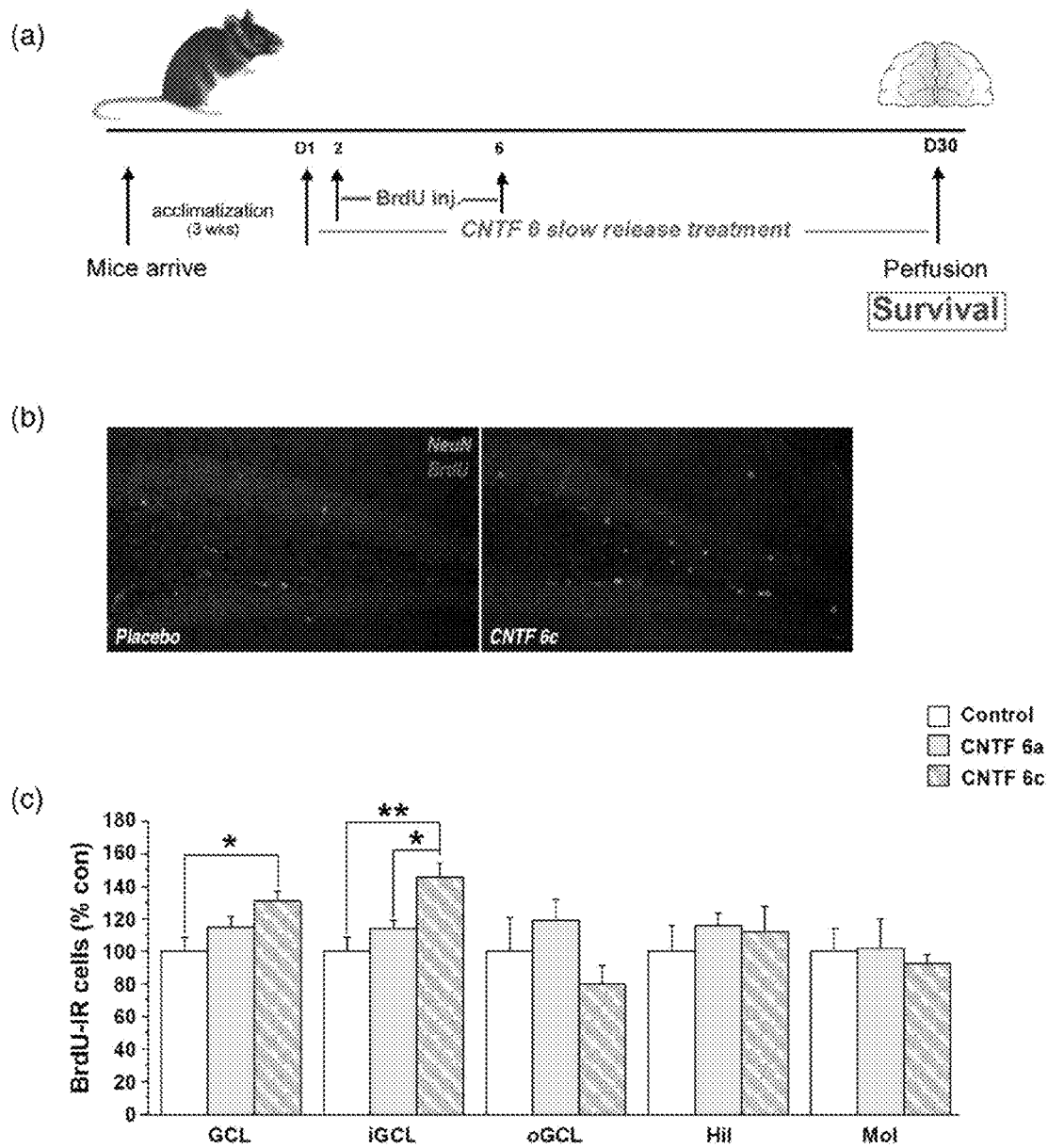

Fifteen mice were divided into 3 groups including placebo, CNTF 6a and CNTF 6c. Mice received subcutaneous implants of 30-day extended release pellets containing either CNTF 6a or CNTF 6c (50 nmol/peptide/animal/day, n=5/group) or placebo (n=5). Referring to FIG. 11(*a*), dividing cells were labeled with BrdU given i.p. for five days, twice a day (100 mg/kg/animals/dose). Compared to the placebo group, CNTF 6c increased BrdU-immunoreactive (BrdU-IR) cell counts in the GCL by 31% ($p<0.05$, Student's t-test). CNTF 6a had not significant effect on cell proliferation in the GCL, as seen in FIGS. 11(*b*) and 11(*c*) and Table 2.

Further examination of the proliferation in four sub-regions of the hippocampus (for anatomical definitions, see "Materials and Methods" section): iGCL (inner granule cell layer, which included the SGZ), oGCL (outer granule cell layer, Mol (molecular layer) and Hil (hilus), revealed that compared to control group, CNTF 6c increased the number of BrdU-IR cells in the iGCL by 45% (p<0.001, Student's t-test), whereas no significant differences were observed in either oGCL, Mol or Hil, see FIGS. 11(b) and 11(c), and Table 4. CNTF 6a had no effect on BrdU-IR cell numbers in either of the four sub-regions of the DG. Together, these data suggest that both CNTF 6c increased BrdU-IR cells in the DG and this increase was mainly confided to the iGCL, the neurogenic niche of the hippocampus.

TABLE 4

Stereological counts (±SEM) of BrdU-IR cells in various subregions of the hippocampus in 30-day treated mice (n = 5/group)

|  | GCL | iGCL | oGCL | Mol | Hil |
| --- | --- | --- | --- | --- | --- |
| Control | 427 ± 38 | 334 ± 28 | 93 ± 19 | 526 ± 77 | 108 ± 17 |
| CNTF 6a | 493 ± 28 | 382 ± 15 | 110 ± 13 | 538 ± 99 | 126 ± 8 |
| CNTF 6c | 560 ± 24 | 486 ± 31 | 74 ± 10 | 487 ± 28 | 121 ± 16 | p<0.05, p<0.01. Student's T-Test

Doublecortin (DCX), an immature neuronal marker, is used to quantitate early neuronal fate determination in DG progenitors. The number of DCX-IR cells in the GCL (iGCL+oGCL) was quantitated at the time of perfusion, a snapshot-quantitation of immature neurons in response to 30-day treatment with CNTF tetrapeptides, as seen in FIG. 12(a). Stereological analysis revealed that compared to the placebo, CNTF 6c treatment increased DCX-IR cells in the GCL by almost 2 folds (~91%, increase, p<0.001, Student's t-test), whereas CNTF 6a treatment did not show any significant difference as seen in FIG. 12(a) and Table 5). These data suggest that at the time of perfusion, there were more immature neurons in the GCL of CNTF 6c treated animals. Whether this also reflects early neuronal differentiation of dividing progenitors cannot be determined by our study.

TABLE 5

Stereological counts (±SEM) of cells expressing various neuronal maturity and/or activity markers in the granule cell layer of the dentate gyrus in 30-day treated mice (n = 5/group)

|  | DCX | NeuN-BrdU/BrdU | c-fos-NeuN |
| --- | --- | --- | --- |
| Control | 306 ± 72 | 24 ± 2 | 168 ± 17 |
| CNTF 6a | 360 ± 33 | 19 ± 2 | 214 ± 27 |
| CNTF 6c | 656 ± 43 | 39 ± 2 | 247 ± 23 | p<0.05, p<0.01 Student's T-Test

Net neurogenesis in the DG is determined by the number of progenitors which survive as mature neurons, as more than half of the progenitors either die as stem cells or as immature precursors (eg. DCX-IR cells). In order to determine whether CNTF 6c induced differentiation of DG progenitors into mature neurons, the number of BrdU-IR cells expressing the mature neuronal marker NeuN in the GCL of the DG was counted. A 62% increase in BrdU-NeuN-IR cells in CNTF 6c treated animals was found when compared with the placebo group, whereas CNTF 6a treatment had no effect (p<0.01, Student's t-test; FIG. 12(b) and Table 5).

For neurogenesis to have physiological significance, newly born neurons need to be functionally integrated into the hippocampal circuitry. Neuronal activity, an indication of functional integration, can be indirectly quantitated by studying changes in the expression of immediate-early genes like c-fos and zif. Towards that aim, it was investigated whether CNTF6c induced an increase in c-fos protein expression, providing a biological substrate for neuronal firing, and ultimately spatial encoding. Stereological counts of c-fos expressing mature DG neurons without behavioral stimulation, i.e. at basal levels reflecting activity in the cage (FIG. 13(a) and Table 5) were compared. It was found a ~47% increase in the number of mature neurons (NeuN-IR) co-expressing c-fos in the GCL in CNTF 6c treated mice (p<0.05, Student's t-test). There was also evidence of increased neuronal activity in newly born mature neurons as some BrdU-NeuN-IR cells in the GCL also co-expressed zif, as seen in FIG. 13(a).

Microenvironment within the brain undergoes significant changes in both aging and disease. The rate of neurogenesis and synaptogenesis in the brain indirectly reflect its microenvironment. In order to study whether CNTF 6c-induced enhancement of DG nerogenesis was also accompanied by changes in local neurotrophy, the expression of MAP2 and synaptophysin, indicators of dendritic arborization and synaptic activity respectively, in the GCL of treated animals was measured. An increase in both indicators of neurotrophy (31% and 26% respectively, p<0.01, Student's t-test) as measured by mean-pixel intensity was found, as seen in FIG. 13(b).

Increased neuronal differentiation of DG progenitors, enhanced neuronal firing, upregulated synaptogenesis and neurothrophy are all key biological substrates of memory processing within the DG. Therefore, it was evaluated whether CNTF 6c treatment also had an effect on the cognitive function of treated animals. Since normal adult mice were used as experimental animals, it was crucial not to miss any effect on memory acquisition and learning that the 30-day peptide treatment might have had. Therefore, a partial training paradigm was used to evaluate learning and memory in the Morris Water Maze. Treated mice were trained on the Morris Water Maze for a total of 20 sessions spanning 4 days after which they were subjected to the first probe trial (P1). Two additional probe trials (P2 and P3) were administered 15 and 30 days after P1. Each probe trial was immediately followed by 4 retraining sessions to allow memory consolidation, as seen in FIG. 14(a). Learning was evaluated in terms of latency and distance traveled to reach the invisible escape platform. Retention was measured on probe trials by the percent of time and travel distance in the target quadrant, and the number of crossings of the virtual platform.

Animals in all three groups learned well as evident by declining swim latencies to reach the submerged platform, as seen in FIG. 14(a). However, there was no effect of either CNTF 6a or CNTF 6c treatment on learning in the spatial reference memory task (two way ANOVA, p=0.667).

Analysis of retention on the three probe trials showed no effect of the treatment on P1, whereas P2 and P3 showed significant differences in both measures of retention in CNTF 6c treated mice. Analysis of time spent in the target quadrant across three probe trials indicated that whereas all animals spent equal amount of time on P1, both placebo and CNTF 6a treated animals reduced this time during subsequent P2 and P3. CNTF 6c-treated animals however, spent the same percent amount of time in the target quadrant during the three probe trials, indicating better preservation of the memory trace in these mice, as seen in FIG. 14(b). Analysis of the percent distance traveled within the target quadrant also presented a similar picture for CNTF 6c across the three probe trials, as seen in FIG. 14(c).

Example 4

In the foregoing Examples it was shown that an 11-mer peptide, Peptide 6 (Ac-VGDGGLFEKKL-NH$_2$) and a subsequence of it, Peptide 6c (Ac-DGGL-NH$_2$), enhanced hippocampus dependent learning and memory, increased neurogenesis and neuronal plasticity in normal adult mice. Although peptides in general are readily bioavailable, systemic degradation through proteases and relatively poor blood-brain-barrier (BBB) permeability pose challenges in rendering peptides "druggable." To address these design goals, adamantane building blocks were added to the C-terminus or both C- and N-termini of Peptide 6c. These bulky, highly lipophilic tricyclic alkane building blocks can increase the BBB permeability of peptides and block enzymatic degradation through exopeptidases. In the present example, it could be shown that when administered peripherally to normal adult mice, the pentamer Ac-DGGL$^A$G-NH$_2$, called P21, significantly enhanced cognition, increased proliferation and differentiation of adult hippocampal progenitors and promoted the expression of synaptic vesicle proteins, synaptophysin and synapsin I.

FIG. 15 shows the design and structures of peptidergic compounds employed in this example. For synthesis of peptidergic compounds incorporating adamantane building blocks, compounds P21 (Ac-DGGL$^A$G-NH$_2$) and P22 (1-Ad-CO-DGGL$^A$G-NH$_2$), animals and housing, one trial object recognition test, spatial reference memory task in the water maze, immunohistochemistry, cell counts by stereology, analysis of the mechanism of action of P21 through LIF receptor in HepG2 cells, and statistical analysis.

Peptidergic compounds Ac-DGGL$^A$G-NH$_2$ (P21) and 1-Ad-CO-DGGL$^A$G-NH, (P22) (FIG. 15) were synthesized by standard solid phase peptide synthesis (SPPS) methods following the Fmoc-strategy. 3-(9-Florenylmethoxycarbonyl)aminoadamantane-1-carboxylic acid (Fmoc-$^A$Gly) was synthesized as described previously (Wanka, L., et al. Eur J Org Chem 9 (2007): 1474-1490). Fmoc-a-amino acids, activation reagents and other chemicals used were purchased from EMD Chemicals (Gibbstown, USA) and used as supplied. Solvents used were peptide synthesis grade. Manual SPPS was performed on Rink amide AM resin (200-400 mesh, Novabiochem) in a peptide synthesis vessel. Loading (2×1 h) as well as chain elongation (2×45 min) were performed via double-couplings using 2×3 equivalents (over resin substitution) of the respective Fmoc-amino acid, 2-(1HBenzotriazole-1-yl)-1,1,3,3-tetramethylaminium hexafluorophosphate (HBTU), and 1-Hydroxybenzotriazole (HOBt), and 2×6 equivalents of N,N-diisopropylethlamine (DIPEA). Acetylation was performed using 10 equivalents of acetic anhydride and DIPEA over resin loading for 30 min Adamantanoylation was performed using adamantane-1-carboxylic acid (Acros Organics, Belgium) in a double-coupling procedure with HBTU/HOBt activation as described above for the chain elongation steps. Removal of the temporary Fmoc-protective group was performed using 20% piperidine in N,N-dimethylformamide (DMF, 2×20 min). After each chain elongation and Fmoc-cleavage step, the resin was washed with DMF (5×1 min), dichloromethane (DCM, 5×1 min), and DMF (3×1 min). The peptides were cleaved from the resin with trifluoroacetic acid (TFA)/water/triisopropylsilane (95:2.5:2.5) for 3 h and precipitated by the addition of ice-cold diethyl ether. They were collected by centrifugation. The crude precipitates were resuspended in fresh ice-cold diethyl ether and centrifuged another two times. After dissolving in water/acetic acid (2:1) and extraction with diethyl ether/hexanes (1:1), the aqueous solution of the crude peptides was lyophilized. The peptides were purified by semi-preparative reversed-phase HPLC using a Waters DeltaPak RP18 column (19×300 mm, 5 nm, 300 Å) and gradients of solvent B in solvent A (A: water, 0.1% TFA; B: acetonitrile, 0.1% TFA) at 5 mL/min flow rate. Product fractions were analyzed by analytical HPLC using an Agilent Zorbax Eclipse XDB-C8 column (4.6×150 mm), and linear gradients of solvent B in solvent A at 1 mL/min flow. Both analytical and semipreparative HPLC were monitored at 220 nm using a variable wavelength detector. Product fractions containing the peptides in >95% purity as analyzed by analytical HPLC were pooled, lyophilized and used for the present study. Proton NMR spectra were recorded on a Varian 600 spectrometer. Proton chemical shifts are reported in ppm (δ) relative to internal tetramethylsilane (TMS, δ 0.0 ppm).

Data are reported as follows: chemical shift (multiplicity [singlet (s), doublet (d), triplet (t), quartet (q), multiplet (m)], coupling constants [Hz], integration). The spectra were obtained at 25° C. ESI-MS spectra were recorded on an Agilent 1100 series MSD instrument.

The HPLC and NMR data of P21 and P22 are as follows:

Ac-DGGL$^A$G-NH$_2$ (P21) (SEQ ID NO:12): Preparative HPLC: 15-45% solvent B in solvent A in 80 min, product fractions eluted at 40-43 min Analytical HPLC: 10-60% solvent B in solvent A in 20 min , rt=9.5 min 1H-NMR (600 MHz, [D6]DMSO): δ=0.83 (d, J=6.5 Hz, 3H, Leu-H δ); 0.87 (d, J=6.6 Hz, 3H, Leu-H δ); 1.36-1.47 (m, 2H, Leu-H β); 1.49-1.59 (m, 3H, Leu-Hγ and adamantane-CH$_2$); 1.62-1.71 (m, 4H, 2×adamantane-CH$_2$); 1.79-1.90 (m, 4H, 2×adamantane-CH$_2$); 1.86 (s, 3H, acetyl-CH$_3$); 1.92 (br. s, 2H, adamantane-CH$_2$); 2.06-2.12 (m, 2H, 2×adamantane-CH); 2.70 (dd, J=16.6 and 5.4 Hz, 1H, Asp-Hβ); 3.66-3.75 (m, 5H, 4×Gly-Hα and Asp-Hβ); 4.21-4.27 (m, 1H, Leu-Hα); 4.51-4.57 (m, 1H, Asp-Hα); 6.71 (s, 1H, CONH$_2$); 6.98 (s, 1H, CONH$_2$); 7.36 (br. s, 1H, $^A$Gly-NH); 7.69 (d, J=8.4 Hz, 1H, Leu-NH); 7.99 (t, J=5.9 Hz, 1H, Gly-NH); 8.20 (t, J=5.7 Hz, 1H, Gly-NH); 8.24 (t, J=7.6 Hz, 1H, Asp-NH); 12.32 (br. s, 1H, Asp-CO$_2$H). MS (ESI): m/z=579.4 [M+H]$^+$(calcd. 579.3).

1-AdCO-DGGL$^A$G-NH$_2$ (P22): Preparative HPLC: 10-43% solvent B in solvent A in 79 min, then 43-60% solvent B in solvent A in 10 min , then 20 min at 60% solvent B in solvent A. Product fractions eluted at 83-86 min Analytical HPLC: 10-60% B in A in 20 min, rt=15.5 min 1H-NMR (600 MHz, [D6]DMSO): δ=0.82 (d, J=6.8 Hz, 3H, Leu-H δ); 0.87 (d, J=6.8 Hz, 3H, Leu-Hδ); 1.35-1.45 (m, 2H, Leu-Hβ); 1.49-1.59 (m, 3H, Leu-Hγ and adamantane-CH$_2$); 1.61-1.70 (m, 10H, 5×adamantane-CH$_2$); 1.75-1.80 (m, 6H, 3×adamantane-CH$_2$); 1.80-1.89 (m, 4H, 2×adamantane-CH$_2$); 1.92 (br. s, 2H, adamantane-CH$_2$); 1.94-1.98 (m, 3H, 3×adamantane-CH); 2.04-2.11 (m, 2H, 2×adamantane-CH); 2.56 (dd, J=16.0 and 8.0 Hz, 1H, Asp-Hβ); 2.74 (dd, J=16.1 and 5.5 Hz, 1H, Asp-Hβ); 3.66-3.75 (m, 4H, 4×Gly-Hα); 4.21-4.27 (m, 1H, Leu-Hα); 4.53-4.58 (m, 1H, Asp-Hα); 6.71 (s, 1H, CONH$_2$); 6.98 (s, 1H, CONH$_2$); 7.35 1H, $^A$Gly-NH); 7.62 (d, J=7.7 Hz, 1H, Leu-NH); 7.71 (d, J=8.5 Hz, 1H, Asp-NH); 7.88 (t, J=5.5 Hz, 1H, Gly-NH); 8.03 J=5.9 Hz, 1H, Gly-NH); 12.20 (br. s, 1H, Asp-CO$_2$H). MS (ESI): m/z=699.4 [M+H]$^+$(calcd. 699.4).

All in vivo studies for characterization of compounds (stereology and behavioral analysis) were performed on 8-10-month-old female retired breeders of C57Bl6 background. Animals were acclimatized for at least 3 weeks to exclude occasional pregnant mice from the studies. Mice were group-housed (3 animals per cage) with a 12:12 hours light/dark cycle and with free access to food and water.

For the compound treatment, mice (8 animals/group) received subcutaneous implants of extended release depot pellets containing P21 or P22 at 25 nmol/day for 35 days of continuous dosing (Innovative Research of America, USA). For the control group (8 animals), pellets consisted of the carrier polymer only. Mice were anesthetized with 2.5% Avertin (0.38 ml for a 25 g animal). Under sterile conditions, pellets were implanted subcutaneously along the anterolateral aspect of the right shoulder with a precision trochar (Innovative Research of America). After recovery of anesthesia, animals were transferred to the animal colony. No complications associated with the implantation and treatment were observed. All procedures on animals were conducted in accordance with approved protocols from our Institutional Animal Welfare Committee.

To investigate neurogenesis, BrdU (Sigma, USA) was given as two daily i.p. injections (100 mg/kg/dose) for five days starting on day 2 of compounds treatment.

The physical state and condition of animals were carefully monitored throughout the treatment by evaluating grooming, physical state and clasping reflex. Body weight was also recorded.

In the one-trial object recognition task, animals are exposed to two different objects which they have to identify as novel or familiar based on the memory of an earlier experience with one of the two objects they encountered in the same open field. The familiar object is explored shorter than the novel encountered one because the representation of the former is still available in memory. The one-trial object recognition task tests some aspects of episodic memory but is limited to memory of an object (what), the location of an object (where), and the context in which it was encountered (which). However, the temporal dimension of the episode remains inaccessible to the experimenter, and because of this reason this task in animals is considered a test of short term memory.

The testing apparatus was a classic open field (i.e. a PVC square arena, 50×50 cm, with walls 40 cm high). The open field was placed in a part of the room separated from the experimenter with a black opaque curtain. The open field was surmounted by a video camera connected to a computer. Three objects were employed in this task. The general procedure consisted of three different phases: a familiarization phase (1 session of 20 min), a sample phase, and a test phase. On the first days, mice were individually submitted to the familiarization session during which they were introduced in the empty arena in order to become familiar with the apparatus. This familiarization session allowed to record a baseline level of locomotor activity (measuring the distance covered in the open field) and of anxiety (measuring the time the animals spent in the centre of the arena during the first five minutes). On the second day each mouse was first submitted to the sample phase (session 1, ten minutes) for which two identical objects were placed in a symmetric position from the centre of the arena. After a 15 minute delay during which the mouse returned to its home cage, it was reintroduced in the arena to perform the test phase (session 2, 10 min). The mouse was then exposed to two objects: a familiar object (previously presented during the sample phase) and a new object, placed at the same location as during the sample phase. Data collection was performed using a video tracking system (Smart version 2.0.14 software. Pan Lab/San Diego Instruments).

Object discrimination was calculated as follows: OD=(time spent close to new object)/(time spent close to new object)+(time spent close to old object)×100.

Spatial reference learning and memory were evaluated in the water maze using a procedure adapted from that previously described by Morris et al. (Morris, R. G., et al. Nature 297 (1982): 681-3). The test required that mice used a spatial navigational strategy based on a spatial representation of the environment to find a fixed submerged escape platform. The procedure was performed in a 180 cm diameter circular tank. The pool was filled with water (21±1° C.) made opaque by adding white non-toxic paint. Acquisition started with the escape platform (15 cm diameter submerged 1 cm below water surface) in the Northwest quadrant and each animal was given 90 seconds to find the platform. If the mouse did not find the platform in 90 seconds, it was gently guided to it. At the end of each trial, the mouse was left on the platform for 20 seconds, then dried and returned to its home cage until the next trial. Five such acquisition trials were given on each day for four consecutive days. A test for retention, or probe trial (PT), was given 24 hours later. During the probe trial the mouse was allowed to swim in the tank without the escape platform for 60 seconds. This was followed by second and third probe trials 15 and 30 days after the first probe trial.

The measures of learning were the time and distance covered to reach the escape platform. For the probe trial, the tank was divided into four imaginary quadrants and a small zone where the escape platform had been. The measure of retention was calculated as the ratio of time spent or distance covered in target quadrant over that in the three other quadrants.

Mouse behavior in the water maze was monitored by a Samsung Digital Camera (SDC 4304) mounted to the ceiling and tracked and timed by a SMART (Pan Lab/San Diego Instruments) version 2.0.14 software.

At the end of the behavioral experiment, animals were anesthetized with an overdose of sodium pentobarbital (120 mg/kg) and transcardially perfused with 0.1 M phosphate buffered saline (PBS). After perfusion, the brains were removed from the skull, the left hemisphere was immediately frozen for future biochemical analysis and the right hemisphere was immersion fixed in 4% paraformaldehyde in 0.1 M PBS for at least 24 hours at room temperature. Tissues were equilibrated and stored in 30% sucrose solution at 4° C. until sectioning. The brains were sectioned sagittaly on a freezing sliding microtome at 40 nm through the entire hippocampus and the sections were stored in glycol anti-freeze solution (Ethylene glycol, glycerol and 0.1 M PBS in 3:3:4 ratio) at −20° C. until further processing.

For double labeling of BrdU and NeuN, brain sections were pretreated with 2 M HCl at 37° C. for 30 min and neutralized with 0.1 M borate buffer (pH 8.5) for 10 minutes. Tissue sections were incubated first for 30 min with blocking buffer (4% normal goat serum+0.1% Tween-20 in PBS) and then overnight at 4° C. in the presence of BrdU (Millipore Corporation, USA) and NeuN (Millipore Corporation) antibodies diluted 1:400 and 1:100, respectively. To determine the integrity of presynaptic terminals, tissues were labeled with anti-synaptophysin (1:200; Clone SY38, Millipore Corporation) or anti-synapsin I (1:200; Stressgen Biotechnologies Corporation, Canada). The brain sections were incubated in primary antibody overnight at 4° C., respectively. Alexa 488 and 594 (1:500; Invitrogen, USA) were used as secondary antibodies. All images were obtained using Nikon Eclipse 90i and D-Eclipse C1 microscopes (Nikon Corporation, Japan).

Neurogenesis in the dentate gyrus was evaluated by counting the number of BrdU-positive and BrdU/NeuN double-positive cells in the dentate gyrus (DG). The number of positive cells was determined in every fifth section in a series of 40 nm sagittal sections throughout the DG using unbiased stereology. All BrdU-positive cells in the subgranular zone (SGZ) and granule cell layer (GCL) were counted using a fluorescent microscope (Nikon Eclipse 90i, Nikon Corporation, Japan). Double labeled cells were assessed by a confocal imaging system (D-Eclipse C 1, Nikon Corporation). Employing principles of unbiased stereology, the optical fractionator method was used to estimate cell counts for the DG.

For each brain, at least 100 cells were counted based on coefficient of error determinations.

For quantitative analysis of the expression of synaptophysin and synapsin I in DG, every tenth section in a series of 40 nm coronal sections throughout the hippocampus was analyzed. The entire area of GCL was outlined. Maximum projection images were then generated based on confocal z-stacks, and antibody staining was quantified by measuring the mean optical density (OD) with the help of NIH Image J program, version 1.32j (http://rsb.info.nih.gov).

To investigate the molecular mechanism of action of compound P21 in LIF signaling, HepG2 human hepatoma cell (ATCC, USA) at 80% confluence were treated with different concentrations of P21 and with 0.25 nM LIF (Peprotec, Inc., USA) for 15 min The cells were lysed and subjected to Western blots developed with antibodies anti-phospho-Tyr 705 STAT3 and anti-STAT3 (Cell signaling Technology, USA).

All statistical analyses were performed with STATISTICA 6.0 (StatSoft, Inc. Tulsa, USA). Data are represented as mean±SEM. ANOVAs with post hoc Fisher LSD test were used for data analyses, except data from STAT3 phosphorylation, which were analyzed by Student's t-tests. Differences with $p<0.05$ were considered significant.

Administration of the full-length CNTF protein in human clinical trials is known to cause anorexia, skeletal muscle loss, hyperalgesia, cramps, and muscle pain. However, in the present example, no alteration in either general physical state, body weight, as seen in FIG. 16(a), exploratory behavior, as seen in FIG. 16(c), or swim speed, as seen in FIG. 16(d), during the period of the study could be observed, suggesting that treatment with compound P21 or P22 did not induce any apparent side effects. In the water maze task, no floating behavior was observed suggesting that animals treated with P21 or P22 did not present any sign of depression or locomotor impairment. The only general behavioral characteristic P21 and P22 altered was the level of anxiety of the mice. As shown in FIG. 16(b), mice treated with P21 or P22 spent more time in the center of the open field than control animals ($p<0.010$, Student's t-test) suggesting lower levels of anxiety.

To examine short-term memory, a one-trial object recognition task was conducted. Mice treated with P21 clearly spent more time exploring the new object than the familiar object whereas other groups did not, as seen in FIG. 16(e). The percentage of discrimination for animals treated with P21 was significantly increased compared to other groups, as seen in FIG. 16(f) ($p<0.05$, Student's t-test).

To investigate potential effects of P21 and P22 on hippocampal dependent memory, a spatial reference memory task in the water maze was conducted. Animals from all groups learned well, as evident by significantly declining escape latencies across training sessions, as see in FIG. 16(g) ($p<0.05$, two-way ANOVAs). However, performance of mice treated with P21 or P22 improved significantly faster than placebotreated animals. Escape latencies to reach the submerged platform were significantly reduced for groups treated with P21 or P22 compared to control group from training day 2 to 4 ($p<0.01$, two-way ANOVA and post hoc Fisher LSD test).

To evaluate the accuracy and the strength of the platform coordinates encoding, probe trials and measured the time animals spent looking for the platform in the target quadrant were performed. First a probe trial 24 hours after the last day of training was carried out. Then, to evaluate remote memory, probe trials 15 and 30 days after the training and the end of the chronic treatment were performed. Analysis of retention of memory in the three probe trials confirmed that all animals had correctly encoded the platform location during training since they spent more than 25% of the trial period looking for it in the target quadrant, as seen in FIG. 16(h). During the first probe trial, animals treated with P21 focus significantly more on the target quadrant compared to control animals ($p<0.05$, Student's t-test). However, this beneficial effect disappeared on day 15 and day 30 washout periods after the end of the treatment with the peptide. No statistically significant effect of P22 was observed in the probe trials.

Overall, results from the object recognition task and the spatial reference memory task show that P21 induced positive effects on cognition.

Because neurogenesis is thought to have an important role in memory and associated learning, potential changes induced by chronic treatment with P21 and P22 were investigated.

Quantitative evaluation of neurogenesis in the DG revealed a significant increase of BrdU positive cells in the GCL and SGZ of animals treated with P21, as seen in FIGS. 17(a) and 17(b) ($p<0.05$, two-way ANOVA and post hoc Fisher LSD test). No significant alteration in neurogenesis was observed in the group treated with P22, as seen in FIGS. 17(a) and 17(b).

To estimate net neurogenesis, the expression of the marker for mature neurons, NeuN, in the BrdU positive cells in the DG was examined next. A significant increase of the number of BrdU/NeuN positive cells was observed in the DG of mice treated with P21 due to a significant increased BrdU/NeuN positive cells in the GCL, as seen in FIGS. 17(a) and 17(c) ($p<0.05$, two-way ANOVA and post hoc Fisher LSD test). No significant changes were observed in the group of animals treated with P22.

Synapses are critical components of the neural mechanisms underlying learning and memory. In order to investigate whether P21 and P22 have neurotrophic effects, the expression of two synaptic vesicle proteins, synaptophysin and synapsin I, was measured.

Significant increases of synaptophysin and synapsin I immunoreactivities were observed in the GCL and molecular cell layer (MCL) of animals treated with P21, as seen in FIGS. 18(a) and 18(b) ($p<0.001$, two-ways ANOVAs and post hoc Fisher LSD test). Animals treated with P22 expressed similar levels of immunoreactivity of synaptophysin and synapsin I as did untreated control animals.

To investigate whether P21 affects LIF signaling pathway, HepG2 cells were treated with different concentrations of P21 from 0.01 to 1000 nM along with 0.25 nM LIF for 15 min, and then measured STAT3 phosphorylation by Western blots. It could be observed that LIF-induced STAT3 phosphorylation was inhibited slightly in a dose-dependent manner. In HepG2 cells, 10 nM of P21 inhibited ~30% of LIF induced phosphorylation of STAT3, as seen in FIG. 19 ($p<0.005$, Student's t-test).

Neurotrophic factors are critical for neuronal differentiation, maturation, and survival, but in the AD brain, the balance of neurotrophic factors is disturbed. Levels of basic fibroblast growth factor are upregulated, whereas the levels of brain-derived neurotrophic factor and neurotrophin 4 are reduced in the hippocampus, the frontal cortex and the parietal cortex. Because they are crucial to maintain a healthy neuronal microenvironment, neurotrophins generated excitement over the past decades as therapeutic targets for AD and other dementias. However, inconvenient pharmacokinetics and adverse side-effect profiles have limited clinical utilization of neurotrophic factors. Therefore, chemically modified short peptides able to mimic positive characteristics of neurotrophic factors represent an opportunity to circumvent these obstacles.

Derivatives of the diamondoid $C_{10}H_{16}$ hydrocarbon adamantane have already been commercialized as antivirals (amantadine, rimantadine) and as central nervous system active drugs. Nowadays, the aminoadamantane MEMANTINE® is the only drug prescribed for moderate to severe cases of AD. Based on the physicochemical and pharmacological properties of drugs incorporating the adamantane motif, an adamantane-based moiety has been used as a drug carrier for poorly absorbed compounds, including peptides, active towards the central nervous system. The foregoing examples demonstrated the beneficial effect of a CNTF based tetrapeptide, Peptide 6c, on hippocampus-dependent memory in normal adult mice. The addition of lipophilic groups to peptide 6c could increase its biostability and blood-brain-barrier permeability and consequently enhance its neurotrophic, neuroplastic, and cognitive enhancement activities. The rigid, bulky, and highly lipophilic, unnatural 3-aminoadamantane-1-carboxylic acid ("$^4$Gly") was attached C-terminally to peptide 6c to produce compound P21. The rigidity of the γ-amino acid AGly should block the carboxypeptidase activity, thereby stabilizing peptide 6c in vivo. Enhancing the overall lipophilicity of peptide 6c should boost its ability to cross the BBB. Capping the N-terminus of the sequence of peptide 6c with adamantane-1-carboxylic acid in P22, would further increase lipophilicity and BBB penetration as well as resistance against aminopeptidase activity.

In AD, the hippocampus is the most vulnerable brain region to neurodegeneration. Moreover, hippocampus-dependent cognitive impairments are associated with synaptic loss which occurs early in the development of AD. Reduction of synaptophysin in the hippocampus correlates with cognitive decline in AD patients and with decreased synaptic activity in several mouse models of AD. Therefore, in the present example the effects of compounds P21 and P22 on hippocampus-dependent cognitive functions and on hippocampal synaptic plasticity were investigated.

In the present study, P21 significantly enhanced two different cognitive mechanisms; an object recognition task and a spatial reference memory task. The one-trial object recognition task is thought to critically depend on the entorhinal cortex, hippocampus and frontal cortex. In the present example it was observed that control animals as well as animals treated with P22 did not preferentially explore the novel object. This null preference did not reflect a lack of interest for novelty but rather enhanced attraction for familiarity. This reveals that, for control and P22-treated animals, familiar object representation is yet to be built and finalized, therefore requiring as much attention as the novel object to complete the encoding. On the contrary, animals treated with P21 displayed a marked preference for the novel object. This suggests that the representation of the familiar object has been fully encoded, and then was not anymore a subject of attention at the expense of the novel stimulus. These results showed that P21 treatment accelerates the encoding of object representation, thus, in the present experimental condition, improved short-term memory performance.

In the spatial reference memory task, the hippocampal system processes information about the relationships among distal environmental cues into a spatial map where spatial coordinates of the submerged platform are encoded. The hippocampus is also crucial for memory storage, consolidation and restitution of the spatial information. In the present example, it was observed that both P21 and P22 increased the learning of the task suggesting that both peptides strengthen processing of the spatial environment. However, only P21 positively enhanced performances in the probe trial. This shows that the beneficial effect of P21 on encoding, storage, and consolidation of the spatial information during the treatment period is stronger than of P22.

Examining hippocampal synaptic activity, it was found that P21 induced significant increase in synaptophysin and synapsin I immunoreactivity in the DG. Synaptophysin is a glycoprotein of the presynaptic vesicles involved in the vesicle trafficking machinery by regulating synaptic vesicle exocytosis. Besides, synapsin I is a neuro-specific phosphoprotein highly concentrated in presynaptic nerve terminals, where, associated with the cytoplasmic surface of the synaptic vesicle, it plays a key role in neurotransmitter release. It was observed that P21 positively enhanced synaptophysin and synapsin levels. This suggests that P21 had a beneficial effect on synaptic plasticity by increasing the presynaptic release of neurotransmitters. This augmentation of neurotransmitters in the synaptic cleft may potentiate post-synaptic excitability, subsequently enhancing the efficacy of the neuronal network taking charge of stimulus processing to encode, store or recall information.

The contribution of adult hippocampal neurogenesis to memory has been studied at experimental and theoretical levels. Current literature supports the idea that both neural stem cells and immature neurons play distinct roles in hippocampus dependent memory tasks. Newly born mature cells may have an inherent advantage of being recruited into patterns of new memory networks. In the present example, it was observed that P21 increased progenitor cell proliferation as well as neuronal differentiation. Thus, through this neurogenic activity, P21 enhanced the stock of functional neurons to be potentially recruited into neuronal networks of information processing. This characteristic of P21 might be crucial as a potential treatment for neurodegeneration since in AD, although proliferation of immature neurons is increased, newly generated neurons in the DG do not mature.

The present example shows that P21 induces neuronal plasticity and neurogenic properties which consequently enhance cognition. In particular, the effects of P21 in the hippocampus were investigated, but, considering positive enhancement of the object recognition task which involves other brain structures as well as the hippocampus, it is speculated that the beneficial effect of P21 shown to be connected with neuronal plasticity in the DG may occur in other brain areas as well.

In the aforementioned examples it could be shown that peptide 6 contains a putative leukemia inhibitory factor receptor (LIFR)-binding sequence of CNTF and interferes with the signal transduction of LIF more than with that of CNTF. Because LIF inhibits neurogenesis in the DG, it was hypothesized that peptide 6 enhances neurogenesis through the CNTF pathway, inducing a partial inhibition of LIF. The present example shows that P21 acts as its parent molecule, the 11-mer peptide, partially inhibiting LIF activity through the STAT3 pathway. Because no conclusive effects of the closely related derivative P22 were observed, which differs in the N-terminal acylation, on cognition, neuronal plasticity and neurogenesis, it is assumed that incorporating an additional adamantane moiety instead of the smaller N-acetyl group at the N-terminus of P21 to furnish P22, probably prevented a proper interaction of the active-DGGL-subsequence with its receptors.

Overall, in the present example it could be shown that the CNTF-derived peptidergic compound, P21, incorporating a γ-aminoadamantane-1-carboxylic acid at its C-terminus, is neurogenic and neuroplastic and enhances cognition in normal adult mice. It is important to note that demonstrating positive effects of the studied peptides is a challenging task because it is difficult to observe enhancement of cognition due to ceiling effects in normal adult mice which were used previously. The lipophillically modified, CNTF-derived pentamer P21 is an attractive candidate for the development of pro-cognitive drugs to prevent and treat learning and memory disorders and neurodegenerative diseases such as AD.

Example 5

In this Example, the chronic treatment with Peptide 21 is shown to restore neuronal and synaptic plasticity, associated cognitive impairments, and the underlying tau pathology in the later stage of the AD-like pathology. The 3xTgAD female mice and wild type (WT) controls were treated with Peptide 021 or vehicle diet (n=14-16/group) starting at 9-10 months of age. Treatment continued for a total period of 12 months. Animals were behaviorally tested after 6 months of treatment (15-16 months of age). After completion of the behavioral task, half of the animals (n=7-8/group) were perfused and brains were collected for immunohistochemical and biochemical analysis. Remaining animals were continued on Peptide 021/vehicle diet for another 6 months, and were sacrificed at 21-22 months of age for immunohistochemical and biochemical analysis (FIG. 20B).

Since administration of the full-length CNTF protein in human clinical trials is known to cause anorexia, skeletal muscle loss, hyperalgesia, severe cramps, and muscle pain, the general physical state of animals was carefully checked throughout the period of the study. During the entire 12 months of treatment, there were no observed alterations in general physical state, including grooming, posture, and clasping reflex, due to either the genotype or treatment with Peptide 021. The body temperature, body weight, and food consumption were evaluated monthly for the first 6 months of the study till the behavioral evaluation was performed. FIG. 21A represents body temperature follow up. Statistical analyses revealed a significant difference among groups (ANOVA, p=0.005). Post-hoc analysis showed a significant difference between WT animals treated with vehicle compared to other groups (Fischer's post-hoc test, p=0.022). As shown in FIG. 21B, statistical analysis on the body weight also showed significant difference among groups (ANOVA, p<0.001). Post-hoc analysis showed that WT animals treated with Peptide 021 were significantly heavier than the three other groups (Fisher's post-hoc test, p<0.025). WT mice, irrespective of the treatment, remained heavier than 3xTg-AD mice (Fisher's post-hoc test, p<0.05). The treatment with Peptide 21 did not induce any significant change of weight in 3xTgAD mice (Fisher's post-hoc test, p=0.233). FIG. 21C represents food consumption over the 6 months of treatment. Statistical analysis did not show any difference among groups (ANOVA, p=0.198).

FIG. 21D represents the animals' performance in the elevated plus-maze task. No effect of genotype or treatment was noted on the level of anxiety as the statistical analysis did not reveal any significant difference between groups in the amount of time spent in OA (ANOVA, p=0.7805). Previously, it was reported that 8-9 months old 3xTgAD mice displayed levels of anxiety which were marginally higher than the wild type controls. However, in the current study, the older 3xTgAD mice (15-16 months old) did not show such trends.

Locomotivity and motor coordination were evaluated in the accelerating Rotarod. 3xTgAD mice displayed higher scores than WT control mice (FIG. 21E; ANOVA; group effect: p<0.0001, Student's t-test, p<0.001). These results are surprising since it was shown that the P301L mutation affects the brain stem and consequently induces locomotor impairment. However, consistent with the present study, other studies have reported that at 5-7 months of age JNLP3 mice (harboring the P301L mutation) and AbetaPP+tau mice (harboring P301L mutation and hAPP Swedish K670N and M671L mutations) displayed higher scores than WT animals in both the Rotarod and the balance beam task. Also, in a previous study with 8-9 months old 3xTgAD mice, similar trends were found in the Rotarod performance. Except for this difference of performance due to the genotype, there was not observed any difference due to the treatment with Peptide 21 (WT-Vehicle versus WT-Peptide 21, Fischer's post-hoc test, p=0.7903; 3xTgAD-Vehicle versus 3xTgAD-Peptide 021, Fischer's post-hoc test, p=0.9231).

Exploratory activity was evaluated analyzing pattern and level of 15-minute free exploration of an animal in an arena. For rodents, the center of the arena is more anxiogenic than the periphery. Thus, measuring the time spent in the center of the arena, allows evaluating the potential effect of anxiety on exploratory behavior. As represented in FIG. 2F, the pattern of exploration of all groups was similar as all groups spent same time visiting the center of the arena (ANOVA, p>0.798). These data reaffirmed the similar anxiety levels detected among groups in the elevated plus-maze (see above).

To examine if animals displayed similar level of exploratory activity in a new environment, the total distance covered in the arena was analyzed in five intervals of 3 min each. All animals displayed similar level of exploration and covered comparable distance in the open field (FIG. 21G; ANOVA, p=0.712). These results suggested that neither the genotype nor the treatment with Peptide 21 altered general motivation for exploration of a new environment.

It is widely reported that in AD patients, during initial phases of the disease, the clinical symptoms include memory loss, particularly of recent events. In 3xTg-AD mice, the onset of cognitive impairment is known to occur around 5 months of age, in advance of overt plaque and tangle pathologies, and consists of hippocampus dependent impairment of spatial memory retention. To test whether treatment with Peptide 21 can alleviate early cognitive deficits in 3xTg-AD mice, a test for short-term memory and a hippocampal-dependent spatial reference memory was performed.

In the one-trial object recognition task, animals were exposed to two different objects which they have to identify as novel or familiar based on the memory of an earlier experience with one of the two objects they encountered in the same open-field. The familiar object is explored a shorter time than the novel object because the representation of the former is still available in memory. The one-trial object recognition task tests some aspects of episodic memory but is limited to memory of an object (what), the location of an object (where), and the context in which it was encountered (which). However, the temporal dimension of the episode remains inaccessible to the experimenter, and because of this reason this task in animals is considered a test of short term memory. The one-trial object recognition task is thought to critically depend on the entorhinal cortex, hippocampus and frontal cortex.

During the sample phase, all animals similarly explored both objects (FIG. 22A, ANOVA, p>0.999). During the test phase, 3xTg-AD mice displayed a significantly lower discrimination score than other groups (Student's t-test, p<0.003) (FIG. 22B). This result means that 3xTg-AD mice treated with vehicle did not preferentially explore the novel object. This null preference did not reflect a lack of interest for novelty but rather enhanced attraction for familiarity. This revealed that familiar-object representation was yet to be built and finalized, therefore requiring as much attention as the novel object to complete the encoding. In contrast, WT control mice and 3xTg-AD mice treated with Peptide 021 displayed a clear preference for the novel object. This suggested that the representation of the familiar object started to be encoded, and then was less a subject of attention at the expense of the novel stimulus. These results showed that Peptide 021 can rescue short-term memory of 15-16 months old 3xTg-AD mice.

The spatial reference memory task assesses hippocampus dependent reference memory in rodents, requiring that mice use a spatial navigational strategy to find a fixed submerged escape platform. The hippocampal system processes information about the relationships among distal environmental cues into a spatial map where spatial coordinates of the submerged platform are encoded. The hippocampus is also crucial for memory storage, consolidation, and restitution of the spatial information.

Because general behavioral evaluation demonstrated higher level of locomotivity for 3xTgAD mice compared to WT control animals (Rotarod test), the first parameter considered in the water-maze training was the swim speed of animals. It is indeed crucial to first elucidate if locomotivity was comparable between 3xTgAD and WT mice otherwise interpretation of data for learning and memory evaluation can be misinterpreted.

As shown in FIG. 22C, all animals displayed similar swim speed (ANOVA, p<0.070). The performance of the animals was analyzed as latency to reach the submerged platform. As depicted in FIG. 22D, there is a significant difference of learning among groups (ANOVA, p=0.010). Post-hoc analysis showed that 3xTgAD mice needed significantly longer latencies to reach the platform than WT control animals and 3xTg-AD mice treated with Peptide 021 (Fisher's test, p<0.006). These results showed that treatment with Peptide 21 can alleviate impairment of spatial learning of 16 month-old 3xTgAD mice.

The probe trial allows evaluating the strength of the encoding of the spatial information. The more an animal searches for the platform in the target quadrant, the more the information of the spatial coordinates of the submerged platform was strongly encoded. As depicted in FIG. 22E, 3xTg-AD mice treated with vehicle spent significantly less time in the target quadrant than WT mice treated with vehicle (Student's t-test, p=0.032). However, 3xTg-AD treated with Peptide 21 displayed similar performance as WT controls. These results showed that at 15-16 months, the delay 3xTgAD mice displayed to learn spatial information is associated with a less robust encoding than controls after a similar training regimen, and that treatment with Peptide 21 can successfully rescue this impairment.

Synaptic loss, as reflected by changes in the presynaptic marker synaptophysin, correlates better with cognitive decline than either Aβ plaque load or neurofibrillary tangles in AD cases. 3xTgAD mice are known to develop deficits in synaptic plasticity by 6 months of age, including impairments in LTP and paired-pulse facilitation. Applicant had shown before that Peptide 6 can rescue deficits in neuronal plasticity in 3xTgAD mice. In the present example, chronic treatment with Peptide 021 was analyzed to determine whether it can reverse deficits in synaptic plasticity in these mice.

Synaptophysin is a glycoprotein of pre-synaptic vesicles involved in the vesicle trafficking machinery by regulating synaptic vesicle exocytosis. A significant decrease of synaptophysin immunoreactivity in 3xTgAD mice treated with vehicle compared to WT controls in the CA1 (ANOVA, p<0.001, Bonferroni's post-hoc test, p<0.001), in the CA3 (ANOVA, p<0.001, Bonferroni's post-hoc test, p<0.001), and in the dentate gyrus ((ANOVA, p<0.001, Bonferroni's post-hoc test, p<0.001) (FIG. 23A) was observed. Peptide 21 treatment was able to rescue the deficit in these hippocampal regions in the 3xTgAD mice (Bonferroni's post-hoc test, p<0.001, p<0.01, and p<0.05 for CA1, CA3, and DG regions respectively) (FIG. 23A).

Synaptic pruning is a feature of AD pathology. The expression of AMPA receptor subunits was evaluated due to their essential role for synaptic transmission and LTP as well as cellular mechanisms which are connected with learning and memory. Peptide 21 was able to induce a significant increase of the GluR1 subunit of AMPA receptors in the dentate gyrus region of the hippocampi of 3xTgAD mice which showed deficit as compared to WT. (WT-Vh versus Tg-Vh, Student's t-test, p=0.035; Tg-Vh versus Tg-P021, Student's t-test, p=0.048) (FIG. 23B).

Biochemical analysis was used pre- and post synaptic structures to further evaluate the effect of Peptide 021 on synaptic plasticity (FIG. 23C). Western blots developed with anti-synapsin I showed a marginally significant increase in WT animals (WT-Vh versus WT-P021, Student's t-test, p=0.054), however, the difference between Tg-Vh and Tg-P021 did not reach statistical significance (Student's t-test, p=0.1419). Similar trends were observed with the post-synaptic marker, PSD95 (WT-Vh versus WT-P021, Student's t-test, p=0.012, Tg-Vh versus Tg-P021, Student's t-test, p=1.000).

Altogether these results suggest that chronic treatment with Peptide 21 can rescue deficits in expression of synaptic plasticity markers in 3xTgAD mice. The increase in synaptic plasticity can be the underlying mechanism by which the peptide ameliorated the cognitive deficits in these mice.

In AD patients, Aβ and tau pathologies are associated with unsuccessful neurogenesis and loss of neuronal plasticity. It was observed that shifting the balance from neurodegeneration to regeneration of the brain by CNTF derived Peptide 21 rescued deficits in synaptic plasticity and cognition. So, the next important step was to evaluate the effect of the peptide on these pathologies. In 3xTg AD mice, the tau pathology occurs at late age and is first visible in the CA1 pyramidal neurons, becoming readily apparent in the hippocampus and in cortical structures by 12-15 months of age. To finally investigate whether Peptide 21 had any effect on the development of tau pathology, immunohistochemical studies were conducted in 15-16 months old (6 months treatment) animals (FIG. 24A) and biochemical studies in 21-22 months old animals (12 months treatment) (FIG. 24B).

Immunohistochemistry with AT8 (anti-pSer202/pThr205 tau) antibody revealed specific immunoreactivity in the subiculum and in the CA1 region of the hippocampus of 15-16 months old (6 months treatment) animals (FIG. 24A). A significant reduction in Peptide 021 treated 3xTgAD animals was seen as compared to the vehicle treated group (Subiculum, Student's t-test, p=0.0014 and CA1, Student's t-test, p<0.0001). Hyperphosphorylated microtubule-associated protein tau is the major component of the paired helical filament of Alzheimer's disease, and its reduction by chronic treatment with Peptide 21 shows that peptide has a neurprotective effect against tauopathy in the animal model of the disease.

As expected, the Western blots from hippocampi of 21-22 months old animals (12 months treatment) developed with the human specific tau antibody 43D showed human tau expression only in 3xTg-AD, but not the control mice; no significant effect of the peptide was noted. The Western blots developed with phosphorylation independent tau antibody, R134d did not reveal any significant difference between groups; however, there was a trend towards increased expression in 3xTgAD mice. Western blots with 77G7 antibody (reactive to all six isoforms of tau) did not show any significant difference between groups (ANOVA, p=0.113). The Western blots developed with pan-tau antibody, 92e, also did not show any significant difference between groups (ANOVA, p=0.0755).

A significant increase in PHF-1 (pSerine 396/pSerine 404) was observed in vehicle treated 3xTgAD mice as compared to WT (Student's t-test, p=0.0345). Chronic treatment with Peptide 21 significantly reduced the abnormal hyperphosphorylation at this site (Student's t-test, p=0.0382). Similarly, Western blots developed against pSerine-262/pSerine-368 antibody, 12E8, showed significant increase in vehicle treated 3xTgAD mice compared to WT controls (Student's t-test, p=0.0084). Peptide 21 treatment significantly reduced the expression in 3xTgAD mice (Student's t-test, p=0.0306).

A significant increase in the abnormal hyperphosphorylation of tau pSerine 199 (Student's t-test, p=0.024) but no effect of Peptide 21 was observed (Student's t-test, p=0.3170). A significant increase in AT8 (pSerine 202/pThreonine 205) was observed in vehicle treated 3xTgAD mice as compared to WT (Student's t-test, p=0.0078). Chronic treatment with Peptide 21 did not affect the abnormal hyperphosphorylation at this site (Student's t-test, p=0.948). This was different from the significant reduction noted in the expression of AT8 in 3xTgAD mice treated with Peptide 21 by using immunohistochemical quantification in 6 month treated animals. However, this could be explained partially by the fact that AT8 expression was noted only in the CA1 and subiculum regions of the hippocampus, and immunohistochemistry is known to be more precise for detecting region specific changes than Western blotting.

Taken together, these results show that chronic treatment with Peptide 21 significantly reduced abnormal hyperphosphorylation of tau both in 15-16 months and 21-22 months old animals.

FIG. 20A shows the structure and design of the peptidergic compound used in the study. Peptide 21 (Ac-DGGL$^4$G-NH$_2$) which corresponds to amino acid residues 148-151 of human CNTF (FIG. 20A) was identified as an active region of this neurotrophic factor by epitope mapping of neutralizing antibodies to CNTF. The peptide was synthesized and purified by reverse phase HPLC to >96% purity, as described previously.

The 3xTg-AD homozygous mice harboring PS1M146V, APPSwe, and tauP301L transgenes were obtained from Frank LaFerla through Jackson Laboratory (New Harbor, Me., USA). The background of the 3xTg-AD mice is a hybrid 129/Sv 9 C57BL/6. NonTg wild type (WT) mice used were from the same strain and genetic background and were obtained from Jackson Laboratory. Mice were housed and bred in accordance with approved protocols from our Institutional Animal Care and Use Committee, according to the PHS Policy on Human Care and Use of Laboratory animals (revised March, 2011). This study was performed on homozygous 3xTg-AD female mice. Mice were group-housed (4 animals per cage) with a 12:12 h light/dark cycle and with ad libitum access to food and water.

3xTg-AD mice (9-10 months old) (n=15-16) and WT controls (n=15-16) were treated orally with Peptide 021 or vehicle diet for 12 months. Treatment was administered as 60 nmolpeptide/g formulated diet (Research Diets; New Brunswick, N.J.). The vehicle-treated control animals received the same diet but without the peptide. Animals were behaviorally tested after 6 months of treatment (15-16 months of age). First general behavioral battery of tests was done, and then cognitive tests were carried out. After completion of the behavioral task, half of the animals (n=7-8/group) were perfused and brain tissue was collected for immunohistochemical and biochemical analysis. Remaining animals were continued on Peptide 021/vehicle diet for another 6 months, and were sacrificed at 21-22 months of age for immunohistochemical and biochemical analysis (FIG. 20B).

The physical state and condition of the animals were carefully checked throughout the treatment by evaluating grooming, posture, physical state, and clasping reflex. Bodyweight, body temperature, and food consumption during the first 6 months were also recorded.

As a test which has traditionally been used to evaluate anxiety/emotionality, the elevated plus-maze consisted of four arms (30×5 cm) connected by a common 5×5 cm center area. All arms and the central area were constructed with dark opaque Plexiglas. Two opposite facing arms were open (OA), whereas the other two facing arms were enclosed by walls (CA, 20 cm height). The entire plus-maze was elevated on a pedestal to a height of 82 cm above floor level. Ambient luminosity was maintained at 60 Lux to control the anxiogenic feature of light for rodents. During a single 8-min session, an animal was placed onto the central area. A videotracking system detected the presence of the animal and the time it spent in the different zones of maze-arms. Between each session, any feces were cleared from the maze, and the maze floor was cleaned with 70% alcohol to remove any urine or scent cues. For each animal, the number of CA entries, OA entries, and amount of time spent in CA and OA were recorded. As OA are more anxiogenic for rodents than CA, the percentage of time spent in OA was calculated to evaluate anxiety-like behavior of animals. The percentage of time spent in OA corresponds to the ratio of the time spent in OA compared to the time spent in all arms (OA+CA).

Testing on accelerating Rotarod was conducted by giving each mouse two sessions of three trials each with the motor in accelerating mode (factory settings). In this mode, the rotating speed increased steadily, at a rate of 0.02 cm/s, from 4 to 40 rpm. The latency to fall off the Rotarod was calculated. Inter-trial intervals were 10-15 min for each mouse.

Exploratory activity was evaluated analyzing pattern and level of 15-minute free exploration of an animal in an arena. The testing apparatus was a classic open field (i.e. a PVC square arena (50×50 cm), with walls 40 cm high). The open field was placed in a part of the room separated from the experimentor with a black opaque curtain. The open field was surmounted by a video camera connected to a computer tracking animals. Data collection was performed using a video tracking system (Smart version 2.0.14 software, Pan Lab/San Diego Instruments). The data was analyzed time spent in the center of the arena (measure of anxiety) and distance covered (measure of exploratory activity) during the single 15-minute testing session.

The test used was an adaptation of the procedure previously described by Sargolini and collaborators. The testing apparatus was a classic open field (i.e. a PVC square arena, 50×50 cm, with walls 40 cm high). The open field was placed in a part of the room separated from the investigator with a black opaque curtain. The open field was surmounted by a video camera connected to a computer. Three objects were employed in this task. The general procedure consisted of three different phases: a familiarization phase (4 sessions of 10 min each on 4 consecutive days), a sample phase (5$^{th}$ day), and a test phase (5$^{th}$ day). On the first four days, mice were individually submitted to the familiarization session during which they were introduced in the empty arena in order to become familiar with the apparatus. On the fifth day, each mouse was first submitted to the sample phase (session 1, ten minutes) for which two identical objects were placed in a symmetric position from the centre of the arena. After a 15 minute delay during which the mouse returned to its home cage, it was reintroduced in the arena to perform the test phase (session 2, 10 min). The mouse was then exposed to two objects: a familiar object (previously presented during the sample phase) and a new object, placed at the same location as during the sample phase. Data collection was performed using a video tracking system (Smart version 2.0.14 software, Pan Lab/San Diego Instruments). Object discrimination was calculated as follows:

OD=(time spent close to new object)/(time spent close to new object+time spent close to old object)× 100

The test used was an adaptation of the procedure previously described by Morris et al (20). The procedure was performed in a 180-cm diameter circular tank. The pool was filled with water (21±1° C.) made opaque by adding white non-toxic paint. Acquisition started with the escape platform (13 cm diameter submerged 1 cm below water surface) in the Northwest quadrant, and each animal was given 90 s to find the platform. If the mouse did not find the platform in 90 s, it was gently guided to it. At the end of each trial, the mouse was left on the platform for 20 s, then dried, and returned to its home cage until the next trial. Three such acquisition trials were given on each day for four consecutive days. Each animal performed a total of 12 trials corresponding to a partial training of the spatial reference memory task. The measures of learning were the time and distance covered to reach the escape platform. For the probe trial, the tank was divided into four imaginary quadrants and a small zone where the escape platform had been. The measures of retention were the percent of time spent and the percent of distance covered in each quadrant. Swim speed was also calculated. Mice behavior in the water-maze was monitored by a Samsung Digital Camera (SDC 4304) mounted to the ceiling and tracked and timed using a SMART (PanLab/San Diego Instruments) version 2.0.14 software.

After completion of the behavioral task at six months treatment (15-16 months old animals), half of the animals (n=7-8/group) were perfused and brain tissue was collected for immunohistochemical and biochemical analysis. Remaining animals were continued on Peptide 021/vehicle diet for another 6 months, and were sacrificed at 21-22 months of age for immunohistochemical and biochemical analysis.

Animals were anesthetized with an overdose of sodium pentobarbital (125 mg/kg) and transcardially perfused with 0.1 M phosphate buffered saline (PBS). After perfusion, the brains were removed from the skull; the left hemisphere was dissected into hippocampus and cortex and then immediately frozen in dry ice for biochemical analysis, and the right hemisphere was fixed in 4% paraformaldehyde in 0.1 M PBS for at least 24 h at room temperature. Tissues were then post-fixed in a 30% sucrose solution at 4° C. overnight. 40-μm sagittal sections of the entire hippocampus were cut on a freezing microtome. The sections were stored in glycol anti-freeze solution (Ethylene glycol, glycerol and 0.1 M PBS in 3:3:4 ratio) at −20° C. until further processing.

Immunohistochemistry was performed on free-floating sections and every tenth brain section was chosen for densitometry and quantification. For immunohistochemical quantification, brain sections of 5-6 animals per group were randomly selected and analyzed. The primary antibodies against the following proteins were used at the indicated dilution: rabbit polyclonal anti-synapsin I (1:2,000; Stressgen, Victoria, BC, Canada), mouse monoclonal anti-synaptophysin (1:200; Millipore, Temecula, Calif., USA), rabbit polyclonal anti-GluR1 (1:300; Millipore, Temecula, Calif., USA), and anti-pSer202/pThr205, AT8 (1:500; ThermoScientific, Rockford, Ill., USA). The following secondary antibodies were used: Alexa 488-conjugated goat antimouse IgG antibody (1:500, Molecular Probes, Carlsbad, Calif., USA) and Alexa 594-conjugated goat anti-rabbit IgG antibody (1:500, Molecular Probes, Carlsbad, Calif., USA).

For densitometry, the region of interest was outlined on every tenth section. For synaptophysin, the entire area of the GCL, the CA1, and the CA3 of the hippocampus and parietal association and frontal cortices were analyzed. For immunohistochemistry with antibody to tau, only brain regions showing positive specific staining were quantified, namely the CA1 of the hippocampus and the subiculum. Maximum projection images were then generated based on confocal z-stacks using Nikon 90i fluorescent microscope equipped with Nikon C1 three-laser confocal system and a Nikon DS U1 digital camera. The antibody staining was quantified by measuring mean pixel intensity (MPI) with the software Image-ProPlus 5.0 (Media Cybernetics, Silver Spring, Md., USA).

Brain tissue stored at −80° C. from each PBS perfused mouse was homogenized in a Teflon-glass homogenizer to generate 10% (w/v) homogenate. The homogenization buffer contained 50 mM Tris-HCl, pH 7.4, 0.25 M sucrose, 2 mM EDTA, 10 mM b-mercaptoethanol plus the following protease and phosphatase inhibitors: 0.5 mM AEBSF, 8 lg/ml aprotinin, 10 lg/ml leupeptin, 4 lg/ml pepstatin, 5 mM benzamidine, 20 mM b-glycerophosphate, 50 mM sodium fluoride, and 1 mM sodium vanadate. Protein concentration of each brain homogenate was determined by modified Lowry assay. The tissue homogenates were boiled in Laemmli's buffer for 5 min, and then subjected to 10% SDS-polyacrylamide gel electrophoresis, followed by transfer of separated proteins on 0.45 μm immobilon for Western blots. The Western blots were developed with antibodies to synaptic markers, tau, phosphor-tau. For loading control, the blots were developed with mAb to GAPDH (1 lg/ml; Abcam, Cambridge, Mass., USA). Immunoreactive protein bands were visualized with enhanced chemiluminescence (ECL) reagents (Pierce, Rockford, Ill., USA). The ECL films of the blots were scanned and analyzed using Multi Gauge software version 3.0 (Fujifilm, Tokyo, Japan). Mean values for each group of animals were analyzed by t test. Differences with p<0.05 were considered significant.

The statistical analyses were conducted using SPSS version 17.0 (© SPSS Inc., 1989-2007, Chicago, Ill., USA), StatView, SASv5 software (SAS Institute, Cary, N. C., USA), and GraphPad Prism version 5.0 (GraphPad software inc., La Jolla, Calif., USA). Data are presented as mean±S.E.M. For analysis involving multiple groups, one-way ANOVA with post hoc Fisher's/Tukey's/Newman-Keul's/Bonferroni's test (as indicated) was used. For all other comparisons (including inter-group comparisons), Student's t-test was used. For all purposes, p<0.05 was considered as statistically significant.

Example 6

The adeno-associated virus vector-induced expression of the N-terminal $I_{2NTF}$ and C-terminal $I_{2CTF}$ halves of $I_2^{PP2A}$, also called SET, in brain reproduced key features of AD in Wistar rats. The $I_{2NTF-CTF}$ rats showed a decrease in brain PP2A activity, abnormal hyperphosphorylation and aggregation of tau, a loss of neuronal plasticity and impairment in spatial reference and working memories. To test whether early pharmacologic intervention with a neurotrophic molecule could rescue neurodegeneration and behavioral deficits, 2.5-month-old $I_{2NTF-CTF}$ rats and control littermates were treated for 40 days with Peptide 6, an 11-mer peptide corresponding to an active region of the ciliary neurotrophic factor. Peripheral administration of Peptide 6 rescued neurodegeneration and cognitive deficit in $I_{2NTF-CTF}$ animals by increasing dentate gyrus neurogenesis and mRNA level of brain derived neurotrophic factor. Moreover, Peptide 6-treated $I_{2NTF-CTF}$ rats showed a significant increase in dendritic and synaptic density as reflected by increased expression of synapsin I, synaptophysin and MAP2, especially in the pyramidal neurons of CA1 and CA3 of the hippocampus.

On the day of birth (p 0.5) male Wistar rat pups were anesthetized on ice, and 2 l 1 containing 4 9 109 AAV1 genomic equivalents of $I_{2NTF-CTF}$ or, as a control, AAV1-green fluorescent protein (GFP) were injected into each lateral ventricle of the brain with a 10-11 Hamilton syringe (Hamilton Syringe Company, Reno, Nev., USA). After 2.5 months, both groups of animals were treated for 40 days with Peptide 6 (intraperitoneal injection daily; 400 nmol/kg/day) or vehicle (NaCl, 0.9%). Peptide 6, which resembles the active region of human CNTF (residues 146-156), was synthesized by solid phase peptide synthesis (SPPS) method. After 18 days of the treatment for 3 consecutive days, rats were injected with BrdU (50 mg/kg/dose) to label dividing cells. At the end of the treatment, the effect of long-term overexpression of $I_{2NTF-CTF}$ as well as administration of Peptide 6 were tested on cognitive deficits, tau phosphorylation, Ab level, neurogenesis and neuronal plasticity. Abnormal hyperphosphorylation and aggregation of tau and Ab immunohistochemical staining were also studied 13 months post-AAV1-$I_{2NTF-CTF}$ transduction.

Previously generated pEGFP-N3/$I_2^{PP2A}$ was used as a template to generate by PCR $I_{2CTF}$ and $I_{2NTF}$ cDNA. The primers were: forward 50-gatggatccaaagccagcaggaaga-30 and reverse 50-gatctcgagttagtcatcttctc-30 for $I_{2CTF}$, forward 50-attactagtatgtcggcgccggcggcc-30 and reverse 50-tgcgatatc ttaattctgcgtttgactcgaacg-30 for $I_{2NTF}$. The plasmid was verified by DNA sequencing. The cDNA fragments were then cloned into the multicloning site of the AAV viral genome containing plasmid pTRUF12 and expression was driven by the CMV promoter/enhancer. Serotype 1 virus was generated and titers were calculated from standard curve generated from pTRUF as previously described.

Wistar rats were housed and bred according to the PHS Policy on Human Care and Use of Laboratory animals (revised Mar. 15, 2010). Rats were housed (2/3 animals per cage) with a 12:12-h light/dark cycle and with ad libitum access to food and water. Studies on animals were carried out according to approved protocols from our Institutional Animal Care and Use Committee.

For immunohistochemistry and biochemical analyses, animals were anesthetized with an overdose of sodium pentobarbital (125 mg/kg) and then killed by transcardial perfusion with 0.1 M phosphate buffered saline (PBS). The left hemisphere was dissected into hippocampus, cerebral cortex (parietal associated and motor cortex and hind limb region), and ventricular area and kept at −80° C. for biochemical analysis while the right half of the brain was immersion-fixed for 48 h in 4% paraformaldehyde in PBS, then cryoprotected in 30% sucrose for immunohistochemical investigations and 40 μm sagittal sections were cut using a freezing-sliding Microtome.

Total RNA was extracted from cerebral cortex, hippocampus and ventricular area with RNeasy plus mini kit (Qiagen, Valencia, Calif., USA) according to manufacturer's instructions. cDNA synthesis was achieved using Super script first strand kit (Invitrogen, Carlsbad, Calif., USA). rt-PCR amplification was performed in a thermocycler for 30 cycles (a cycle consisted of steps with denaturation for 30 s at 95° C., annealing for 30 s at 60° C., polymerization for 30 s at 72° C.). The primer sequence for $I_{2NTF}$ was the following: forward 50-gcaagaagcgattgaacaca-30 and reverse 50-gcagtgcctct-tcatcttcc-30. The amplification products were resolved on 2% agarose gels and quantified using the Molecular Imager system (Bio-Rad, Hercules, Calif., USA).

RT-qPCR was performed using Brilliant SYBR Green Master Mix (Agilent, Santa Clara, Calif., USA) in a Stratagene Mc3000p PCR detection system under the following conditions: 10 min at 95° C., 40 cycles of denaturation at 95° C. for 30 s, annealing 55° C. for 1 min, extension at 72° C. for 1 min. The primer sequences were the following: forward 50-gcgg cagataaaaagactgc-30 and reverse 50-gccagccaat-tctctttttg-30 for brain derived neurotrophic factor (BDNF); forward 50-tgttgctgccaagaaagatg-30 and reverse 50-acgtg-gctggactca atacc-30 for microtubule-associated protein 2 (MAP2); forward 50-tgtcagggaactggaagacc-30 and reverse 50-agttccac gatgagctgctt-30 for synapsin I; forward 50-aag-gtgacctccaag tgtgg-30 and reverse 50-acgatttctgctccatggtc-30 for tau; forward 50-gggaggtggaaggaaaagag-30 and reverse 50-ccttcttg gtcaccaccact-30 for neurofilament M; forward 50-cgccc tgtgagctgaactctg-30 and reverse 50-ctgcttctcagct-gcctgacc-30 for tropomyosin receptor kinase B (TrkB); forward 50-gacat gccgcctggagaaac-30 and reverse 50-agcccag-gatgccctttagt-30 for glyceraldehyde 3-phosphate dehydrogenase (GAPDH). Relative quantification was performed using the DDCt method.

Protein phosphatase-2A (PP2A) activity was assayed by ELISA in rat hippocampus homogenate (in the presence or absence of 15 nM okadaic acid). Sarkosyl-insoluble tau Sarkosyl-insoluble tau was isolated from the cerebral cortices of 13-month-old $I_{2NTF-CTF}$ and GFP control rats according to Greenberg and Davies. The sarkosylsoluble and the sarkosyl-insoluble fractions were dissolved in Laemmli sample buffer and employed for Western blots.

Rat hippocampus was homogenized to generate 10% (w/v) homogenate in cold buffer containing 50 mM Tris-HCl (pH 7.4), 8.5% sucrose, 2 mM EDTA, 2 mM EGTA, 10 mM b-mercaptoethanol, benzamidine 5 mM, 0.5 mM AEBSF, 4 lg/ml pepstatin A and 10 lg/ml each of aprotinin and leupeptin, 20 mM b-glycerolphosphate, 100 mM sodium fluoride, 1 mM sodium vanadate and 100 nM okadaic acid. After protein assay by modified Lowry method, Western blots were carried out and quantitated as described previously. The following primary antibodies were used: anti-GluR1 (1:1,000; Millipore, Temecula, Calif., USA), anti-GluR2/3 (1:5,000; Abcam, Cambridge, Mass., USA), anti-PSD95 (1:1,000; Cell Signaling Technology, Danvers, Mass., USA), anti-Egr-1 (1:400; Santa Cruz Biotechnology, Santa Cruz, Calif., USA), anti-GAPDH (1:1,000; Invitrogen, Carlsbad, Calif., USA), anti-PP2Ac (1:1,000; BD Transduction Laboratories, KY, USA), pan-tau antibody 92e (1:5,000; [16], tau pS199 (1:1, 000; Biosource, Camarillo, Calif., USA), tau pT205 (1:1,000; Biosource), tau pS214 (1:1,000; Biosource), tau pT217 (1:1, 000; Biosource), M4 to tau phosphorylated Thr231/Ser235 (1:500; [18], tau pS262 (1:1,000; Biosource), tau pS396 (1:1, 000; Biosource), pS422 (1:1,000; [57], and PHF1 [14].

Immunohistochemistry was performed on free-floating sections and every sixth brain section was chosen for densitometry and quantification. The primary antibodies against the following proteins were used at the indicated dilution: rabbit polyclonal anti-tau pS199, pT205, pS262, and pS396 (1:200; Biosource), anti-synapsin I (1:2,000; Stressgen, Victoria, BC, Canada), anti-synaptophysin (1:200; Millipore, Temecula, Calif., USA), anti-MAP2a,b (1:1,000; Sternberger Monoclonals, MD, USA), anti-BrdU (1:400; Accurate, Westbury, N.Y., USA), anti-NeuN (1:500; Chemicon, Temecula, Calif., USA), anti-$I_2^{PP2A}$ (anti-SET, 1 lg/ml; [66], rabbit polyclonal anti-Ab1-40 (5 lg/ml; Abcam, Cambridge, Mass., USA; 1:200; Invitrogen, Camarillo, Calif., USA), anti-N-methyl D-aspartate (NMDA) receptor 1 (1:200; ThermoScientific, Rockford, Ill., USA). Alexa 488-conjugated goat anti-mouse IgG antibody (1:500; Molecular Probes, Carlsbad, Calif., USA), Alexa 594-conjugated goat anti-rabbit IgG antibody (1:500; Molecular Probes, Carlsbad, Calif., USA), Alexa 555 conjugated goat anti-rabbit IgG (1:500; Invitrogen, Camarillo, Calif., USA), and Cy5-conjugated goat anti-mouse (1:500; Jackson Laboratory, Maine, USA) were used as secondary antibodies.

Nissl staining was performed on floating sections to evaluate neuronal loss. The sections were stained with 0.1% Cresyl violet (w/v) (Sigma-Aldrich, St. Louis, Mo., USA) and were examined with light microscopy.

BrdU immunohistochemistry was performed unmasking BrdU antigen by incubating tissue sections for 2 h in 50% formamide in 0.03 M sodium citrate and 0.3 M NaCl at 65° C., followed by 5 min wash in 0.03 M sodium citrate and 0.3 M NaCl and subsequent incubation for 30 min at 37° C.

Densitometry of immunohistochemical staining and counting the number of BrdU-immunoreactive (BrdU-IR) cells were performed as described previously.

Anxiety and exploratory activities were evaluated allowing rats to freely explore an open field for 20 min. The testing apparatus was a classic open field (i.e., a PVC square arena of 100×100 cm, with 70 cm high walls). The open field was placed in a part of the room separated from the experimentator and the control station with a black opaque curtain. Rats were individually submitted to a single 20-min session. Since for rodents the middle of a nonfamiliar arena is anxiogenic, anxiety was studied analyzing the percentage of time spent in the middle of the arena. To assess exploratory activity, the total distance the animals covered in the arena was tracked and measured. Data collection was performed using tracking files of the experiment recorded with SMART (Pan Lab/San Diego Instruments) version 2.0.14 software.

Spatial reference learning and memory were evaluated in the water maze using a procedure adapted from that previously described by Morris and collaborators. The test requires that rats use a spatial navigational strategy based on a spatial representation of the environment to find a fixed submerged escape platform. The procedure was performed in a 180-cm diameter circular tank. The pool was filled with water (21° C.±1) made opaque by adding white non-toxic paint. Acquisition started with the escape platform (14 cm diameter submerged 1 cm below water surface) in the Northwest quadrant and each animal was given 90 s to find the platform. If the rat did not find the platform in 90 s, it was gently guided to it. At the end of each trial the rat was left on the platform for 20 s then dried and returned to its home cage until the next trial. Four such acquisition trials were given on each day for three consecutive days. A test for retention (i.e., a probe trial) was given 5 days after the last day of training. During the probe trial the rat was allowed to swim in the tank without the escape platform for 60 s. The measures of learning were the time and the distance swum to reach the escape platform. For the probe trial, the tank was divided into four imaginary quadrants and a small zone where the escape platform had been during the training. The measures of the probe trial were the percentage of time spent and the percentage of distance covered in the target quadrant. Rat behavior in the water maze was monitored by a Samsung Digital Camera (SDC 4304) mounted to the ceiling and tracked and timed by a SMART (Pan Lab/San Diego Instruments) version 2.0.14 software.

Working memory task occurred in the same spatial environment as the spatial reference memory task because the achievement of this task required that animals mastered the spatial environment. The testing procedure used was similar to the spatial reference task except that the platform location changed every day. Moreover, the inter-trial intervals (ITIs) varied across days. On day 1 the ITI was 30 s, on day 2 it was 15 min and on day 3 it was 2 h. Time and distance to reach the escape platform were recorded.

Data were analyzed with STATVIEW and GraphPad software and are presented as mean±SEM for behavioral evaluations and ±SD for all the other studies. Multiple comparisons among groups were performed using ANOVA, followed by Tukey's or Fisher's post hoc test For all other comparisons (including inter-group comparisons), Student's t test was used. *$p<0.05$; **$p<0.01$.

It has been previously reported that the use of AAV1-mediated gene transfer can be a useful approach to achieve stable expression of specific transgenes. To verify if the expression of $I_{2NTF\text{-}CTF}$ in rat brain can be an etiological factor leading to the development of AD-like pathology in vivo, the lateral ventricles of p 0.5 Wistar rats AAV1 virus encoding $I_{2NTF}$ and $I_{2CTF}$ or, as a control, were bilaterally injected with GFP as seen in FIG. 25(a)-(c). Using primers targeting $I_{2NTF}$ sequence, rt-PCR of brain homogenate showed the expression of the virus encoded $I_{2NTF\text{-}CTF}$ transgene. Interestingly, transgene delivery spread from the site of injection, namely the ventricular area, to the hippocampus and cerebral cortex and it was stable since it could be observed 4 months post-infection in the animals, as seen in FIG. 25(d). As expected, GFP rats did not show infection of $I_{2NTF}$, proving that AAV vectors successfully determined infection of the desired transgene. In addition, $I_{2CTF}$ expression and localization were investigated by immunohistochemistry using anti-SET antibody which recognizes $I_2^{PP2A}$ full length and its fragment $I_{2CTF}$. Consistent with previous reports, applicant observed a predominantly nuclear staining of $I_2^{PP2A}$ with very limited staining in the cytoplasm and neurites in the different brain areas of GFP rats, as seen in FIG. 25(e)-(h). On the contrary, $I_{2NTF\text{-}CTF}$ infected rats showed a positive staining in the cytoplasm suggesting that the transgene was expressed, see FIG. 25(e)-(h). Quantification of fluorescence intensity revealed a significant increased of immunoreactivity in CA1 as seen FIG. 25(e) (Student's t test, p=0.022) and CA3, as seen in FIG. 25(f) (Student's t test, p=0.027) of the hippocampus and in ventricular area (see FIG. 25(g); Student's t test, p=0.021) of $I_{2NTF\text{-}CTF}$ compared to GFP rats.

The same trend was observed in the cortex even though it did not reach statistical significance, probably due to low signal to background ratio, see FIG. 25(h) (Student's t test, p=0.252). $I_{2NTF\text{-}CTF}$ induces abnormal hyperphosphorylation and aggregation of tau and intraneuronal Ab $I_2^{PP2A}$ is about 20% upregulated and is cleaved into $I_{2NTF}$ and $I_{2CTF}$, and translocated from the neuronal nucleus to the cytoplasm in AD brain. To determine whether these $I_2^{PP2A}$ changes could have been responsible for AD characteristic tau and any Ab changes, abnormal hyperphosphorylation and aggregation of tau and intraneuronal Ab was studied in 13-month-old $I_{2NTF\text{-}CTF}$ and -GFP control rats. The phosphorylation of tau at Ser199, Thr205, Ser262, and Ser396, which are among the major AD abnormal hyperphosphorylation sites and are known to be regulated by PP2A, were investigated. Abnormal hyperphosphorylation of tau was found at all four sites studied in the CA3 and CA1 areas of the hippocampus and in the cerebral cortex in $I_{2NTF\text{-}CTF}$ rats, as seen in FIG. 26(a). The immunostaining with anti-pT205 and anti-pS262 were more intense than with anti-pS199 and anti-pS396 in CA1 than in CA3 and cerebral cortex, and vice versa with the latter two antibodies. The exact reasons for these different region-specific immunostaining patterns remain to be investigated. Higher accessibility of pS199 and pS396 than pT205 and pS262 sites to the antibodies, different levels of transduction in different brain regions, inhibition of PP2A, the activities of tau kinases that are regulated by PP2A in different brain regions, could be among the involved factors. The 13-month-old GFP rats showed low levels of phosphorylation at pT205 and pS262, especially in the CA1 areas, all of which were markedly increased in $I_{2NTF-CTF}$ rats. Furthermore, a marked shift was found from sarkosyl-soluble to -insoluble tau, as seen in FIG. 26(b), and in its abnormal hyperphosphorylation (ptau/total tau) in $I_{2NTF-CTF}$ rats, as seen in FIG. 26(c). The $I_{2NTF-CTF}$ rats showed intraneuronal Ab both in the area of the lateral ventricle and in the cerebral cortex, as seen in FIG. 26(d). Thus, a ~20% increase in the expression of $I_{2NTF-CTF}$, see FIGS. 25(e-(h), in rat brain by 13 months of age showed early tau and Ab changes. $I_{2NTF-CTF}$ expression induced a decrease in PP2A activity and an increase in Ab1-40 and tau levels, and synaptic loss in 4-month-old rats.

In AD brain, tau and Ab pathologies are associated with an unsuccessful neurogenesis and loss of neuronal plasticity. To determine whether a shifting of the balance from neurodegeneration to regeneration of the brain by enhancing neurogenesis and neuronal plasticity at early stages of the disease can rescue cognitive impairment, the levels of the inhibition of PP2A activity, tau and Ab changes and neuronal plasticity were studied in 4-month-old $I_{2NTF-CTF}$ rats, as seen in FIG. 27.

Previously, $I_2^{PP2A}$ isolated from bovine kidney was identified as a potent inhibitor of PP2A. In the present study, PP2A activity was dramatically reduced in the hippocampus of 4-month-old $I_{2NTF-CTF}$ rats compared to the control animals, as seen in FIG. 27(a) (Student's t test, p=0.003). Nevertheless, Western blot analysis revealed that expression of $I_{2NTF-CTF}$ had no significant effect on the level of PP2Ac catalytic subunit, as seen in FIG. 27(b) (Student's t test, p=0.077).

Concomitant with the decrease in PP2A activity an immunohistochemical increase in intraneuronal Ab1-40 in the parietal association cortex of $I_{2NTF-CTF}$ rats was found, see FIG. 27(c) and (d) (Student's t test, p=0.032), while no significant changes were detected in other brain regions including the hippocampus (data not shown). This finding is consistent with AD where Ab pathology in the cerebral cortex is known to precede that in the hippocampus. However, whether $I_{2NTF-CTF}$ rats in old age will develop any extracellular Ab plaques remains to be studied.

Since PP2A has a key role in regulating tau phosphorylation and it accounts for 70% of total tau phosphatase activity in the brain, a Western blots investigation was performed to see whether tau phosphorylation at disease-relevant sites was affected. Representative immunoblots of hippocampal homogenate developed with the pan tau antibody 92e and normalized against GAPDH staining showed that tau level was significantly increased in $I_{2NTF-CTF}$ compared to GFP rats, see FIG. 27(e) (Student's t test, p=0.012). On the other hand, though there was a consistent trend for hyperphosphorylation of tau at pSer199, pThr205, pSer214, pThr217, pThr231-pSer235, pSer396, pSer396-pSer404 and pSer422 when normalized against total tau, see FIG. 27(e), these differences did not reach statistical significance in the 4-month-old $I_{2NTF-CTF}$ rats.

Besides Ab and tau pathologies, AD is characterized by neurodegeneration that is associated with decreased neuronal plasticity. $I_{2NTF-CTF}$ infection induced neurodegeneration was investigated to see whether it produced loss of synaptic and dendritic plasticity. Nissl staining revealed no apparent changes in the neuronal cytoarchitecture in the hippocampus of $I_{2NTF-CTF}$ as compared to control animals, see FIG. 27(f). Semi-quantitative immunohistochemical data showed a statistical significant decrease of fluorescent intensity of synapsin I, a synaptic vesicle associated phosphoprotein implicated in the regulation of synaptic strength, in CA3 of the hippocampus in $I_{2NTF-CTF}$ rats, see FIG. 27(g) (Student's t test, p=0.015). Similarly, quantification of mRNA levels of the dendritic marker MAP2 by RT-qPCR showed that MAP2 transcript was decreased in the cerebral cortex of $I_{2NTF-CTF}$ compared to AVV-GFP, see FIG. 27(h) (Student's t test, p=0.049).

TrkB has been recognized as a potent regulator of synaptic plasticity of the hippocampus as well as of other brain regions. Notably, TrkB-deficient mice showed impairment of long-term potentiation (LTP). We, therefore, investigated the mRNA expression of TrkB receptor in the cerebral cortex of $I_{2NTF-CTF}$ and control rats and found a decrease in the former, see FIG. 27(i) (Student's t test, p=0.018). The studies on 4-month-old $I_{2NTF-CTF}$ rats showed these animals at early stages of the AD-like changes.

Since the $I_{2NTF-CTF}$ rat model was generated based on the findings in sporadic AD, and this animal model, as described above, faithfully reproduced several key features of the human disease, Peptide 6, which is neurogenic and neurotrophic, was investigated to see whether it can alleviate the neurodegeneration caused by $I_{2NTF-CTF}$. 2.5-month-old $I_{2NTF-CTF}$ and GFP-infected rats were treated with Peptide 6 or vehicle for 7 weeks. The role of newborn hippocampal neurons is still partially unknown but several studies suggest their involvement in processing spatial memory and LTP. Adult neurogenesis occurs primarily in two brain regions: the subventricular zone and the subgranular zone (SGZ) of the DG. BrdUpositive cells were predominantly localized in the inner granular cell layer (iGCL) at the border of the GCL and the hilus. Analysis of the number of positive cells, using unbiased stereological approaches, revealed significant differences among groups in the number of BrdU-positive cells in the SGZ of the DG, see FIG. 28(a)-(e) (ANOVA, p=0.034). A marked increase in the number of BrdUpositive cells was found in GFP rats treated with Peptide 6 compared to vehicle-treated animals (Fisher's post hoc test, p=0.007). Interestingly, Peptide 6 significantly increased the number of BrdU-positive cells also in $I_{2NTF-CTF}$ compared to vehicle-treated $I_{2NTF-CTF}$ rats (Fisher's post hoc test, p=0.050). Differentiation of newborn cells was assessed measuring the co-localization of the mature neuronal marker, NeuN, with the BrdU-IR cells. A significant difference among groups was observed, see FIG. 28(f) (ANOVA, p=0.019). Treatment with Peptide 6 significantly increased the number of NeuN-BrdU-IR cells in $I_{2NTF-CTF}$ compared to the vehicle-treated control animals (Student's t test, p=0.005).

Since the survival of newborn neurons has been shown to require BDNF signaling and BDNF is a regulator of axonal outgrowth, chronic Peptide 6 treatment was studied to see whether it can activate BDNF pathway. Quantification of mRNA level of BDNF in the parietal association cortex using RT-qPCR showed differences between groups (FIG. 28(g), ANOVA, p=0.029). In particular, treatment with Peptide 6 increased BDNF transcription in GFP (Student's t test, p=0.005) as well as in $I_{2NTF-CTF}$ (Student's t test, p=0.036) rats compared to untreated controls. The expression of BDNF mRNA in $I_{2NTF-CTF}$ rats was decreased compared to the other groups even though it did not reach statistical significance (Student's t test, p=0.053). The decrease in mRNA level of TrkB receptor in $I_{2NTF\text{-}CTF}$ rats was attenuated on treatment with Peptide 6, as seen in FIG. 28(*h*).

Synaptic pruning is a feature of AD pathology. The expression of AMPA receptor subunits was evaluated due to their essential role for synaptic transmission and LTP as well as cellular mechanisms which are connected with learning and memory. Peptide 6 was able to induce a significant increase of the GluR1 subunit of AMPA receptors in the hippocampi of GFP compared to GFP treated with vehicle, see FIG. 29(*a*) (Student's t test, p=0.009). In addition, GluR2/3 expression was significantly higher in the hippocampus of Peptide 6-treated $I_{2NTF\text{-}CTF}$ than the vehicle-treated GFP rats, see FIG. 29(*a*) (Student's t test, p=0.001) whereas no significant differences among groups were observed in the level of PSD95, see FIG. 29(*a*) (ANOVA, p=0.23). Immunohistochemical investigation in the DG confirmed the same pattern highlighting a specific increase in the immunoreactivity for GluR2/3 in $I_{2NTF\text{-}CTF}$ rats treated with Peptide 6 compared to the vehicle-treated animals, see FIG. 29(*b*) (Student's t test, p=0.033). Immunohistochemical staining revealed a decrease in the density of the NMDA receptor subunit NR1-positive neurons in the CA1, see FIG. 29(*c*) (ANOVA, p=0.016) and in the CA3, see FIG. 29(*d*) (ANOVA, p=0.026) of the hippocampus in $I_{2NTF\text{-}CTF}$ rats. Peptide 6 administration enhanced the expression of NR1 in CA3 and CA1 in GFP but not the $I_{2NTF\text{-}CTF}$ rats.

The protein expression of Egr-1 was examined, which is an immediate-early response gene and a marker of the activation of neuronal circuits. There was a significant difference among groups, see FIG. 29(*e*) (ANOVA, p=0.0005) and in particular increased expression of Egr-1 in GFP (Student's t test, p=0.018) and $I_{2NTF\text{-}CTF}$ (Student's t test, p=0.012) rats after Peptide 6 treatment.

Employing antibodies directed to specific presynaptic structures, applicant assessed whether Peptide 6 could rescue synaptic loss in the brains of $I_{2NTF\text{-}CTF}$ rats. Immunohistochemical studies showed that Peptide 6 significantly increased the expression of synapsin I in the CA1, see FIG. 30(*a*) (Fisher's post hoc, p=0.041) and CA3, see FIG. 30(*b*) (Fisher's post hoc, p=0.043) of the hippocampus and in the parietal association cortex, see FIG. 30(*c*) (Fisher's post hoc, p=0.047) of $I_{2NTF\text{-}CTF}$ compared to vehicle-treated rats. It is worth noting that the significant loss in the expression of this protein in the CA3 of $I_{2NTF\text{-}CTF}$ rats compared to GFP was completely reversed after Peptide 6 treatment. In addition, Peptide 6 increased synaptophysin level in the CA3, see FIG. 30(*d*) (Student's t test, p=0.018) and MAP2 level in the CA1, see FIG. 30(*e*) (ANOVA, p=0.004; Fisher's post hoc, p=0.019) of $I_{2NTF\text{-}CTF}$ rats. Both MAP2 immunoreactivity, see FIG. 30(*e*) (Fisher's post hoc, p=0.004) and mRNA, see FIG. 30(*f*) (Student's t test, p=0.047) were increased in $I_{2NTF\text{-}CTF}$ rats treated with Peptide 6. Synapsin I mRNA level in the cerebral cortex showed differences among groups, see FIG. 30(*g*) (ANOVA, p=0.036), which was reduced in $I_{2NTF\text{-}CTF}$ rats compared to GFP, see FIG. 30(*g*) (Student's t test, p=0.048) and it was rescued by Peptide 6 (Student's t test, p=0.024). Peptide 6 administration increased the mRNA level of Neurofilament M in $I_{2NTF\text{-}CTF}$, see FIG. 30(*h*) (Student's t test, p=0.022) as well as GFP (Student's t test, p=0.030) rats compared to vehicle-treated animals. Moreover, the mRNA level of tau was increased in $I_{2NTF\text{-}CTF}$ treated with Peptide 6 compared to the vehicle treated $I_{2NTF\text{-}CTF}$, see FIG. 30(*i*) (ANOVA, p=0.036; Student's t test, p=0.049) or GFP rats (Student's t test, p=0.040). These data support the remodeling and enhancement of neuronal architecture by Peptide 6 treatment. Collectively, these results suggest an altered molecular composition of the pre-synaptic machinery, especially within the CA3 area in the hippocampus of $I_{2NTF\text{-}CTF}$ rats which was rescued by Peptide 6

Although Peptide 6, as shown above, works as a neurotrophin, it nevertheless was investigated to determine whether it had any effect on Ab and tau changes in $I_{2NTF\text{-}CTF}$ rats. While Peptide 6 did not have any significant effect on Ab accumulation, as determined by immunohistochemical staining (figure not shown), it increased the tau mRNA level, see FIG. 30(*i*), but caused no significant changes in the hyperphosphorylation of tau at several AD abnormal sites studied (figure not shown). The lack of any significant effect of Peptide 6 on Ab and abnormal hyperphosphorylation of tau in the present study is consistent with our previous similar observations in 3xTg-AD transgenic mice treated with the peptide at early stages of the pathology. Rescue of cognitive impairment by Peptide 6 in $I_{2NTF\text{-}CTF}$ rats.

During the period of the treatment the condition of individual animals was assessed every week by evaluating physical state and grooming. No alteration in general physical state including grooming and posture was observed, either in the $I_{2NTF\text{-}CTF}$ rats treated with Peptide 6 or vehicle. Evaluation of reflexes and muscle strength using the clasping reflex, see FIG. 31(*a*) (ANOVA, p=0.697) and prehensile traction test, see FIG. 31(*b*) (ANOVA, p=0.405) did not reveal any significant differences between groups. Assessment of anxiety and exploration in the open field did not reveal any significant difference among groups. All animals spent similar time in the center of the arena, see FIG. 31(*c*) (ANOVA, p=0.267) and covered similar distance within the open field, see FIG. 31(*d*) (ANOVA, p=0.657). These results showed that neither expression of $I_{2NTF\text{-}CTF}$ nor treatment with Peptide 6 induced any modification of general behavior. This suggests that treatment with Peptide 6 did not provoke any side effects. Spatial reference memory task.

Cognitive evaluation focused on testing the hippocampal function since it is the first structure affected in Alzheimer disease and it is the key structure for memory processing. Animals were tested for a spatial reference memory task, followed by a spatial working memory task in the same experimental environment. The swim speed of the animals was analyzed. Statistical analysis did not reveal any difference among groups, see FIG. 31(*e*) (ANOVA, p=0.555). Therefore, results of the training were analyzed as latency to reach the submerged platform in the water maze. During the training of the task, $I_{2NTF\text{-}CTF}$ rats displayed delayed performance compared to GFP groups, see FIG. 31(*f*) (ANOVA, p=0.063; Fisher's post hoc test, p<0.025). This finding showed that AAV $I_{2NTF\text{-}CTF}$ rats were impaired in the learning of the task compared to GFP rats, but that treatment with Peptide 6 rescued this impairment. Global average performance during training clearly showed the impairment of $I_{2NTF\text{-}CTF}$ compared to GFP rats treated with vehicle, see FIG. 31(*g*) (Student's t test, p=0.045) or Peptide 6 (Student's t test, p=0.037), and that treatment with Peptide 6 increased $I_{2NTF\text{-}CTF}$ rats' performance compared to GFP animals' levels (ANOVA, p=0.040). Statistical analyses of the probe trial, showed that $I_{2NTF\text{-}CTF}$ rats visited significantly less the target quadrant than $I_{2NTF\text{-}CTF}$ rats treated with Peptide 6, see FIG. 31(*h*) (Student's t test, p=0.007). $I_{2NTF\text{-}CTF}$ rats treated with Peptide 6 spent similar time in the target quadrant compared to GFP groups (Student's t test, p=0.122). These results confirmed the impairment of $I_{2NTF\text{-}CTF}$ rats to encode and memorize spatial information, i.e. spatial coordinates of the submerged platform and that treatment with Peptide 6 reduced spatial impairment.

The working memory of the animals was tested in the same water maze and experimental environment as above for the spatial reference task. The escape latency to find the submerged platform at inter-trial-intervals (ITI) was 30 s on day 1, 15 min on day 2, and 2 h on day 3. Statistical analyses did not show any difference among groups when the ITI was 30 s or 15 min, see FIG. 31(i) (ANOVA, p=0.617); FIG. 31(j) (ANOVA, p=0.558). But, when the ITI increased to 2 h, $I_{2NTF-CTF}$ rats treated with vehicle displayed longer escape latencies than other groups, see FIG. 31(k) (ANOVA, p=0.002, Fisher's post hoc test, p=0.007), and $I_{2NTF-CTF}$ rats treated with Peptide 6 presented similar performance as GFP rats (Fisher's post hoc test, p<0.419). These results showed that $I_{2NTF-CTF}$ rats displayed working memory impairment for long delays of retention but that treatment with Peptide 6 alleviated this deficit.

Despite the fact that the sporadic form of AD accounts for over 99% of the cases, to date, most of the experimental animal models are based on the familial form of the disease and are overexpression transgenic mice. AD is multifactorial and development of rational therapeutic drugs will require understanding of various etiopathogenic mechanisms of this disease. PP2A, which is the major regulator of tau phosphorylation, is down-regulated in AD brain. A cause of decreased PP2A activity is the overexpression and cleavage and translocation of its inhibitor, $I_2^{PP2A}$ from the neuronal nucleus to the cytoplasm. The present example shows that the expression of the $I_2^{PP2A}$ cleavage products, $I_{2NTF}$ and $I_{2CTF}$, in the brain reproduces several histopathological features and cognitive impairment in rat, yielding a disease-relevant animal model of sporadic AD. A transgenic truncated tau overexpression rat model was previously reported to show extensive tau pathology, primarily in the brain stem, and motor dysfunction in the absence of any Ab accumulation.

Aging is the biggest known risk factor for AD. Even in carriers of the disease-causing mutations of APP, presenilin 1 and presenilin 2, the disease onset is mostly in the fifth or sixth decade of life. It is possible that the brain's regenerative capacity is slowly, progressively compromised with age and becomes insufficient to negate the specific disease pathogenesis. The present example shows that chronic treatment with Peptide 6 can enhance neurogenesis and neuronal plasticity, and can rescue cognitive impairment in $I_{2NTF-CTF}$ rats. In an attempt to evaluate the contribution of $I_2^{PP2A}$ cleavage to the cognitive deficit and major features observed in AD, virally mediated gene transfer of both $I_{2NTF}$ and $I_{2CTF}$ was employed. One of the major advantages of this approach, compared to the use of transgenic animals, is that long-term transgene expression is achieved without affecting the genetic background of the animal. Rats injected with AAV serotype 1 vector encoding the two fragments of $I_2^{PP2A}$ showed a marked reduction of PP2A activity.

Although in $I_{2NTF-CTF}$ rat hippocampus the reduction of PP2A activity was successfully achieved, the evidence of infection was provided by rt-PCR and immunohistochemistry; the level of expression was too low to be detected by Western blots. It is worth noting that a small amount of the inhibitor was sufficient to achieve a significant reduction in PP2A activity and the consequent neurodegeneration and cognitive impairment in $I_{2NTF-CTF}$ rats.

Reduction of PP2A activity affects APP regulation, contributing to Ab production as shown by the increased expression of Ab1-40 in the cerebral cortex. As is the case in human AD and 3xTg-AD mice, Ab alterations were found in the absence of a pronounced alteration of tau phosphorylation in 4-month-old animals. Indeed, in 3xTg-AD mice, tau pathology becomes apparent only between 12 and 15 months of age and staining with PHF1 antibody, a marker of late stage of tau pathology, is evident only at 18 months of age. While marked increase in abnormal hyperphosphorylation and aggregation of tau was found in 13-month-old $I_{2NTF-CTF}$ rats, at 4 months of age these animals showed an increase in the total tau level. Even at this early stage, practically all this increase in tau was in the form of the hyperphosphorylated protein. Interestingly, by 13 months in $I_{2NTF-CTF}$ rats the level of total tau was decreased. This is similar to what was reported in 8-month AAV1-$I_{2CTF}$ rats and probably represents loss of axonal plasticity. The intraneuronal Ab was more evident in 13-month-old as compared to the 4-month-old $I_{2NTF-CTF}$ rats. A recent report has suggested that intraneuronal Ab is most likely APP. However, several major Ab research groups in the field disagree on this issue (see http://www.alzforum.org).

In this example, applicant thus presented a model in which AAV1-induced expression of $I_{2NTF}$ and $I_{2CTF}$ resulted in decreased activity of PP2A coupled with a significant increase in abnormal hyperphosphorylation and aggregation of tau and intraneuronal accumulation of Ab at 13 months of age. $I_{2NTF-CTF}$ rats at 4 months of age developed a clinical phenotype that included spatial and working memory impairments as they were not able to encode and store spatial representation of the environment and coordinates of the submerged platform. Moreover, $I_{2NTF-CTF}$ expression led to neurodegeneration and loss of dendritic and synaptic plasticity. This suggests that synaptic alteration is one of the earliest neurodegenerative consequences of PP2A-reduced activity. Remarkably, impairment of synaptic plasticity has been recognized as a key early event in the pathogenesis of AD which consequently affects synaptic remodeling and LTP. Interestingly, several reports suggested that alteration of hippocampal synaptic plasticity precedes extracellular plaque deposition and neuronal loss Likewise, synaptic pathology has been detected as earliest manifestation of the disease before the formation of neurofibrillary tangles or marked tau hyperphosphorylation in P301S tau transgenic mice. In addition, early studies supported a link between the degree of cognitive decline in AD patients and changes in the levels of presynaptic markers. Remarkably, synapsin I is associated with axogenesis and synaptogenesis and decreased mRNA and protein levels of this presynaptic marker in $I_{2NTF-CTF}$ compared to GFP rats observed in the present study probably contributed to the impairment in spatial and working memory.

In this regard, the present example supports the use of neurotrophic-based peptides to rescue synaptic and behavioral dysfunction. Molecules able to enhance synaptogenesis and neuronal plasticity may increase the resistance to the clinical manifestation of the pathology, thereby delaying the onset of clinical expression. Neurodegenerative disorders may indeed affect neurotrophic factor functions, reducing adaptation of neurons to disease-related alterations. Notably, unlike the parent molecule, Peptide 6 administration showed neurotrophic properties without inducing adverse effects. Furthermore, the efficacy of peripheral administration at nanomolar level and the capability to penetrate the blood-brain barrier render Peptide 6 a promising pharmacological strategy.

The present example provides strong evidence that Peptide 6 increased mRNA level of the BDNF receptor, TrkB, a potent presynaptic activator. Several reports have indeed demonstrated that BDNF/TrkB signaling can modulate synaptic function, increasing levels of pre-synaptic proteins and dendritic branching. In the present example, the increase in BDNF mRNA upon treatment with Peptide 6 is consistent with the increased expression of the dendritic marker MAP2 and synaptic markers synapsin I and synaptophysin. The increase of endogenous BDNF levels in the brain of Peptide 6-treated animals represents an important finding as BDNF mRNA levels have been found to be diminished in AD brain. Since cholinergic neurons are stimulated by BDNF, reduced availability of this factor could trigger degeneration of this neuronal population. Moreover, BDNF knockout mice showed reduced LTP, suggesting that BDNF might play an important role in neuroplasticity connected with learning and memory. Thus, activation of TrkB receptor initiates complex signaling pathways that modify synaptic structure and function. The increased mRNA level of tau and neurofilament M as well as stimulation of the early response gene Egr-1 in the present study suggest that, beside potentiating BDNF-induced transmitter release, Peptide 6 heightened synaptic outgrowth. On the other hand, in $I_{2NTF-CTF}$ rats, Peptide 6 did not alter the level of PSD-95 and NMDA receptor (NR1) suggesting that it exerts its effect primarily up-regulating vesicle-associated synaptic proteins. Nevertheless, the possibility that longer treatment of the $I_{2NTF-CTF}$ rats can have a significant beneficiary effect of the Peptide on the post-synaptic machinery cannot be rules out. As a matter effect, post-synaptic AMPA receptor subunits GluR1 and GluR 2/3 were increased due to Peptide 6 treatment.

Behavioral rescue in cognition may be, besides increase in neuronal plasticity, also due to Peptide 6-mediated enhancement in the expression of newborn hippocampal neurons as shown by the increase of BrdU incorporation. Several neurodegenerative disorders, including AD, have been shown to have impaired neurogenesis. As newborn neurons are incorporated in the DG network, they improve DG plastic properties by facilitating the expression of LTP and the encoding of novel information. Thus, modulation of hippocampal neurogenesis represents an important goal as newborn neurons can be recruited into new memory networks.

This example and prior examples support the possibility that reduced activity of PP2A due to enhanced cleavage of its inhibitor $I_2^{PP2A}$ probably represents an etiopathogenic mechanism of AD. By demonstrating loss of synaptic integrity, there is strong evidence implicating synaptic pathology as an early neurotoxic consequence of expression of $I_{2NTF-CTF}$ resulting in marked cognitive impairment. AAV-$I_{2NTF-CTF}$ virus delivered locally to the brain can be used effectively to obtain an early stage model of sporadic AD. Furthermore, peripheral administration of Peptide 6 represents a valuable tool to reverse hippocampal function deficits, rescuing the short-term capability to encode and remember new information in association with the stimulation of neurogenesis, dendritic and synaptic plasticity without affecting tau and Ab changes.

What is claimed is:

1. A method of treating a subject having Alzheimer's disease comprising the step of administering a therapeutic amount of a neurotrophic peptide consisting of the amino acid sequence selected from the group consisting of VGDGGLFEKKL (SEQ ID NO: 1), GDGGLFEK (SEQ ID NO: 5), GLFEKKLW (SEQ ID NO: 6), VGDG (SEQ ID NO: 7), GDGG (SEQ ID NO: 8), DGGL (SEQ ID NO: 9), and GGLF (SEQ ID NO: 10).

2. The method of claim 1, wherein said neurotrophic peptide is administered peripherally.

3. The method of claim 1, wherein said neurotrophic peptide is administered subcutaneously.

4. The method of claim 1, wherein said neurotrophic peptide is administered orally.

5. The method of claim 1, wherein said neurotrophic peptide is administered intraperitoneally.

6. A method of treating a subject having Alzheimer's disease comprising the step of administering a therapeutic amount of a neurotrophic peptide consisting of the amino acid sequence DGGL (SEQ ID NO: 9) bound to an adamantane building block.

7. The method of claim 6, wherein said adamantane building block is bound to a C-terminus of said neurotrophic peptide.

8. The method of claim 6, wherein another adamantane building block is bound to an N-terminus of said neurotrophic peptide.

9. The method of claim 6, wherein said adamantane building block comprises 3-aminoadamantane-1-carboxylic acid.

10. The method of claim 6, wherein said neurotrophic peptide bound to said adamantane building block consists of the sequence Ac-DGGL$^A$G-NH$_2$ (SEQ ID NO: 12).

11. The method of claim 6, wherein said neurotrophic peptide bound to said adamantane building block consists of the sequence Ad-CO-DGGL$^A$G-NH$_2$ (SEQ ID NO: 13).

* * * * *